(12) United States Patent
Hiller et al.

(10) Patent No.: US 10,544,395 B2
(45) Date of Patent: Jan. 28, 2020

(54) METHOD OF CELL CULTURE

(71) Applicant: Pfizer Inc., New York, NY (US)

(72) Inventors: Gregory Walter Hiller, Wakefield, MA (US); Bhanu Chandra Mulukutla, Lawrence, MA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 15/126,489

(22) PCT Filed: Mar. 17, 2015

(86) PCT No.: PCT/IB2015/051943
§ 371 (c)(1),
(2) Date: Sep. 15, 2016

(87) PCT Pub. No.: WO2015/140708
PCT Pub. Date: Sep. 24, 2015

(65) Prior Publication Data
US 2017/0107552 A1 Apr. 20, 2017

Related U.S. Application Data

(60) Provisional application No. 61/955,273, filed on Mar. 19, 2014.

(51) Int. Cl.
*C12N 5/00* (2006.01)
*C12N 5/071* (2010.01)
*C12P 21/02* (2006.01)

(52) U.S. Cl.
CPC ........ *C12N 5/0682* (2013.01); *C12N 2500/32* (2013.01); *C12N 2500/33* (2013.01); *C12N 2500/34* (2013.01); *C12N 2501/80* (2013.01); *C12N 2501/999* (2013.01)

(58) Field of Classification Search
CPC ...... C07K 14/395; C07K 16/00; C12N 15/81; C12N 9/88; C12N 2500/32; C12N 2500/33; C12N 2500/34; C12N 2501/80; C12N 2501/999; C12N 5/0682; C12N 15/70; C12N 5/0018; C12N 9/001; C12N 9/1029; C12N 1/20; C12N 15/52; C12N 15/74; C12N 1/36; C12N 15/72; C12N 2510/00; C12N 2510/02; C12N 2511/00; C12P 13/02; C12P 13/04; C12P 7/40; C12P 7/16; C12P 17/182; C12P 19/34; C12P 21/02; C12P 7/42; C12P 7/52; C12P 7/56; C12P 7/62; Y02E 50/10
See application file for complete search history.

(56) References Cited

U.S. PATENT DOCUMENTS 15,762,345 * 3/2018 Hiller et al ............. C12P 7/625
435/135
2005/0070013 A1 3/2005 Luan
2006/0199260 A1* 9/2006 Zhang ................. B01F 13/0059
435/293.1
2009/0042253 A1* 2/2009 Hiller .................... C12M 29/16
435/70.3
2018/0265904 A1* 9/2018 Hiller ....................... C12P 7/62

FOREIGN PATENT DOCUMENTS

DE 239 222 A1 9/1986

OTHER PUBLICATIONS

Marten et al. (The FASEB Journal (1994), Biotechnology and Bioengineering, vol. 108, No. 6, Jun. 24, 2011, pp. 1328-1337).*
M. Gagnon et al: "High-End pH-controlled delivery of glucose effectively suppresses lactate accumulation in CHO Fed-batch cultures", Biotechnology and Bioengineering, vol. 108, No. 6, Jun. 24, 2011,, pp. 1328-1337.
N. W. Marten et al: "Effect of amino acid limitation on the expression of 19 genes in rat hepatoma cells". The FASEB Journal, May 1, 1994, p. 538.
G. W. Hiller et al: "Transient responses of hybridoma cells in continuous culture to step changes in amino acid and vitamin concentrations", Biotechnology and Bioengineering, vol. 44, No. 3, Jul. 1, 1994 (Jul. 1, 1994), pp. 303-321.
Y. Jin et al: "Effects of homocysteine on metabolic pathways in cultured astrocytes", Neurochemistry International, Pergamon Press, Oxford, GB, vol. 52, No. 8, Jun. 1, 2008 (Jun. 1, 2008), pp. 1410-1415.
Altamirano C, Illanes A, Becerra S, Cairo JJ, Godia F (2006) Considerations on the lactate consumption by CHO cells in the presence of galactose. Journal of biotechnology 125: 547-556.
Bertoni JM (1981) Competitive inhibition of rat brain hexokinase by 2-deoxyglucose, glucosamine, and metrizamide. Journal of neurochemistry 37: 1523-1528.
Carinhas N, et al (2013) Metabolic Signatures of GS-CHO Cell Clones Associated with Butyrate Treatment and Culture Phase Transition, Biotechnology and Bioengineering, vol. 110, No. 12, 3244-3257.
Clem B, Telang S, Clem A, Yalcin A, Meier J, Simmons A, Rasku Ma, Arumugam S, Dean Wl, Eaton J, Lane A, Trent Jo, Chesney J (2008) Small-molecule inhibition of 6-phosphofructo-2-kinase activity suppresses glycolytic flux and tumor growth. Molecular cancer therapeutics 7: 110-120.

(Continued)

*Primary Examiner* — Deborah K Ware
(74) *Attorney, Agent, or Firm* — Stephen E. Moyer

(57) ABSTRACT

A method of cell culture comprising providing cells in a cell culture medium to start a cell culture process, and,
maintaining at least one metabolite selected from 3-(4-hydroxyphenyl)lactate, 4-hydroxyphenylpyruvate, phenyllactate, indolelactate, indolecarboxylic acid, homocysteine, 2-hydroxybutyric acid, isovalerate and formate below a concentration C1 in the cell culture medium, wherein C1 is 3 mM and/or
(ii) maintaining at least one amino acid selected from phenylalanine, tyrosine, tryptophan, methionine, leucine, serine, threonine and glycine below a concentration C2 in the cell culture medium, wherein C2 is 2 mM.

19 Claims, 23 Drawing Sheets

(56) References Cited

OTHER PUBLICATIONS

Duvel K, Yecies Jl, Menon S, Raman P, Lipovsky Ai, Souza Al, Triantafellow E, Ma Q, Gorski R, Cleaver S, Vander Heiden Mg, MacKeigan Jp, Finan Pm, Clish Cb, Murphy Lo, Manning Bo (2010) Activation of a metabolic gene regulatory network downstream of mTOR complex 1. Molecularce/139: 171-183.

Kim Sh, Lee Gm (2007a) Down-regulation of lactate dehydrogenase-A by siRNAs for reduced lactic acid formation of Chinese hamster ovary cells producing thrombopoietin. Applied microbiology and biotechnology 74: 152-159.

Kim Sh, Lee Gm (2007b) Functional expression of human pyruvate carboxylase for reduced lactic acid formation of Chinese hamster ovary cells (DG44). Applied microbiology and biotechnology 76: 659-665.

Lee Hlt, Boccazzi P, Gorret N, Ram Rj, Sinskey Aj (2004) In situ bioprocess monitoring of *Escherichia coli* bioreactions using Raman spectroscopy. Vibrational Spectroscopy 35: 131-137.

Lee Js, Lee Gm (2012) Rapamycin treatment inhibits CHO cell death in a serum-free suspension culture by autophagy induction. Biotechnology and bioengineering 109: 3093-3102.

Li B, Ryan Pw, Ray Bh, Leister Kj, Sirimuthu Nm, Ryder Ag (2010) Rapid characterization and quality control of complex cell culture media solutions using raman spectroscopy and chemometrics. Biotechnology and bioengineering 107: 290-301.

Morgan Hp, O'Reilly Fj, Wear Ma, O'Neill Jr, Fothergill-Gilmore La, Hupp T, Walkinshaw Md (2013) M2 pyruvate kinase provides a mechanism for nutrient sensing and regulation of cell proliferation. Proceedings of the National Academy of Sciences of the United States of America 110: 5881-5886.

Mulukutla Bc, Gramer M, Hu Ws (2012) On metabolic shift to lactate consumption in fedbatch culture of mammalian cells. Metabolic engineering 14: 138-149.

Whelan J, Craven S, Glennon B (2012) In situ Raman spectroscopy for simultaneous monitoring of multiple process parameters in mammalian cell culture bioreactors. Biotechnology progress 28: 1355-1362.

Whitehouse S, Cooper Rh, Randle Pj (1974) Mechanism of activation of pyruvate dehydrogenase by dichloroacetate and other halogenated carboxylic acids. The Biochemical journal 141: 761-774.

Wlaschin Kf, Hu Ws (2007) Engineering cell metabolism for high-density cell culture via manipulation of sugar transport. Journal of biotechnology 131: 168-176.

Yi W, Clark Pm, Mason De, Keenan Mc, Hill C, Goddard Wa, 3rd, Peters Ec, Driggers EM, Hsieh-Wilson LC (2012) Phosphofructokinase 1 glycosylation regulates cell growth and metabolism. Science 337: 975-980.

Zhou M, Crawford Y, Ng D, Tung J, Pynn Af, Meier A, Yuk Ih, Vijayasankaran N, Leach K, Joly J, Snedecor B, Shen A (2011) Decreasing lactate level and increasing antibody production in Chinese Hamster Ovary cells (CHO) by reducing the expression of lactate dehydrogenase and pyruvate dehydrogenase kinases. Journal of biotechnology 153: 27-34.

Zhu G, Zhu X, Fan Q, Wan X (2011) Raman spectra of amino acids and their aqueous solutions. Spectrochimica acta Part A, Molecular and biomolecular spectroscopy 78: 1187-1195.

* cited by examiner

METHOD OF CELL CULTURE

CROSS-REFERENCE TO RELATED APPLICATIONS

This application claims priority under 35 U.S.C. § 120 as a national stage entry of International Application No. PCT/IB2015/051943, filed Mar. 17, 2015, which claims priority under U.S.C. § 119(e) to U.S. Provisional Patent Application No. 61/955,273, filed Mar. 19, 2014, which is herein incorporated in its entirety by reference.

FIELD OF THE INVENTION

The invention relates to a method of cell culture where the concentration of one or more of phenylalanine, tyrosine, tryptophan, methionine, leucine, serine, threonine and glycine and/or one or more of 3-(4-hydroxyphenyl)lactate, 4-hydroxyphenylpyruvate, phenyllactate, indolelactate, indolecarboxylic acid, homocysteine, 2-hydroxybutyric acid, isovalerate and formate are maintained at low levels in the cell culture medium. The invention also relates to a method of cell culture for improving cell growth and productivity, in particular in fed-batch culture of mammalian cells at high cell density. The invention also relates to media for use in said methods.

BACKGROUND OF THE INVENTION

Proteins have become increasingly important as diagnostic and therapeutic agents. In most cases, proteins for commercial applications are produced in cell culture, from cells that have been engineered and/or selected to produce unusually high levels of a particular protein of interest. Optimization of cell culture conditions is important for successful commercial production of proteins. Mammalian cells have inefficient metabolism which causes them to consume large amounts of nutrients and convert a significant amount of them to byproducts. The byproducts are released into the culture and accumulate over the course of the culture. Lactate and ammonia, known to be the conventional inhibitors of cells in culture, are the two major byproducts of cellular metabolism that accumulate to high levels in culture and beyond certain concentrations, they start inhibiting the growth and productivity of cells in culture. Cell culture methods aimed at reducing the amount of lactate and ammonia in the cell culture medium have been developed and can increase the growth and the productivity of mammalian cells. The cell growth, however, still slows down even when concentrations of lactate and ammonia are kept low, thereby limiting the maximum cell density and productivity of the cells.

Therefore, there is a need for the development of improved cell culture systems for optimum production of proteins. In particular there is a need for cell culture methods providing an increased viable cell density and/or titer.

SUMMARY OF THE INVENTION

The invention relates to a method of cell culture comprising
(i) providing cells in a cell culture medium to start a cell culture process, and,
(ii) maintaining at least one metabolite selected from 3-(4-hydroxyphenyl)lactate, 4-hydroxyphenylpyruvate, phenyllactate, indolelactate, indolecarboxylic acid, homocysteine, 2-hydroxybutyric acid, isovalerate and formate below a concentration C1 in the cell culture medium, wherein C1 is 3 mM and/or
maintaining at least one amino acid selected from phenylalanine, tyrosine, tryptophan, methionine, leucine, serine, threonine and glycine below a concentration C2 in the cell culture medium wherein C2 is 2 mM.

The invention also relates to a cell culture medium comprising low concentration of one or more of phenylalanine, tyrosine, tryptophan, methionine leucine, serine, threonine and glycine.

Figure 10:
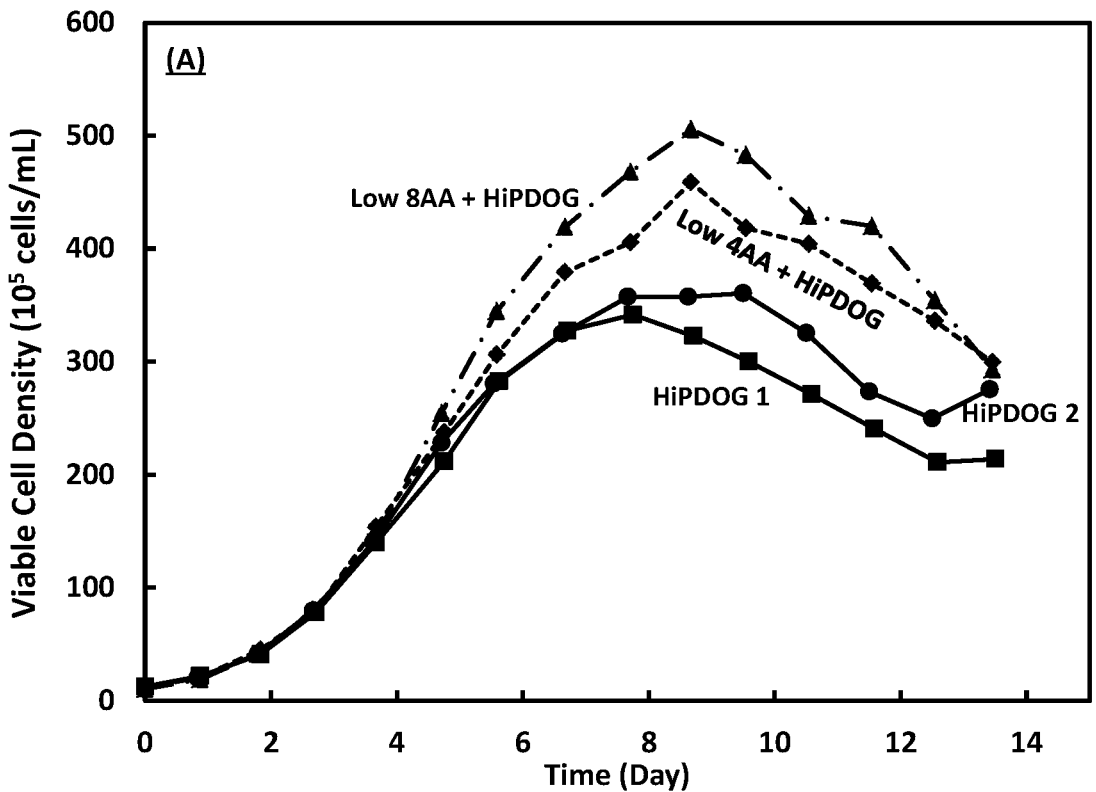
Figure 10:
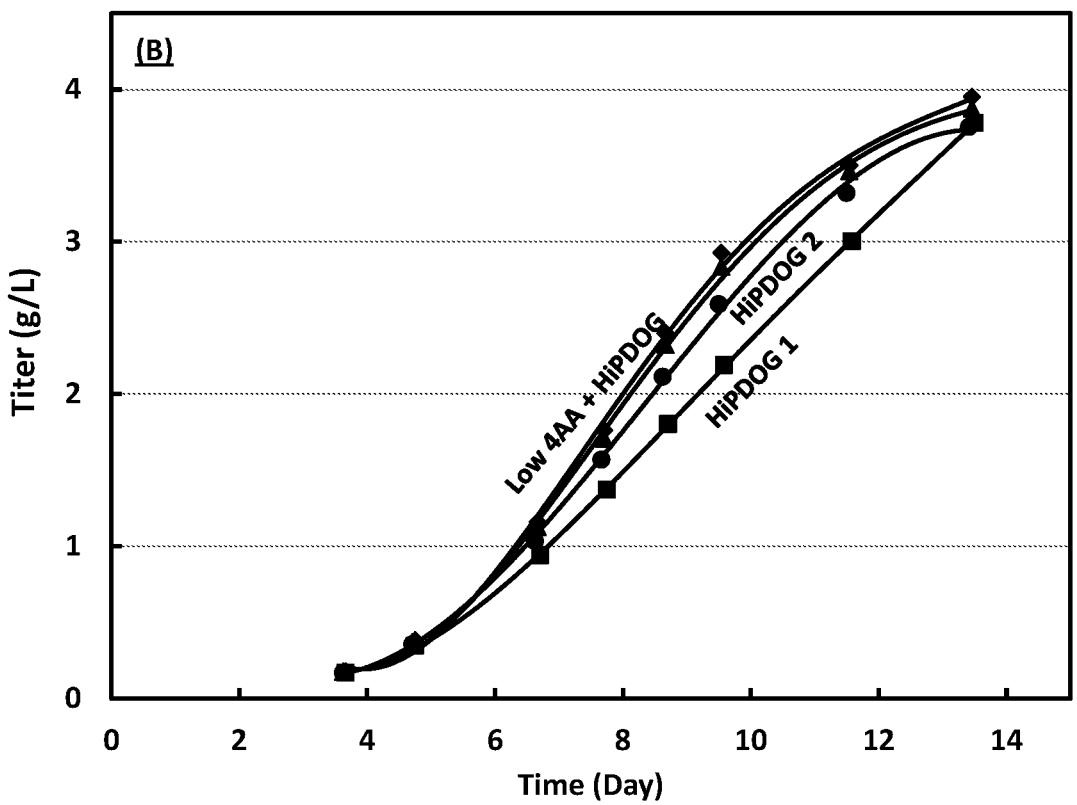
Figure 11:
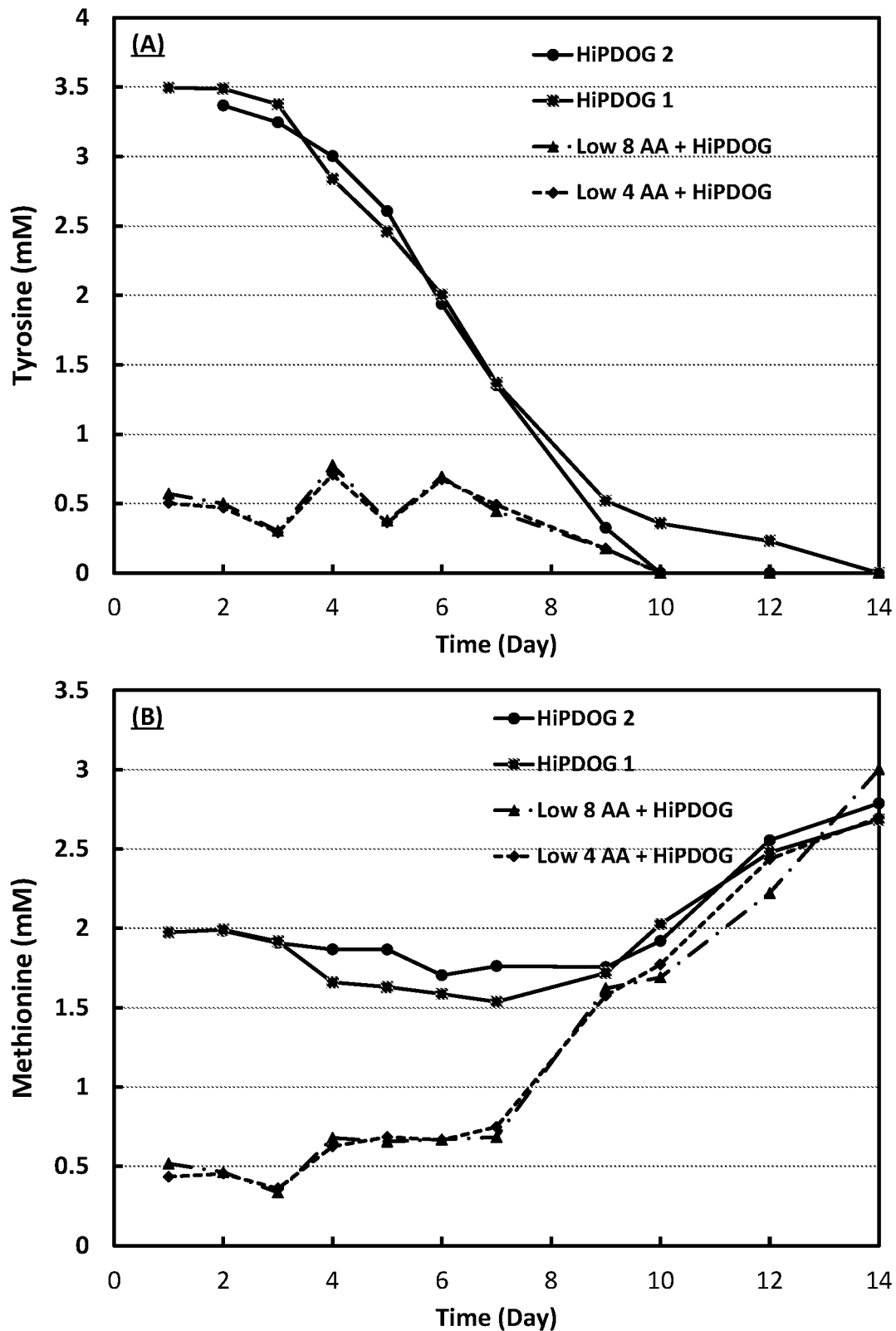
Figure 12:
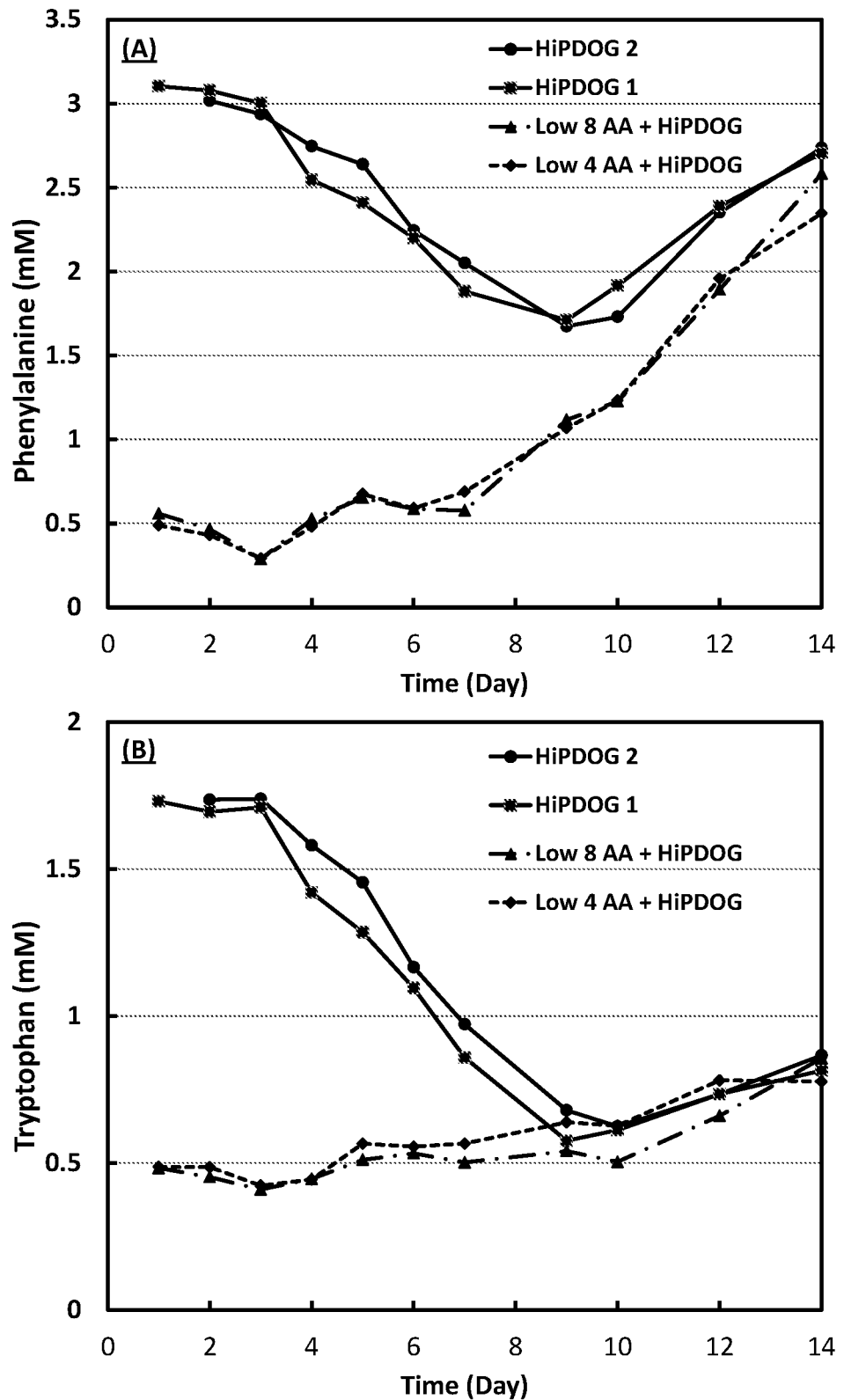
Figure 13:
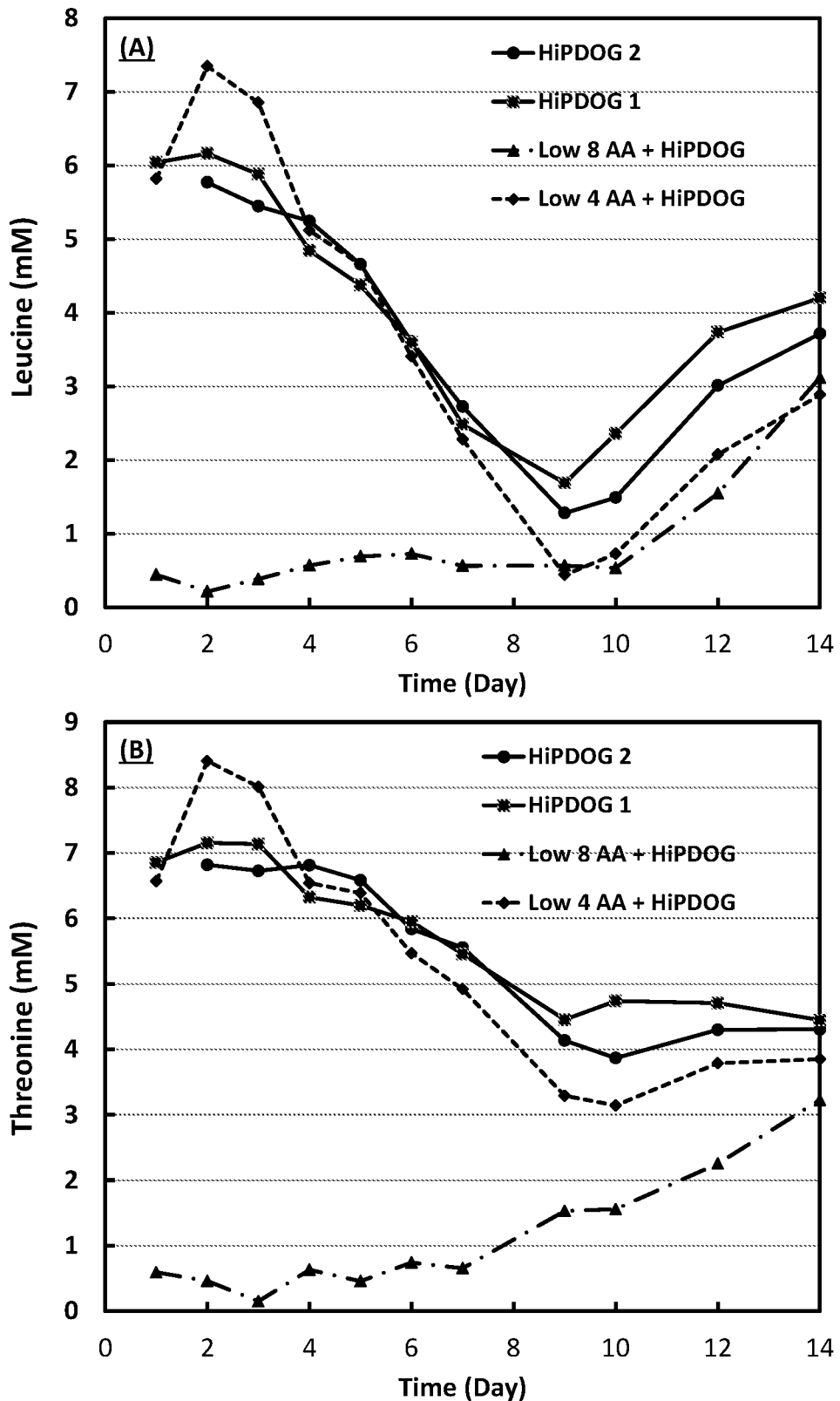
Figure 14:
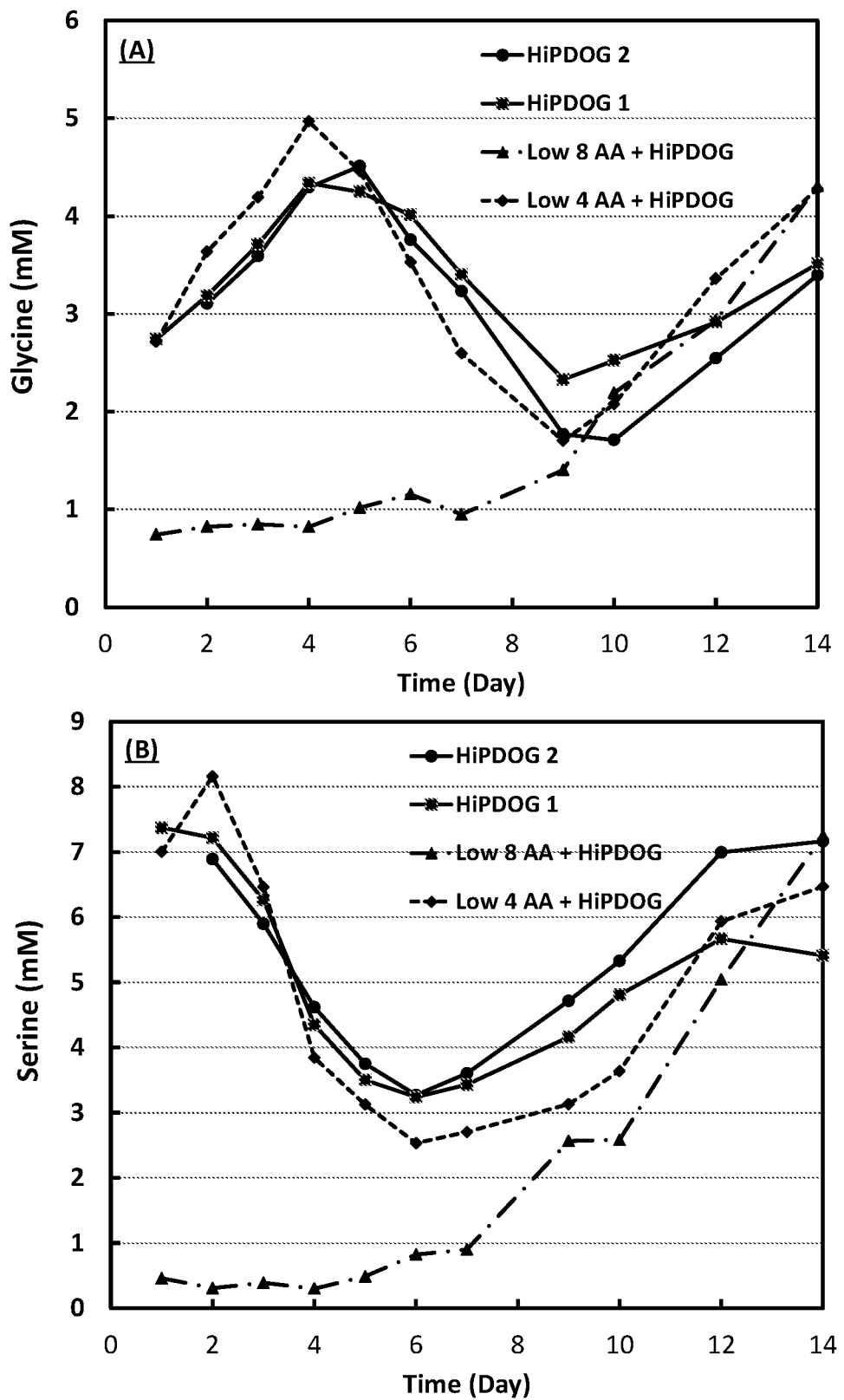

FIG. 10A shows the viable cell densities of GS-CHO cells during a cell culture process using different conditions disclosed in Example 5 (HiPDOG1 (closed squares), HiPDOG2 (closed circles), Low 4AA+HipDOG (closed diamonds), Low 8AA+HipDOG (closed triangles)).

FIG. 10B shows the culture titer (IgG) at different days in a cell culture process using GS-CHO cells and different cell culture conditions disclosed in Example 5 ((HiPDOG1 (closed squares), HiPDOG2 (closed circles), Low 4AA+HipDOG (closed diamonds), Low 8AA+HipDOG (closed triangles)).

FIGS. 11, 12, 13 and 14 show the concentrations of tyrosine (FIG. 11A), methionine (FIG. 11B), phenylalanine (FIG. 12A), tryptophan (FIG. 12B), leucine (FIG. 13A), threonine (FIG. 13B), glycine (FIG. 14A) and serine (FIG. 14B) during the cell culture of GS-CHO cells using conditions disclosed in Example 5 ((HiPDOG1 (closed squares), (HiPDOG2 (closed circles), Low 4AA+HipDOG (closed diamonds), Low 8AA+HipDOG (closed triangles)).

Figure 15:
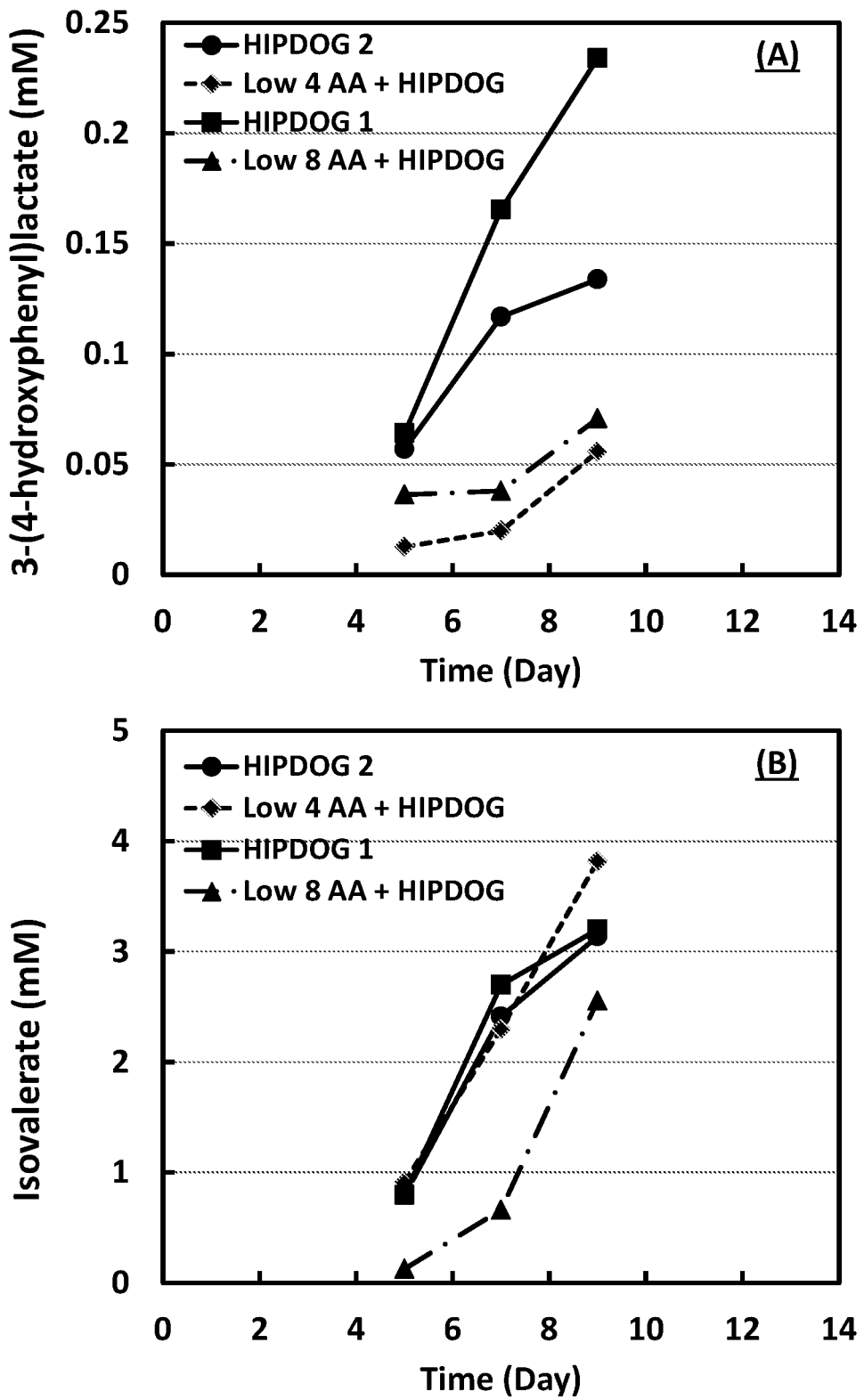
Figure 16:
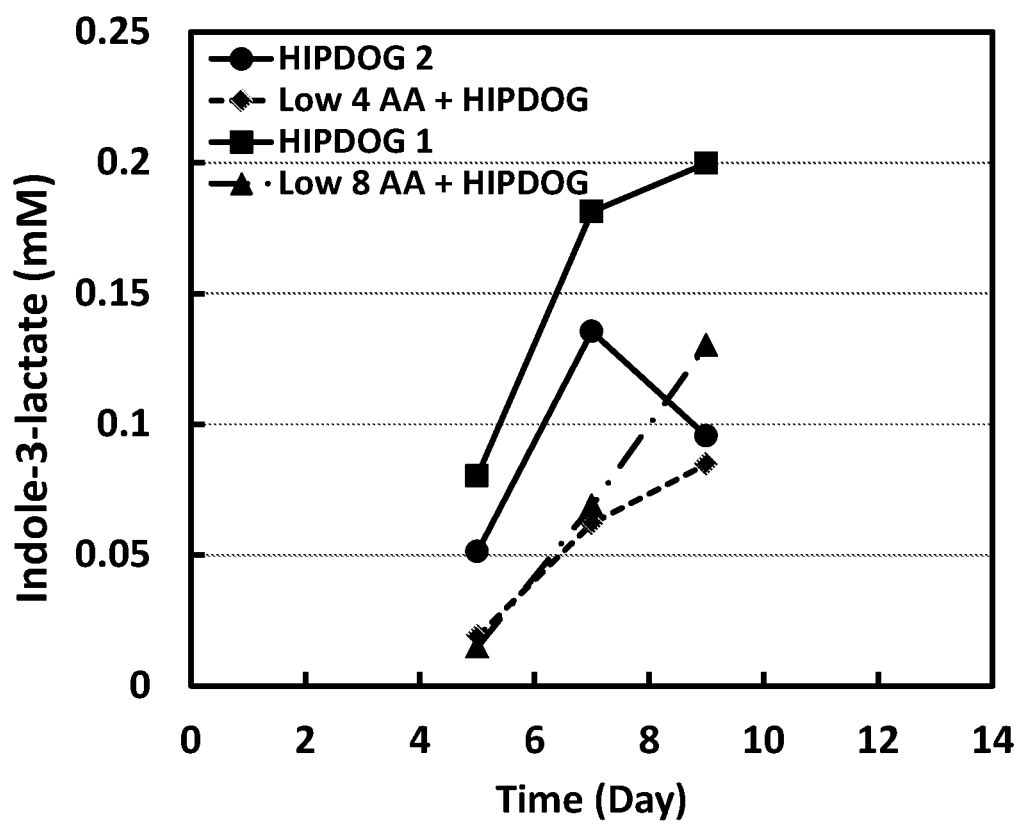

FIGS. 15 and 16 show the concentration of 3-(4-hydroxyphenyl)lactate (FIG. 15A), isovalerate (FIG. 15B) and indole-3-lactate (FIG. 16) at day 5, day 7 and day 9 of the cell culture of GS-CHO cells using conditions disclosed in Example 5 ((HiPDOG1 (closed squares), HiPDOG2 (closed circles), Low 4AA+HipDOG (closed diamonds), Low 8AA+HipDOG (closed triangles)).

Figure 17:
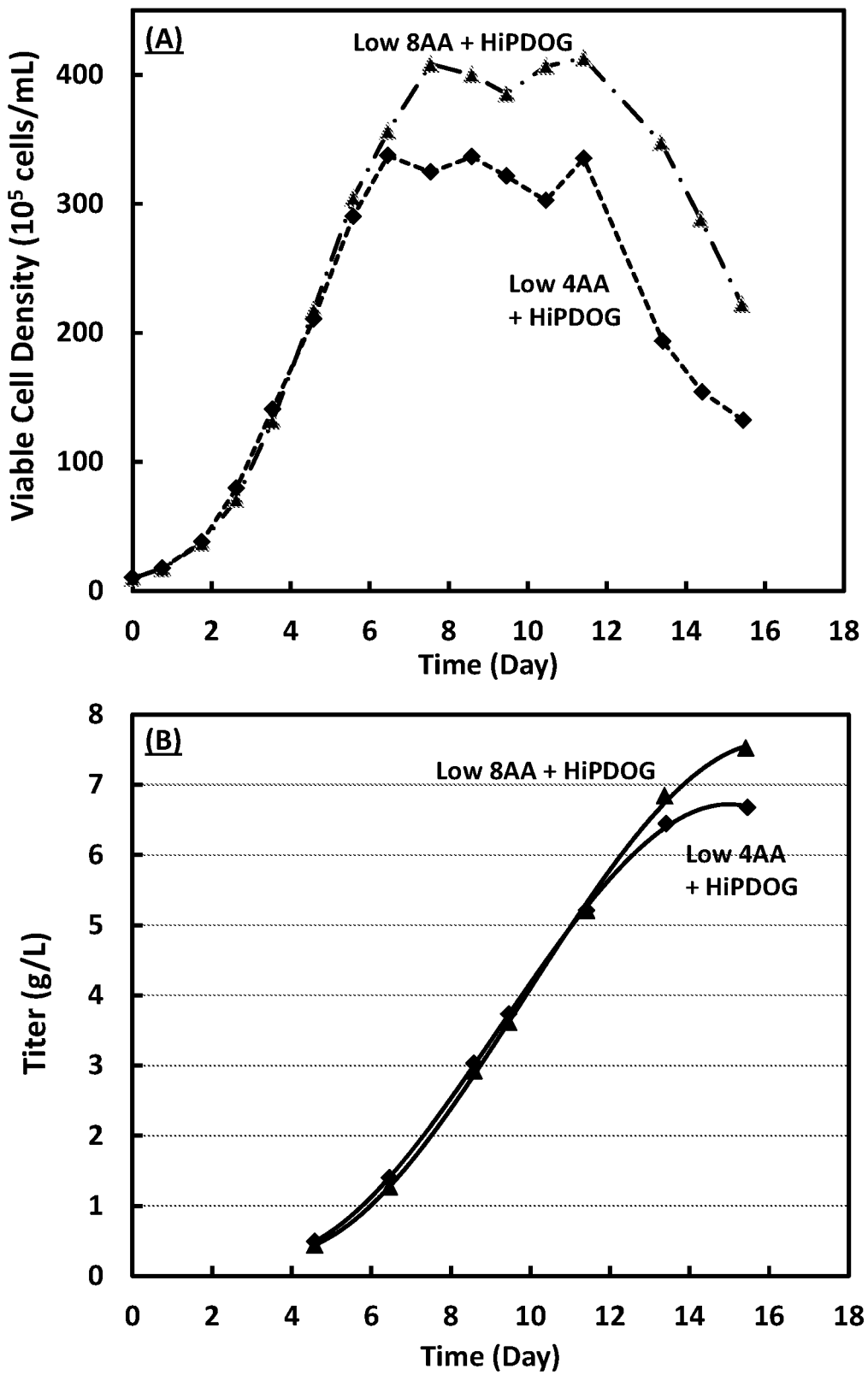

FIG. 17 shows the viable cell densities of GS-CHO cells and culture titer (IgG) during a cell culture process using conditions disclosed in Example 5 ((Low 4AA+HiPDOG (closed diamonds), Low 8AA+HipDOG (closed triangles)).

Figure 18:
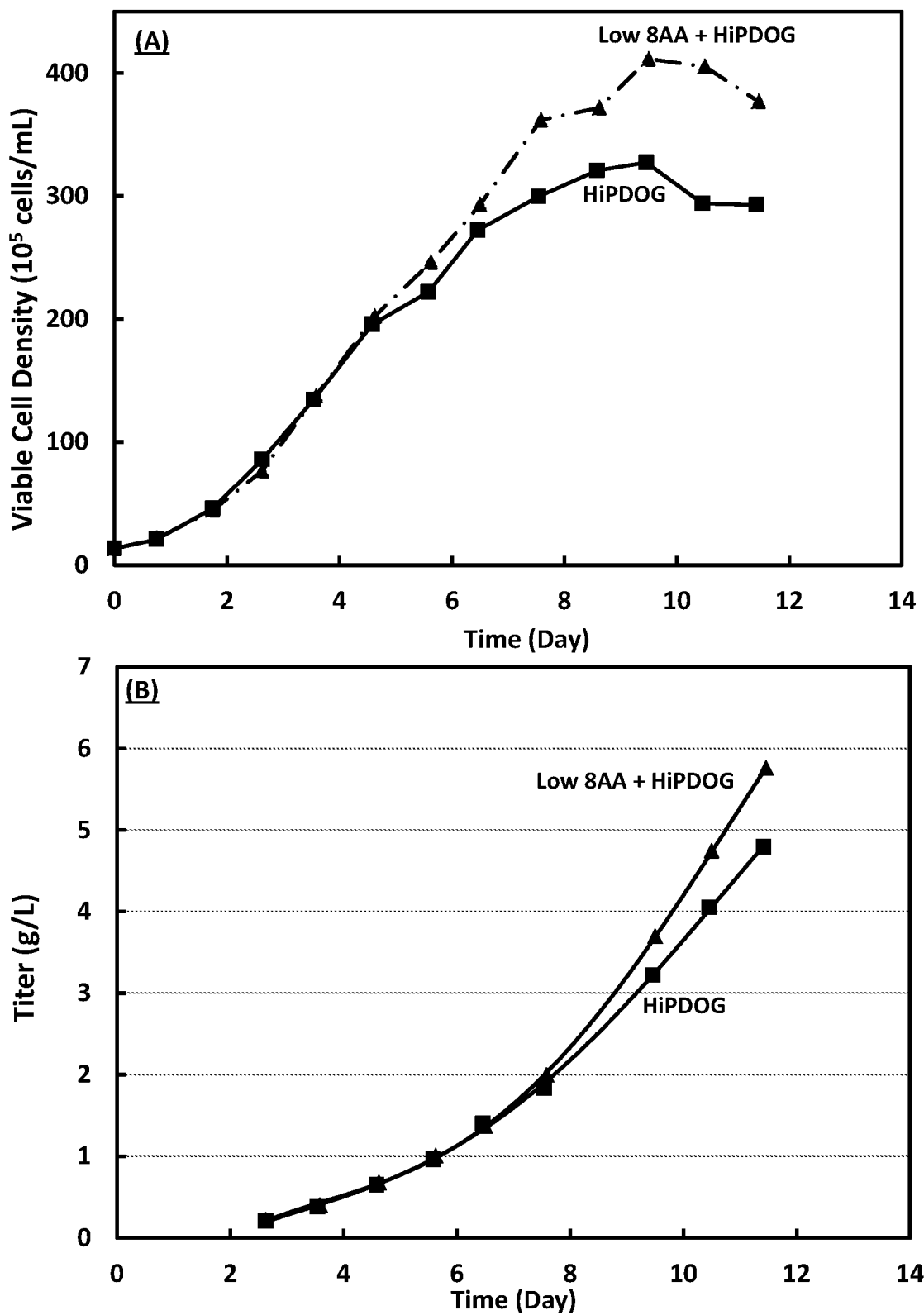

FIGS. 18A and 18B show the viable cell densities of GS-CHO cells and culture titer (IgG) during a cell culture process using conditions disclosed in Example 6 ((HiPDOG (closed squares), Low 8AA+HipDOG (closed triangles)).

Figure 19:
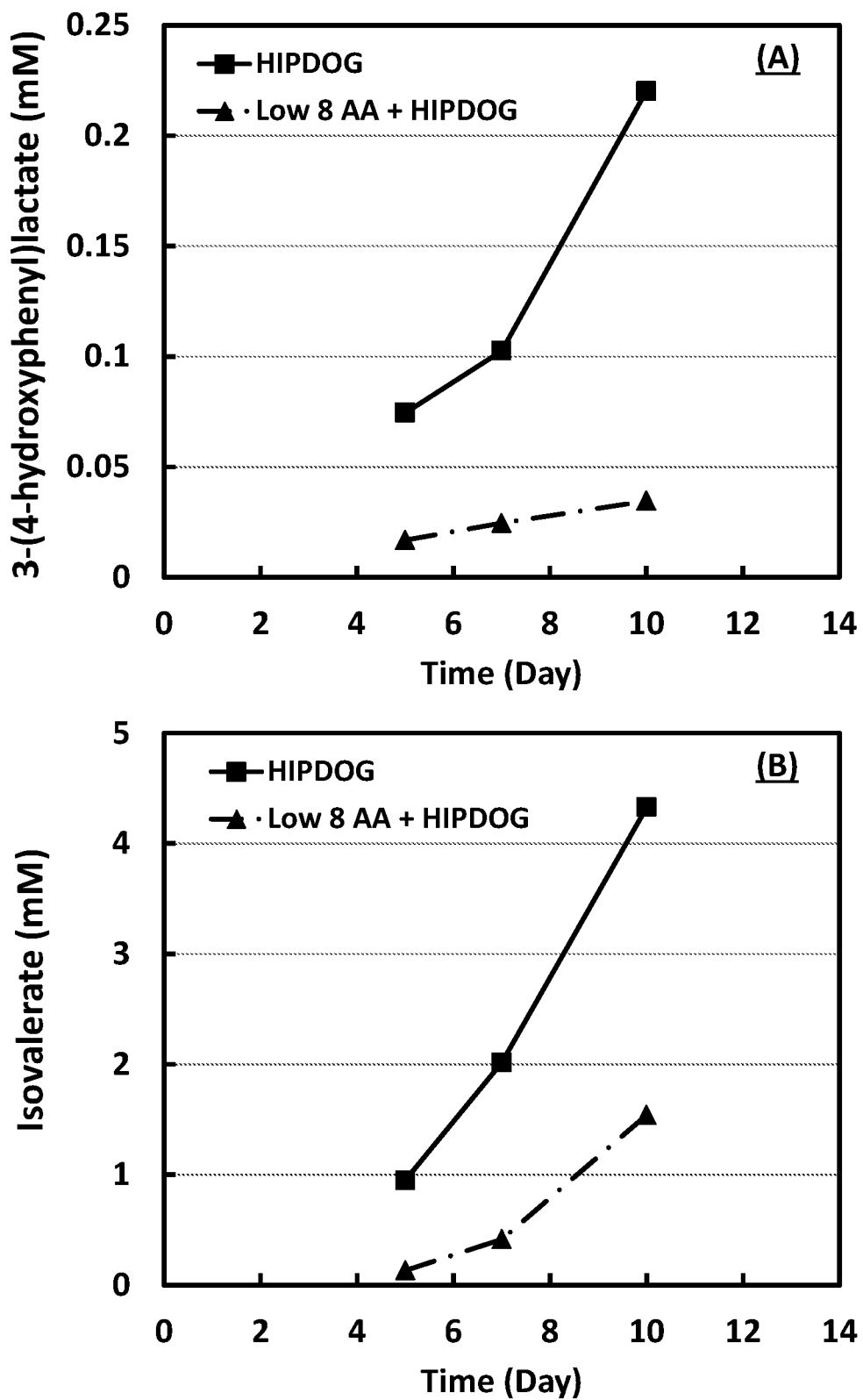
Figure 20:
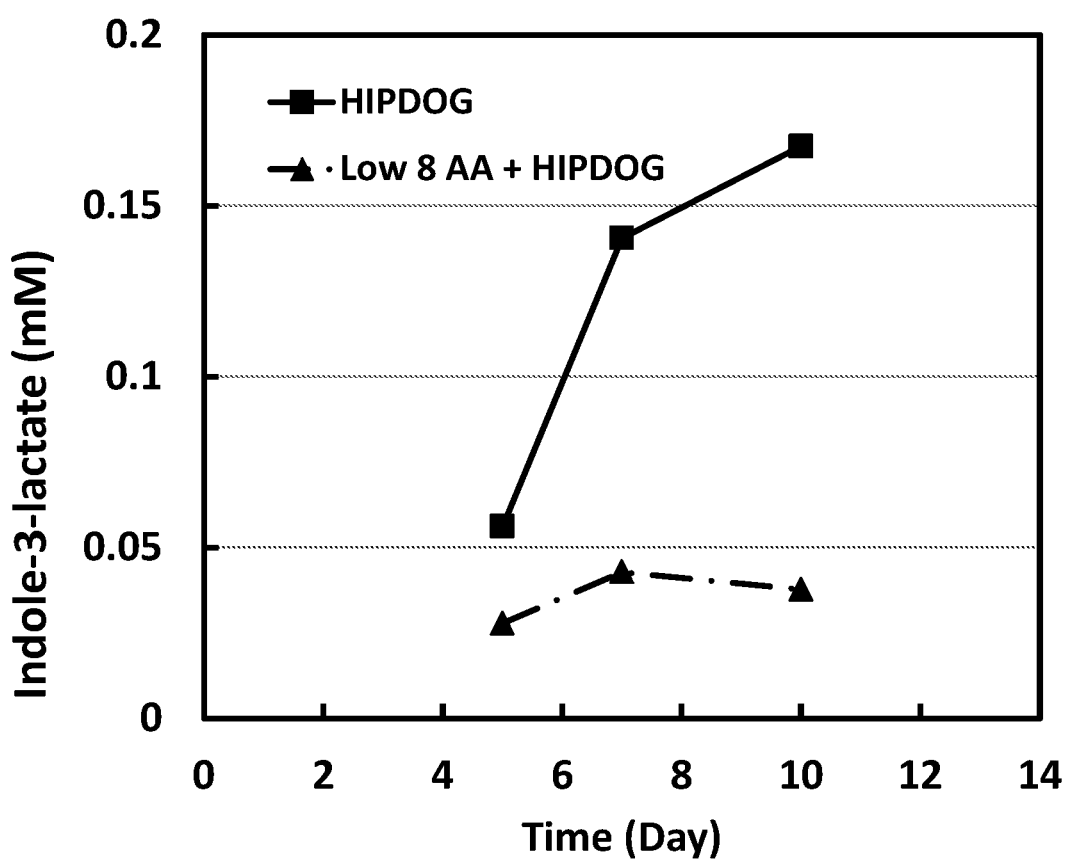

FIGS. 19 and 20 show the concentration of 3-(4-hydroxyphenyl)lactate (FIG. 19A), isovalerate (FIG. 19B) and indole-3-lactate (FIG. 20) at day 5, day 7 and day 10 of the cell culture of GS-CHO cells using conditions disclosed in Example 6 ((HiPDOG (closed squares), Low 8AA+HipDOG (closed triangles)).

FIGS. 21A and 21B show the viable cell densities of GS-CHO cells and culture titer (IgG) during a cell culture process using different conditions disclosed in Example 6 ((HiPDOG (closed squares), Low 4AA+HipDOG (closed diamonds)).

Figure 22:
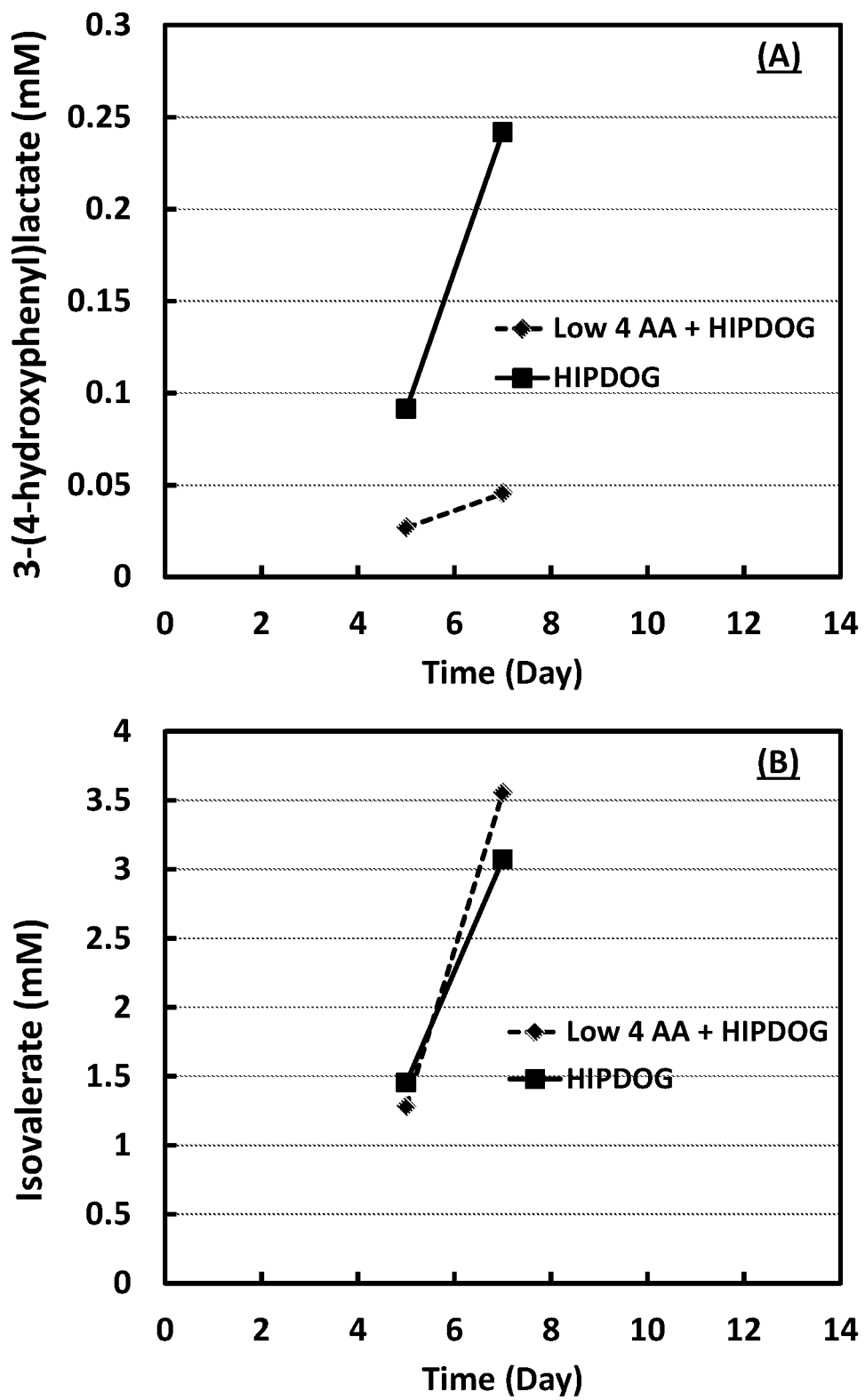
Figure 23:
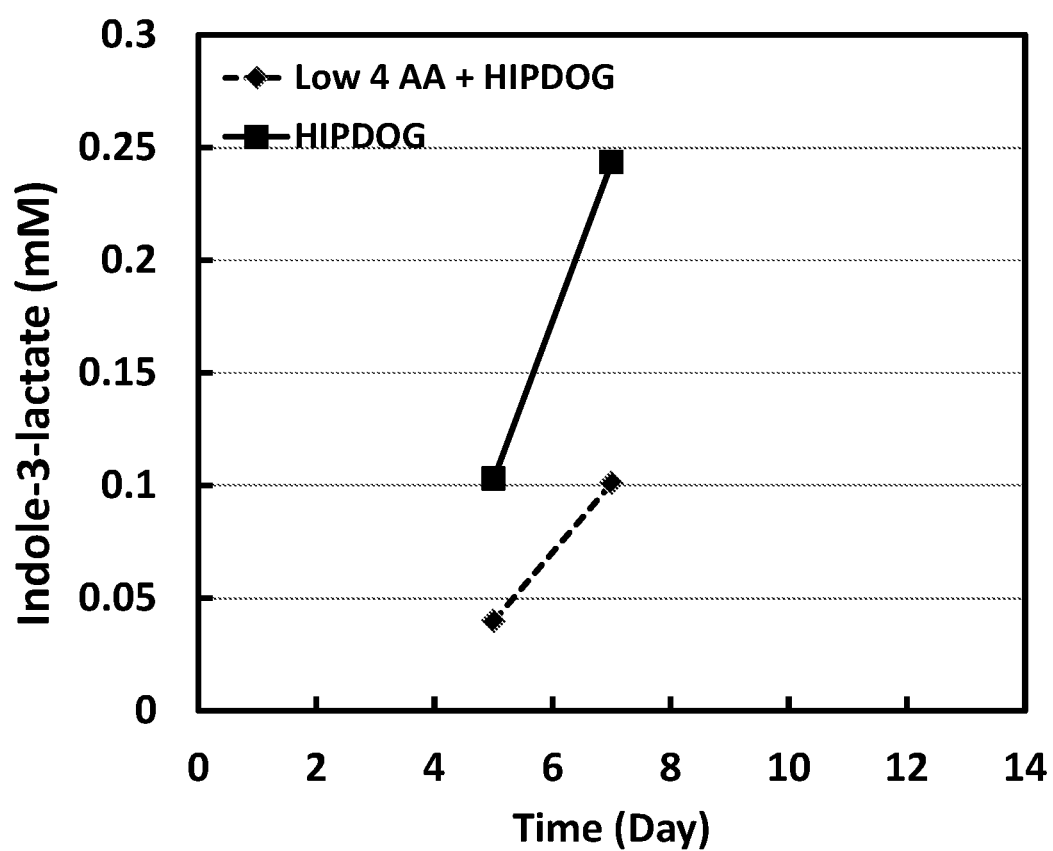

FIGS. 22 and 23 show the concentration of 3-(4-hydroxyphenyl)lactate (FIG. 22A), isovalerate (FIG. 22B) and indole-3-lactate (FIG. 23) at day 5 and day 7 of the cell culture of GS-CHO cells using conditions disclosed in Example 6 ((HiPDOG (closed squares), Low 4AA+HipDOG (closed diamonds)).

DETAILED DESCRIPTION

The present invention provides methods and media for cell culture. The present invention provides cell culture methods where the concentration of at least one metabolite selected from 3-(4-hydroxyphenyl)lactate, 4-hydroxyphenylpyruvate, phenyllactate, indolelactate, indolecarboxylic acid, homocysteine, 2-hydroxybutyric acid, isovalerate and formate, and/or at least one amino acid selected from phenylalanine, tyrosine, tryptophan, methionine, leucine, serine, threonine and glycine is maintained at low levels in the cell culture medium. The inventors have unexpectedly discovered that, in cell culture, and in particular in high density cell culture, such as for example fed-batch cell culture aiming at producing high amount of a recombinant protein of interest, the growth of cells were inhibited by the accumulation of metabolites such as 3-(4-hydroxyphenyl) lactate, 4-hydroxyphenylpyruvate, phenyllactate, indolelactate, indolecarboxylic acid, homocysteine, 2-hydroxybutyric acid, isovalerate and formate in the cell culture medium. The inhibitory effect of these metabolites can be limited by maintaining their concentration in the cell culture medium below levels where they inhibit cell growth.

Methods Comprising Controlling the Metabolite Concentration in the Cell Culture Medium at Low Levels In some embodiments, the invention relates to a method of cell culture comprising
(i) providing cells in a cell culture medium to start a cell culture process, and,
(ii) maintaining at least one metabolite selected from 3-(4-hydroxyphenyl)lactate, 4-hydroxyphenylpyruvate, phenyllactate, indolelactate, indolecarboxylic acid, homocysteine, 2-hydroxybutyric acid, isovalerate and formate below a concentration C1 in the cell culture medium, wherein C1 is 3 mM.

In some embodiments, C1 is 2 mM, 1.5 mM, 1 mM, 0.9 mM, 0.8 mM, 0.7 mM, 0.6 mM, 0.5 mM, 0.4 mM, 0.3 mM, 0.2 mM or 0.1 mM. In some embodiments, C1 is 1 mM. In some embodiments, C1 is 0.5 mM.

Methods Comprising Measuring the Metabolite Concentration in the Cell Culture Medium In some embodiments, step (ii) comprises the step of measuring the concentration of said at least one metabolite. The concentration of metabolite can be measured by any method known to the skilled person, including off line and on line measurement methods.

The concentration of metabolites can be measured once or several times during the cell culture. In some embodiments, the metabolite concentration is measured continuously, intermittently, every 30 min, every hour, every two hours, twice a day, daily, or every two days. In a preferred embodiment the concentration of metabolite is measured daily.

An off line measurement method as used herein refers to a method where the measurement of a parameter such as a concentration is not automated and integrated to the cell culture method. For example, a measurement method where a sample is manually taken from the cell culture medium so that a specific concentration can be measured in said sample is considered as an off line measurement method.

Online measurement methods as used herein refer to methods where the measurement of a parameter, such as a concentration, is automated and integrated to the cell culture method. For example, a method using the Raman spectroscopy as disclosed in Example 7 is an on-line measurement method. Alternatively, the use of High Performance Liquid Chromatography (HPLC) or Ultra Performance Liquid Chromatography (UPLC) based technology with an autosampler that draws samples from reactor and transfers them to the equipment in a programmed manner is an online measurement method.

The concentration of metabolites can be measured by any method known to the skilled person. Preferred methods to measure the concentration of metabolites in online or offline methods include for example Liquid Chromatography such as High-Performance Liquid Chromatography (HPLC), Ultra Performance Liquid Chromatography (UPLC) or Liquid Chromatography-Mass Spectrometry (LCMS), Nuclear Magnetic Resonance (NMR) or Gas Chromatography-Mass Spectrometry (GCMS).

In some embodiments, the concentration of metabolite is measured off line by taking a sample of the cell culture medium and measuring the concentration of said at least one metabolite in said sample. In some embodiments, the concentration of metabolites is measured as disclosed in Example 2. A preferred method to measure the concentration of metabolites in an offline method is LCMS.

In some embodiments, the concentration of metabolite is measured on-line. In some embodiments, the concentration of metabolite is measured online using Raman spectroscopy. In some embodiments, the concentration of metabolite is measured on-line using Raman spectroscopy as disclosed in Example 7. In some embodiments, the concentration of metabolite is measured online using HPLC or UPLC based technology with an auto-sampler that draws samples from reactor and transfers them to the equipment in a programmed manner.

In some embodiments, when the measured concentration is above a predefined value, the concentration of precursor of said at least one metabolite in the cell culture medium is decreased. Said predefined value is selected so that the decrease of concentration of said precursor prevents the concentration of metabolite to rise above C1. The predefined value can be equal C1 or can be a percentage of C1. In some embodiments the percentage is 50, 55, 60, 65, 70, 75, 80, 85, 90 or 95% of C1. In some embodiments the percentage is 80% of C1.

In some embodiments, when the measured concentration of 3-(4-hydroxyphenyl)lactate, 4-hydroxyphenylpyruvate and/or phenyllactate is above said predefined value, the concentration of phenylalanine is decreased in the cell culture medium.

In some embodiments, when the measured concentration of 3-(4-hydroxyphenyl)lactate and/or 4-hydroxyphenylpyruvate is above said predefined value, the concentration of tyrosine is decreased in the cell culture medium.

In some embodiments, when the measured concentration of 3-(4-hydroxyphenyl)lactate, 4-hydroxyphenylpyruvate and/or phenyllactate is above said predefined value, the concentrations of tyrosine and phenylalanine are decreased in the cell culture medium.

In some embodiments, when the measured concentration of indolelactate and/or indolecarboxylic acid is above said predefined value, the concentration of tryptophan is decreased in the cell culture medium.

In some embodiments, when the measured concentration of homocysteine and/or 2-hydroxybutyric acid is above said predefined value, the concentration of methionine is decreased in the cell culture medium.

In some embodiments, when the measured concentration of isovalerate is above said predefined value, the concentration of leucine is decreased in the cell culture medium.

In some embodiments, when the measured concentration of formate is above said predefined value, the concentration of serine, threonine and/or glycine is decreased in the cell culture medium.

In some embodiments, when the measured concentration of formate is above said predefined value, the concentration of serine is decreased in the cell culture medium.

In some embodiments, when the measured concentration of formate is above said predefined value, the concentration of threonine is decreased in the cell culture medium.

In some embodiments, when the measured concentration of formate is above said predefined value, the concentration of glycine is decreased in the cell culture medium.

The concentration of precursor in the cell culture medium can be decreased by reducing the amount of precursor provided to the cells, for example by reducing the concentration of said precursor in the feed medium, reducing the feed rate, or reducing the number or volume of feeds. For example, the feed medium can be replaced by a feed medium comprising a lower concentration of precursor.

In some embodiments of the above disclosed methods, step (ii) comprises maintaining 1, 2, 3, 4, 5, 6, 7, 8 or 9 of 3-(4-hydroxyphenyl)lactate, 4-hydroxyphenylpyruvate, phenyllactate, indolelactate, indolecarboxylic acid, homocysteine, 2-hydroxybutyric acid, isovalerate and formate below C1 in the cell culture medium.

In some embodiments of the above disclosed methods, step (ii) comprises maintaining 1, 2, 3, 4, 5, 6, or 7 of 3-(4-hydroxyphenyl)lactate, 4-hydroxyphenylpyruvate, phenyllactate, indolelactate, indolecarboxylic acid, homocysteine and 2-hydroxybutyric acid below C1 in the cell culture medium.

In some embodiments of the above disclosed methods, step (ii) comprises maintaining 3-(4-hydroxyphenyl)lactate, 4-hydroxyphenylpyruvate and phenyllactate below C1 in the cell culture medium.

In some embodiments of the above disclosed methods, step (ii) comprises maintaining indolelactate and indolecarboxylic acid below C1 in the cell culture medium.

In some embodiments of the above disclosed methods, step (ii) comprises maintaining homocysteine and 2-hydroxybutyric acid below C1 in the cell culture medium.

In some embodiments of the above disclosed methods, step (ii) comprises maintaining isovalerate below C1 in the cell culture medium.

In some embodiments of the above disclosed methods, step (ii) comprises maintaining formate below C1 in the cell culture medium.

In some embodiments of the above disclosed methods, step (ii) comprises maintaining isovalerate and 4-hydroxyphenylpyruvate below C1 in the cell culture medium.

In some embodiments of the above disclosed methods, step (ii) comprises maintaining 3-(4-hydroxyphenyl)lactate, 4-hydroxyphenylpyruvate, phenyllactate, indolelactate, indolecarboxylic acid, homocysteine, 2-hydroxybutyric acid isovalerate and formate below C1 in the cell culture medium.

In some embodiments of the above disclosed methods, in step (ii), the concentration of 3-(4-hydroxyphenyl)lactate is maintained below 0.5 mM, 0.4 mM, 0.3 mM, 0.2 mM, or 0.1 mM.

In some embodiments of the above disclosed methods, in step (ii), the concentration of 3-(4-hydroxyphenyl)lactate is maintained below 0.3 mM.

In some embodiments of the above disclosed methods, in step (ii), the concentration of 3-(4-hydroxyphenyl)lactate is maintained below 0.1 mM.

In some embodiments of the above disclosed methods, in step (ii), the concentration of 4-hydroxyphenylpyruvate is maintained below 0.1 mM, 0.08 mM, 0.06 mM, 0.05 mM, 0.04 mM, 0.03 mM or 0.02 mM.

In some embodiments of the above disclosed methods, in step (ii), the concentration of 4-hydroxyphenylpyruvate is maintained below 0.05 mM.

In some embodiments of the above disclosed methods, in step (ii), the concentration of 4-hydroxyphenylpyruvate is maintained below 0.02 mM.

In some embodiments of the above disclosed methods, in step (ii), the concentration of phenyllactate is maintained below 0.5 mM, 0.4 mM, 0.3 mM, 0.2 mM, or 0.1 mM.

In some embodiments of the above disclosed methods, in step (ii), the concentration of phenyllactate is maintained below 0.2 mM.

In some embodiments of the above disclosed methods, in step (ii), the concentration of phenyllactate is maintained below 0.1 mM.

In some embodiments of the above disclosed methods, in step (ii), the concentration of indolelactate is maintained below 3 mM, 2 mM, 1 mM, 0.5 mM, 0.3 mM or 0.1 mM.

In some embodiments of the above disclosed methods, in step (ii), the concentration of indolelactate is maintained below 1 mM.

In some embodiments of the above disclosed methods, in step (ii), the concentration of indolelactate is maintained below 0.3 mM.

In some embodiments of the above disclosed methods, in step (ii), the concentration of indolelactate is maintained below 0.1 mM.

In some embodiments of the above disclosed methods, in step (ii), the concentration of indolecarboxylic acid is maintained below 1 mM, 0.8 mM, 0.6 mM, 0.4 mM or 0.2 mM.

In some embodiments of the above disclosed methods, in step (ii), the concentration of indolecarboxylic acid is maintained below 0.5 mM.

In some embodiments of the above disclosed methods, in step (ii), the concentration of indolecarboxylic acid is maintained below 0.2 mM.

In some embodiments of the above disclosed methods, in step (ii), the concentration of homocysteine is maintained below 0.5 mM, 0.4 mM, 0.3 mM, 0.2 mM, or 0.1 mM.

In some embodiments of the above disclosed methods, in step (ii), the concentration of homocysteine is maintained below 0.3 mM.

In some embodiments of the above disclosed methods, in step (ii), the concentration of homocysteine is maintained below 0.1 mM.

In some embodiments of the above disclosed methods, in step (ii), the concentration of 2-hydroxybutyric acid is maintained below 1 mM, 0.8 mM, 0.6 mM, 0.4 mM or 0.2 mM.

In some embodiments of the above disclosed methods, in step (ii), the concentration of 2-hydroxybutyric acid is maintained below 0.5 mM.

In some embodiments of the above disclosed methods, in step (ii), the concentration of 2-hydroxybutyric acid is maintained below 0.2 mM.

In some embodiments of the above disclosed methods, in step (ii), the concentration of isovalerate is maintained below 2 mM, 1 mM, 0.8 mM, 0.6 mM, 0.4 mM or 0.2 mM.

In some embodiments of the above disclosed methods, in step (ii), the concentration of isovalerate is maintained below 1 mM.

In some embodiments of the above disclosed methods, in step (ii), the concentration of isovalerate is maintained below 0.5 mM.

In some embodiments of the above disclosed methods, in step (ii), the concentration of formate is maintained below 4 mM, 3 mM, 2 mM, 1 mM, 0.5 mM or 0.2 mM.

In some embodiments of the above disclosed methods, in step (ii), the concentration of formate is maintained below 3 mM.

In some embodiments of the above disclosed methods, in step (ii), the concentration of formate is maintained below 1 mM.

Methods Comprising Controlling the Amino Acid Concentration in the Cell Culture Medium at Low Levels In some embodiments, the invention relates to a method of cell culture comprising
(i) providing cells in a cell culture medium to start a cell culture process, and,
(ii) maintaining at least one amino acid selected from phenylalanine, tyrosine, tryptophan, methionine, leucine, serine, threonine and glycine below a concentration C2 in the cell culture medium, wherein C2 is 2 mM.

In some embodiments, said concentration is maintained between 0.1 mM and C2, 0.2 mM and C2, 0.3 mM and C2, 0.4 mM and C2, or 0.5 mM and C2. In some embodiments, said concentration is maintained between 0.5 mM and C2.

In some embodiments, C2 is 2 mM, 1.5 mM, 1 mM, 0.9 mM, 0.8 mM, 0.7 mM, 0.6 mM. In some embodiments, C2 is 1 mM.

Methods Comprising Measuring the Amino Acid Concentration in the Cell Culture Medium In some embodiments, step (ii) comprises the step of measuring the concentration of said at least one amino acid. The concentration of amino acid can be measured by any method known to the skilled person, including off line and on line measurement methods.

The concentration of amino acids can be measured once or several times during the cell culture. In some embodiments, the amino acid concentration is measured continuously, intermittently, every 30 min, every hour, every two hours, twice a day, daily, or every two days. In a preferred embodiment, the concentration of amino acid is measured daily.

The concentration of amino acid can be measured by any method known to the skilled person. Preferred methods to measure the concentration of amino acids in online or offline methods include for example Liquid Chromatography such as HPLC, UPLC or LCMS, NMR or GCMS.

In some embodiments, the concentration of amino acid is measured off line by taking a sample of the cell culture medium and measuring the concentration of said at least one amino acid in said sample. In some embodiments, the concentration of amino acid is measured as disclosed in Example 4. A preferred method to measure the concentration of amino acids in an off line method is UPLC.

In some embodiments, the concentration of amino acid is measured online. In some embodiments, the concentration of amino acid is measured on-line using Raman spectroscopy. In some embodiments, the concentration of amino acid is measured on-line using Raman spectroscopy as disclosed in Example 7. In some embodiments, the concentration of amino acid is measured online using HPLC or UPLC based technology with an auto-sampler that draws sample from reactor and transfers to the equipment in a programmed manner.

In some embodiments, when the measured concentration is above a predefined value, the concentration of said at least one amino acid in the cell culture medium is decreased. The predefined value can be equal C2 or can be a percentage of C2. In some embodiments the percentage is 50, 55, 60, 65, 70, 75, 80, 85, 90 or 95% of C2. In some embodiments the percentage is 80% of C2.

The concentration of amino acid in the cell culture medium can be decreased by reducing the amount of amino acid provided to the cells, for example by reducing the concentration of said amino acid in the feed medium, reducing the feed rate, or reducing the number or volume of feeds. For example, the feed medium can be replaced by a feed medium comprising a lower concentration of amino acid.

Concentration of Phenylalanine, Tyrosine, Tryptophan Methionine, Leucine, Serine, Threonine and Glycine in the Cell Culture Medium In some embodiments of any of the above disclosed methods, in step (ii), the concentration of phenylalanine is maintained below 2 mM in the cell culture medium. In a preferred embodiment, the concentration of phenylalanine is maintained between 0.1 and 2 mM in the cell culture medium. In a preferred embodiment, the concentration of phenylalanine is maintained between 0.1 and 1 mM in the cell culture medium. In a preferred embodiment, the concentration of phenylalanine is maintained between 0.2 and 1 mM in the cell culture medium. In a preferred embodiment, the concentration of phenylalanine is maintained between 0.5 and 1 mM in the cell culture medium.

In some embodiments of any of the above disclosed methods, in step (ii), the concentration of tyrosine is maintained below 2 mM in the cell culture medium. In a preferred embodiment, the concentration of tyrosine is maintained between 0.1 and 2 mM in the cell culture medium. In a preferred embodiment, the concentration of tyrosine is maintained between 0.1 and 1 mM in the cell culture medium. In a preferred embodiment, the concentration of tyrosine is maintained between 0.2 and 1 mM in the cell culture medium. In a preferred embodiment, the concentration of tyrosine is maintained between 0.5 and 1 mM in the cell culture medium.

In some embodiments of any of the above disclosed methods, in step (ii), the concentration of tryptophan is maintained below 2 mM in the cell culture medium. In a preferred embodiment, the concentration of tryptophan is maintained between 0.1 and 2 mM in the cell culture medium. In a preferred embodiment, the concentration of tryptophan is maintained between 0.1 and 1 mM in the cell culture medium. In a preferred embodiment, the concentration of tryptophan is maintained between 0.2 and 1 mM in the cell culture medium. In a preferred embodiment, the concentration of tryptophan is maintained between 0.5 and 1 mM in the cell culture medium.

In some embodiments of any of the above disclosed methods, in step (ii), the concentration of methionine is maintained below 2 mM in the cell culture medium. In a preferred embodiment, the concentration of methionine is maintained between 0.1 and 2 mM in the cell culture medium. In a preferred embodiment, the concentration of methionine is maintained between 0.1 and 1 mM in the cell culture medium. In a preferred embodiment, the concentration of methionine is maintained between 0.2 and 1 mM in the cell culture medium. In a preferred embodiment, the concentration of methionine is maintained between 0.5 and 1 mM in the cell culture medium.

In some embodiments of any of the above disclosed methods, in step (ii), the concentration of leucine is maintained below 2 mM in the cell culture medium. In a preferred embodiment, the concentration of leucine is maintained between 0.1 and 2 mM in the cell culture medium. In a preferred embodiment, the concentration of leucine is maintained between 0.1 and 1 mM in the cell culture medium. In a preferred embodiment, the concentration of leucine is maintained between 0.2 and 1 mM in the cell culture medium. In a preferred embodiment, the concentration of leucine is maintained between 0.5 and 1 mM in the cell culture medium.

In some embodiments of any of the above disclosed methods, in step (ii), the concentration of serine is maintained below 2 mM in the cell culture medium. In a preferred embodiment, the concentration of serine is maintained between 0.1 and 2 mM in the cell culture medium. In a preferred embodiment, the concentration of serine is maintained between 0.1 and 1 mM in the cell culture medium. In a preferred embodiment, the concentration of serine is maintained between 0.2 and 1 mM in the cell culture medium. In a preferred embodiment, the concentration of serine is maintained between 0.5 and 1 mM in the cell culture medium.

In some embodiments of any of the above disclosed methods, in step (ii), the concentration of threonine is maintained below 2 mM in the cell culture medium. In a preferred embodiment, the concentration of threonine is maintained between 0.1 and 2 mM in the cell culture medium. In a preferred embodiment, the concentration of threonine is maintained between 0.1 and 1 mM in the cell culture medium. In a preferred embodiment, the concentration of threonine is maintained between 0.2 and 1 mM in the cell culture medium. In a preferred embodiment, the concentration of threonine is maintained between 0.5 and 1 mM in the cell culture medium.

In some embodiments of any of the above disclosed methods, in step (ii), the concentration of glycine is maintained below 2 mM in the cell culture medium. In a preferred embodiment, the concentration of glycine is maintained between 0.1 and 2 mM in the cell culture medium. In a preferred embodiment, the concentration of glycine is maintained between 0.1 and 1 mM in the cell culture medium. In a preferred embodiment, the concentration of glycine is maintained between 0.2 and 1 mM in the cell culture medium. In a preferred embodiment, the concentration of glycine is maintained between 0.5 and 1 mM in the cell culture medium.

In a preferred embodiment of any of the above disclosed methods, in step (ii), the concentration of tyrosine, phenylalanine and leucine is maintained below 2 mM, preferably between 0.1 and 2 mM, between 0.1 and 1 mM, between 0.2 and 1 mM or between 0.5 and 1 mM in the cell culture medium.

In some embodiments, the cell culture medium comprises 1, 2, 3, 4, 5, 6, 7, 8, 9, 10, 11, 12 or 13 of glycine, valine, leucine, isoleucine, proline, serine, threonine, lysine, arginine, histidine, aspartate, glutamate and asparagine at a concentration above 1 mM, 1.5 mM, 2 mM, 3 mM or 5 mM.

In some embodiments, the cell culture medium comprises one of glycine, valine, leucine, isoleucine, proline, serine, threonine, lysine, arginine, histidine, aspartate, glutamate and asparagine at a concentration above 2 mM.

In some embodiments, the cell culture medium comprises one of glycine, valine, leucine, isoleucine, proline, serine, threonine, lysine, arginine, histidine, aspartate, glutamate and asparagine at a concentration above 5 mM.

In some embodiments, the cell culture medium comprises 1, 2, 3, 4, 5, 6, 7, 8 or 9, of valine, isoleucine, proline, lysine, arginine, histidine, aspartate, glutamate and asparagine at a concentration above 1 mM, 1.5 mM, 2 mM, 3 mM or 5 mM.

In some embodiments, the cell culture medium comprises one of valine, isoleucine, proline, lysine, arginine, histidine, aspartate, glutamate and asparagine at a concentration above 2 mM.

In some embodiments, the cell culture medium comprises one of valine, isoleucine, proline, lysine, arginine, histidine, aspartate, glutamate and asparagine at a concentration above 5 mM.

Concentration of Lactate and Ammonia

In some embodiments of any of the above disclosed methods, other metabolites inhibiting growth of cells, such as lactate and ammonia are also maintained at low levels in the cell culture medium. Methods to keep lactate and ammonia at low levels are known to the skilled person.

For example, lactate can be kept at low levels in cell culture by using methods disclosed in WO2004104186, Gagnon et al, Biotechnology and Bioengineering, Vol. 108, No. 6, June, 2011 (Gagnon et Al) or WO2004048556.

Various other strategies can be employed to restrict lactate production and/or induce lactate consumption. These include culturing cells under slightly reduced pH (6.7-7.0), culturing cells at low glucose concentrations by using alternative carbon sources including but not limited to fructose (Wlaschin & Hu, 2007) and galactose (Altamirano et al, 2006), using a cell line that has reduced protein levels of glycolytic enzymes including but not limited to hexose transporter or lactate dehydrogenase (Kim & Lee, 2007a), employing a cell line with suppressed cellular protein levels of both lactate dehydrogenase and pyruvate dehydrogenase kinase (Zhou et al, 2011), or cell line with over-expression of pyruvate carboxylase enzyme (Kim & Lee, 2007b), or with the use of inhibitors (small molecule or protein based) for signaling pathways (such as AKT (Mulukutla et al, 2012), mTOR (Duvel et al, 2010; Lee & Lee, 2012), HIF1a) that regulate the activity of energy metabolism pathways (glycolysis, TCA cycle, and redox pathway).

In a preferred embodiment, lactate is maintained at low levels by using the high-end pH-controlled delivery of glucose (HIPDOG process) disclosed in Gagnon et al.

In some embodiments of any of the above disclosed methods lactate is maintained at low levels in the cell culture medium. In a preferred embodiment, concentration of lactate in the cell culture medium is maintained below 90 mM. In a preferred embodiment, the concentration of lactate in the cell culture medium is maintained below 70 mM. In a preferred embodiment, the concentration of lactate in the cell culture medium is maintained below 50 mM. In a preferred embodiment, the concentration of lactate in the cell culture medium is maintained below 40 mM. In a preferred embodiment, lactate is maintained at low levels by controlling the amount of glucose provided to the cell culture. In a preferred embodiment, lactate is maintained at low levels by using the HIPDOG process. In a preferred embodiment, a pH sensor is used to monitor pH of the cell culture, and, in response to a rise above a predetermined pH value, glucose is fed to the cell culture. In a preferred embodiment, the predetermined pH value is approximately 7.

Ammonia can be kept at low levels in cell culture by any method known to the skilled person such as for example the methods disclosed in Butler et Al, *Cytotechnology* 15: 87-94, 1994 or Hong et Al, Appl Microbiol Biotechnol (2010) 88:869-876. Alternatively, ammonia can be kept at low levels by using a glutamine synthetase (GS) expression system. Such systems are commercially available (Lonza) and can be used to generate recombinant cell lines. Cell lines using GS expression system demonstrate the gain of function to synthesize glutamine in vivo, thereby completely relieving cellular dependence on the externally supplied glutamine. Since the major fraction of ammonia produced in culture is from the catabolysis of externally supplied glutamine, such a gain of metabolic function reduces the levels of ammonia produced in culture.

In some embodiments of any of the above disclosed methods, ammonia is maintained at low levels in the cell culture medium. In a preferred embodiment, concentration of ammonia in the cell culture medium is maintained below 20 mM. In a preferred embodiment, the concentration of ammonia in the cell culture medium is maintained below 10 mM. In a preferred embodiment, the concentration of ammonia in the cell culture medium is maintained below 8 mM.

Cells

Any cell susceptible to cell culture may be utilized in accordance with the present invention. In some embodiments, the cell is a mammalian cell. Non-limiting examples of mammalian cells that may be used in accordance with the present invention include BALB/c mouse myeloma line (NS0/I, ECACC No: 85110503); human retinoblasts (PER.C6, CruCell, Leiden, The Netherlands); monkey kidney CV1 line transformed by SV40 (COS-7, ATCC CRL 1651); human embryonic kidney line (293 or 293 cells subcloned for growth in suspension culture, Graham et al., J. Gen Virol., 36:59, 1977); baby hamster kidney cells (BHK, ATCC CCL 10); Chinese hamster ovary cells +/−DHFR (CHO, Urlaub and Chasin, Proc. Natl. Acad. Sci. USA, 77:4216, 1980); mouse sertoli cells (TM4, Mather, Biol. Reprod., 23:243-251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68, 1982); MRC 5 cells; FS4 cells; and a human hepatoma line (Hep G2). In some preferred embodiment, the cells are CHO cells. In some preferred embodiments, the cells are GS-cells.

Additionally, any number of commercially and non-commercially available hybridoma cell lines may be utilized in accordance with the present invention. The term "hybridoma" as used herein refers to a cell or progeny of a cell resulting from fusion of an immortalized cell and an antibody-producing cell. Such a resulting hybridoma is an immortalized cell that produces antibodies. Individual cells used to create the hybridoma can be from any mammalian source, including, but not limited to, rat, pig, rabbit, sheep, pig, goat, and human. In some embodiments, a hybridoma is a trioma cell line, which results when progeny of heterohybrid myeloma fusions, which are the product of a fusion between human cells and a murine myeloma cell line, are subsequently fused with a plasma cell. In some embodiments, a hybridoma is any immortalized hybrid cell line that produces antibodies such as, for example, quadromas (See, e.g., Milstein et al., Nature, 537:3053, 1983). One skilled in the art will appreciate that hybridoma cell lines might have different nutrition requirements and/or might require different culture conditions for optimal growth, and will be able to modify conditions as needed.

Cell Culture Methods

The terms "culture" and "cell culture" as used herein refer to a cell population that is suspended in a medium under conditions suitable to survival and/or growth of the cell population. As will be clear to those of ordinary skill in the art, in some embodiments, these terms as used herein refer to the combination comprising the cell population and the medium in which the population is suspended. In some embodiments, the cells of the cell culture comprise mammalian cells.

The present invention may be used with any cell culture method that is amenable to the desired process (e.g., production of a recombinant protein (e.g., antibody)). As a non-limiting example, cells may be grown in batch or fed-batch cultures, where the culture is terminated after sufficient expression of the recombinant protein (e.g., antibody), after which the expressed protein (e.g., antibody) is harvested. Alternatively, as another non-limiting example, cells may be grown in batch-refeed, where the culture is not terminated and new nutrients and other components are periodically or continuously added to the culture, during which the expressed recombinant protein (e.g., antibody) is harvested periodically or continuously. Other suitable methods (e.g., spin-tube cultures) are known in the art and can be used to practice the present invention.

In some embodiments, a cell culture suitable for the present invention is a fed-batch culture. The term "fed-batch culture" as used herein refers to a method of culturing cells in which additional components are provided to the culture at a time or times subsequent to the beginning of the culture process. Such provided components typically comprise nutritional components for the cells which have been depleted during the culturing process. A fed-batch culture is typically stopped at some point and the cells and/or components in the medium are harvested and optionally purified. In some embodiments, the fed-batch culture comprises a base medium supplemented with feed media.

Cells may be grown in any convenient volume chosen by the practitioner. For example, cells may be grown in small scale reaction vessels ranging in volume from a few milliliters to several liters. Alternatively, cells may be grown in large scale commercial Bioreactors ranging in volume from approximately at least 1 liter to 10, 50, 100, 250, 500, 1000, 2500, 5000, 8000, 10,000, 12,000, 15000, 20000 or 25000 liters or more, or any volume in between.

The temperature of a cell culture will be selected based primarily on the range of temperatures at which the cell culture remains viable and the range in which a high level of desired product (e.g., a recombinant protein) is produced. In general, most mammalian cells grow well and can produce desired products (e.g., recombinant proteins) within a range of about 25° C. to 42° C., although methods taught by the present disclosure are not limited to these temperatures. Certain mammalian cells grow well and can produce desired products (e.g., recombinant proteins or antibodies) within the range of about 35° C. to 40° C. In certain embodiments, a cell culture is grown at a temperature of 20, 21, 22, 23, 24, 25, 26, 27, 28, 29, 30, 31, 32, 33, 34, 35, 36, 37, 38, 39, 40, 41, 42, 43, 44 or 45° C. at one or more times during the cell culture process. Those of ordinary skill in the art will be able to select appropriate temperature or temperatures in which to grow cells, depending on the particular needs of the cells and the particular production requirements of the practitioner. The cells may be grown for any amount of time, depending on the needs of the practitioner and the requirement of the cells themselves. In some embodiment, the cells are grown at 37° C. In some embodiments, the cells are grown at 36.5° C.

In some embodiments, the cells may be grown during the initial growth phase (or growth phase) for a greater or lesser amount of time, depending on the needs of the practitioner and the requirement of the cells themselves. In some embodiments, the cells are grown for a period of time sufficient to achieve a predefined cell density. In some embodiments, the cells are grown for a period of time sufficient to achieve a cell density that is a given percentage of the maximal cell density that the cells would eventually reach if allowed to grow undisturbed. For example, the cells may be grown for a period of time sufficient to achieve a desired viable cell density of 1, 5, 10, 15, 20, 25, 30, 35, 40, 45, 50, 55, 60, 65, 70, 75, 80, 85, 90, 95 or 99 percent of maximal cell density. In some embodiments, the cells are grown until the cell density does not increase by more than 15%, 14%, 13%, 12%, 11%, 10%, 9%, 8%, 7%, 6%, 5%, 4%, 3%, 2% or 1% per day of culture. In some embodiments, the cells are grown until the cell density does not increase by more than 5% per day of culture.

In some embodiment the cells are allowed to grow for a defined period of time. For example, depending on the starting concentration of the cell culture, the temperature at which the cells are grown, and the intrinsic growth rate of the cells, the cells may be grown for 0, 1, 2, 3, 4, 5, 6, 7, 8, 9, 10, 11, 12, 13, 14, 15, 16, 17, 18, 19, 20 or more days, preferably for 4 to 10 days. In some cases, the cells may be allowed to grow for a month or more. The practitioner of the present invention will be able to choose the duration of the initial growth phase depending on protein production requirements and the needs of the cells themselves.

The cell culture may be agitated or shaken during the initial culture phase in order to increase oxygenation and dispersion of nutrients to the cells. In accordance with the present invention, one of ordinary skill in the art will understand that it can be beneficial to control or regulate certain internal conditions of the bioreactor during the initial growth phase, including but not limited to pH, temperature, oxygenation, etc.

At the end of the initial growth phase, at least one of the culture conditions may be shifted so that a second set of culture conditions is applied and a metabolic shift occurs in the culture. A metabolic shift can be accomplished by, e.g., a change in the temperature, pH, osmolality or chemical inductant level of the cell culture. In one non-limiting embodiment, the culture conditions are shifted by shifting the temperature of the culture. However, as is known in the art, shifting temperature is not the only mechanism through which an appropriate metabolic shift can be achieved. For example, such a metabolic shift can also be achieved by shifting other culture conditions including, but not limited to, pH, osmolality, and sodium butyrate levels. The timing of the culture shift will be determined by the practitioner of the present invention, based on protein production requirements or the needs of the cells themselves.

When shifting the temperature of the culture, the temperature shift may be relatively gradual. For example, it may take several hours or days to complete the temperature change. Alternatively, the temperature shift may be relatively abrupt. For example, the temperature change may be complete in less than several hours. Given the appropriate production and control equipment, such as is standard in the commercial large-scale production of polypeptides or proteins, the temperature change may even be complete within less than an hour.

In some embodiments, once the conditions of the cell culture have been shifted as discussed above, the cell culture is maintained for a subsequent production phase under a second set of culture conditions conducive to the survival and viability of the cell culture and appropriate for expression of the desired polypeptide or protein at commercially adequate levels.

As discussed above, the culture may be shifted by shifting one or more of a number of culture conditions including, but not limited to, temperature, pH, osmolality, and sodium butyrate levels. In some embodiments, the temperature of the culture is shifted. According to this embodiment, during the subsequent production phase, the culture is maintained at a temperature or temperature range that is lower than the temperature or temperature range of the initial growth phase. As discussed above, multiple discrete temperature shifts may be employed to increase cell density or viability or to increase expression of the recombinant protein.

In some embodiments, the cells may be maintained in the subsequent production phase until a desired cell density or production titer is reached. In another embodiment of the present invention, the cells are allowed to grow for a defined period of time during the subsequent production phase. For example, depending on the concentration of the cell culture at the start of the subsequent growth phase, the temperature at which the cells are grown, and the intrinsic growth rate of the cells, the cells may be grown for 1, 2, 3, 4, 5, 6, 7, 8, 9, 10, 11, 12, 13, 14, 15, 16, 17, 18, 19, 20 or more days. In some cases, the cells may be allowed to grow for a month or more. The practitioner of the present invention will be able to choose the duration of the subsequent production phase depending on polypeptide or protein production requirements and the needs of the cells themselves.

The cell culture may be agitated or shaken during the subsequent production phase in order to increase oxygenation and dispersion of nutrients to the cells. In accordance with the present invention, one of ordinary skill in the art will understand that it can be beneficial to control or regulate certain internal conditions of the bioreactor during the subsequent growth phase, including but not limited to pH, temperature, oxygenation, etc.

In some embodiments, the cells express a recombinant protein and the cell culture method of the invention comprises a growth phase and a production phase.

In some embodiment step (ii) of any of the methods disclosed herein is applied during the totality of the cell culture method. In some embodiment step (ii) of any of the methods disclosed herein is applied during a part of the cell culture method. In some embodiments, step (ii) is applied until a predetermined viable cell density is obtained.

In some embodiments, the cell culture method of the invention comprises a growth phase and a production phase and step (ii) is applied during the growth phase. In some embodiments, the cell culture method of the invention comprises a growth phase and a production phase and step (ii) is applied during a part of the growth phase. In some embodiments, the cell culture method of the invention comprises a growth phase and a production phase and step (ii) is applied during the growth phase and the production phase. In step (ii) of any of the method disclosed herein, the term "maintaining" can refer to maintaining the concentration of amino acid or metabolite below C1 or C2 for the entire culture process (until harvesting) or for a part of the culture process such as for example the growth phase, a part of the growth phase or until a predetermined cell density is obtained.

Improvement of Cell Growth and Productivity

In some embodiments of any of the above mentioned methods, cell growth and/or productivity are increased as compared to a control culture, said control culture being identical except that it does not comprise step (ii).

In some embodiments of any of the above mentioned methods, the method of the invention is a method for improving cell growth. In some embodiment, the method of the invention is a method for improving cell growth in high density cell culture at high cell density.

High cell density as used herein refers to cell density above $1 \times 10^6$ cells/mL, $5 \times 10^6$ cells/mL, $1 \times 10^7$ cells/mL, $5 \times 10^7$ cells/mL, $1 \times 10^8$ cells/mL or $5 \times 10^8$ cells/mL, preferably above $1 \times 10^7$ cells/mL, more preferably above $5 \times 10^7$ cells/mL.

In some embodiments, the method of the invention is a method for improving cell growth in a cell culture where cell density is above $1 \times 10^6$ cells/mL, $5 \times 10^6$ cells/mL, $1 \times 10^7$ cells/mL, $5 \times 10^7$ cells/mL, $1 \times 10^8$ cells/mL or $5 \times 10^8$ cells/mL. In some embodiments, the method of the invention is a method for improving cell growth in a cell culture where maximum cell density is above $1 \times 10^6$ cells/mL, $5 \times 10^6$ cells/mL, $1 \times 10^7$ cells/mL, $5 \times 10^7$ cells/mL, $1 \times 10^8$ cells/mL or $5 \times 10^8$ cells/mL.

In some embodiments, cell growth is determined by viable cell density (VCD), maximum viable cell density, or Integrated viable cell count (IVCC). In some embodiments, cell growth is determined by maximum viable cell density.

The term "viable cell density" as used herein refers to the number of cells present in a given volume of medium. Viable cell density can be measured by any method known to the skilled person. Preferably, Viable cell density is measured using an automated cell counter such as Bioprofile Flex®. The term maximum cell density as used herein refers to the maximum cell density achieved during the cell culture. The term "cell viability" as used herein refers to the ability of cells in culture to survive under a given set of culture conditions or experimental variations. Those of ordinary skill in the art will appreciate that one of many methods for determining cell viability are encompassed in this invention. For example, one may use a dye (e.g., trypan blue) that does not pass through the membrane of a living cell, but can pass through the disrupted membrane of a dead or dying cell in order to determine cell viability.

The term "Integrated viable cell count (IVCC)" as used herein refers to as the area under the viable cell density (VCD) curve. IVCC can be calculated using the following formula:

$$IVCC_{t+1} = IVCC_t + (VCD_t + VCD_{t+1}) * (\Delta t)/2$$

where $\Delta t$ is the time difference between t and t+1 time points. $IVCC_{t=0}$ can be assumed negligible. $VCD_t$ and $VCD_{t+1}$ are viable cell densities at t and t+1 time points.

The term "titer" as used herein refers, for example, to the total amount of recombinantly expressed protein produced by a cell culture in a given amount of medium volume. Titer is typically expressed in units of grams of protein per liter of medium.

In some embodiments, cell growth is increased by at least 5%, 10%, 15%, 20% or 25% as compared to the control culture. In some embodiments, cell growth is increased by at least 10% as compared to the control culture. In some embodiments, cell growth is increased by at least 20% as compared to the control culture.

In some embodiments, the productivity is determined by titer and/or volumetric productivity.

The term "titer" as used herein refers, for example, to the total amount of recombinantly expressed protein produced by a cell culture in a given amount of medium volume. Titer is typically expressed in units of grams of protein per liter of medium.

In some embodiments, the productivity is determined by titer. In some embodiments, the productivity is increased by at least 5%, 10%, 15%, 20% or 25% as compared to the control culture.

In some embodiments, the productivity is increased by at least 10% as compared to a control culture.

In some embodiments, the productivity is increased by at least 20% as compared to a control culture.

In some embodiments, the maximum cell density of the cell culture is greater than $1 \times 10^6$ cells/mL, $5 \times 10^6$ cells/mL, $1 \times 10^7$ cells/mL, $5 \times 10^7$ cells/mL, $1 \times 10^8$ cells/mL or $5 \times 10^8$ cells/mL. In some embodiments, the maximum cell density of the cell culture is greater than $5 \times 10^6$ cells/mL. In some embodiments, the maximum cell density of the cell culture is greater than $1 \times 10^8$ cells/mL.

Cell Culture Media

The terms "medium", "cell culture medium" and "culture medium" as used herein refer to a solution containing nutrients which nourish growing mammalian cells. Typically, such solutions provide essential and non-essential amino acids, vitamins, energy sources, lipids, and trace elements required by the cell for minimal growth and/or survival. Such a solution may also contain supplementary components that enhance growth and/or survival above the minimal rate, including, but not limited to, hormones and/or other growth factors, particular ions (such as sodium, chloride, calcium, magnesium, and phosphate), buffers, vitamins, nucleosides or nucleotides, trace elements (inorganic compounds usually present at very low final concentrations), inorganic compounds present at high final concentrations (e.g., iron), amino acids, lipids, and/or glucose or other energy source. In some embodiments, a medium is advantageously formulated to a pH and salt concentration optimal for cell survival and proliferation. In some embodiments, a medium is a feed medium that is added after the beginning of the cell culture.

A wide variety of mammalian growth media may be used in accordance with the present invention. In some embodiments, cells may be grown in one of a variety of chemically defined media, wherein the components of the media are both known and controlled. In some embodiments, cells may be grown in a complex medium, in which not all components of the medium are known and/or controlled.

Chemically defined growth media for mammalian cell culture have been extensively developed and published over the last several decades. All components of defined media are well characterized, and so defined media do not contain complex additives such as serum or hydrolysates. Early media formulations were developed to permit cell growth and maintenance of viability with little or no concern for protein production. More recently, media formulations have been developed with the express purpose of supporting highly productive recombinant protein producing cell cultures. Such media are preferred for use in the method of the invention. Such media generally comprises high amounts of nutrients and in particular of amino acids to support the growth and/or the maintenance of cells at high density. If necessary, these media can be modified by the skilled person for use in the method of the invention. For example, the skilled person may decrease the amount of phenylalanine, tyrosine, tryptophan and/or methionine in these media for their use as base media or feed media in a method as disclosed herein.

Not all components of complex media are well characterized, and so complex media may contain additives such as simple and/or complex carbon sources, simple and/or complex nitrogen sources, and serum, among other things. In some embodiments, complex media suitable for the present invention contains additives such as hydrolysates in addition to other components of defined medium as described herein.

In some embodiments, defined media typically includes roughly fifty chemical entities at known concentrations in water. Most of them also contain one or more well-characterized proteins such as insulin, IGF-1, transferrin or BSA, but others require no protein components and so are referred to as protein-free defined media. Typical chemical components of the media fall into five broad categories: amino acids, vitamins, inorganic salts, trace elements, and a miscellaneous category that defies neat categorization.

Cell culture medium may be optionally supplemented with supplementary components. The term "supplementary components" as used herein refers to components that enhance growth and/or survival above the minimal rate, including, but not limited to, hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, and/or glucose or other energy source. In some embodiments, supplementary components may be added to the initial cell culture. In some embodiments, supplementary components may be added after the beginning of the cell culture.

Typically, trace elements refer to a variety of inorganic salts included at micromolar or lower levels. For example, commonly included trace elements are zinc, selenium, copper, and others. In some embodiments, iron (ferrous or ferric salts) can be included as a trace element in the initial cell culture medium at micromolar concentrations. Manganese is also frequently included among the trace elements as a divalent cation ($MnCl_2$ or $MnSO_4$) in a range of nanomolar to micromolar concentrations. Numerous less common trace elements are usually added at nanomolar concentrations.

In some embodiments, the medium used in the method of the invention is a medium suitable for supporting high cell density, such as for example $1\times10^6$ cells/mL, $5\times10^6$ cells/mL, $1\times10^7$ cells/mL, $5\times10^7$ cells/mL, $1\times10^8$ cells/mL or $5\times10^8$ cells/mL, in a cell culture. In some embodiments, the cell culture is a mammalian cell fed-batch culture, preferably a CHO cells fed-batch culture.

In some embodiments, the cell culture medium comprises phenylalanine at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises tyrosine at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises tryptophan at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises methionine at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises leucine at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises serine at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises threonine at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises glycine at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises two of phenylalanine, tyrosine, tryptophan, methionine, leucine, serine, threonine and glycine at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises phenylalanine and tyrosine at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises phenylalanine and tryptophan at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises phenylalanine and methionine at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises tyrosine and tryptophan at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises tyrosine and methionine at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises tryptophan and methionine at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises three of phenylalanine, tyrosine, tryptophan, methionine, leucine, serine, threonine and glycine at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises phenylalanine, tyrosine and tryptophan at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises phenylalanine, tyrosine and methionine at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises phenylalanine, tryptophan and methionine at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises tyrosine, tryptophan and methionine at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises four of phenylalanine, tyrosine, tryptophan, methionine, leucine, serine, threonine and glycine at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises phenylalanine, tyrosine, tryptophan and methionine at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises five of phenylalanine, tyrosine, tryptophan, methionine, leucine, serine, threonine and glycine at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises six of phenylalanine, tyrosine, tryptophan, methionine, leucine, serine, threonine and glycine at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises seven of phenylalanine, tyrosine, tryptophan, methionine, leucine, serine, threonine and glycine at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises phenylalanine, tyrosine, tryptophan, methionine, leucine, serine, threonine and glycine at a concentration below 2 mM, below 1 mM, between 0.1 and 2 mM, between 0.1 to 1 mM, between 0.5 and 1.5 mM or between 0.5 to 1 mM.

In some embodiments, the cell culture medium further comprises at least 1, 2, 3, 4, 5, 6, 7, 8, 9, 10, 11, 12 or 13 of glycine, valine, leucine, isoleucine, proline, serine, threonine, lysine, arginine, histidine, aspartate, glutamate and asparagine at a concentration above 2 mM, 3 mM, 4 mM, 5 mM, 10 mM, 15 mM, preferably 2 mM.

In some embodiments, the cell culture medium further comprises at least 5 of glycine, valine, leucine, isoleucine, proline, serine, threonine, lysine, arginine, histidine, aspartate, glutamate and asparagine at a concentration above 2 mM, 3 mM, 4 mM, 5 mM, 10 mM, 15 mM, preferably 2 mM.

In some embodiments, the cell culture medium further comprises glycine, valine, leucine, isoleucine, proline, serine, threonine, lysine, arginine, histidine, aspartate, glutamate and asparagine at a concentration above 2 mM, 3 mM, 4 mM, 5 mM, 10 mM, 15 mM, preferably 2 mM.

In some embodiments, the cell culture medium further comprises at least 1, 2, 3, 4, 5, 6, 7, 8, or 9 of valine, isoleucine, proline, lysine, arginine, histidine, aspartate, glutamate and asparagine at a concentration above 2 mM, 3 mM, 4 mM, 5 mM, 10 mM, 15 mM, preferably 2 mM.

In some embodiments, the cell culture medium further comprises at least 5 of valine, isoleucine, proline, lysine, arginine, histidine, aspartate, glutamate and asparagine at a concentration above 2 mM, 3 mM, 4 mM, 5 mM, 10 mM, 15 mM, preferably 2 mM.

In some embodiments, the cell culture medium further comprises valine, isoleucine, proline, lysine, arginine, histidine, aspartate, glutamate and asparagine at a concentration above 2 mM, 3 mM, 4 mM, 5 mM, 10 mM, 15 mM, preferably 2 mM.

In some embodiments, the cell culture medium comprises serine at a concentration above 3 mM, 5 mM, 7 mM, 10 mM, 15 mM or 20 mM, preferably 10 mM.

In some embodiments, the cell culture medium comprises valine at a concentration above 3 mM, 5 mM, 7 mM, 10 mM, 15 mM or 20 mM, preferably 10 mM.

In some embodiments, the cell culture medium comprises cysteine at a concentration above 3 mM, 5 mM, 7 mM, 10 mM, 15 mM or 20 mM, preferably 10 mM.

In some embodiments, the cell culture medium comprises isoleucine at a concentration above 3 mM, 5 mM, 7 mM, 10 mM, 15 mM or 20 mM, preferably 10 mM.

In some embodiments, the cell culture medium comprises leucine at a concentration above 3 mM, 5 mM, 7 mM, 10 mM, 15 mM or 20 mM, preferably 10 mM.

In some embodiments, the above cell culture medium is for use in a method as disclosed herein. In some embodiments, the above cell culture medium is used in a method as disclosed herein as a base media. In some embodiments, the above cell culture medium is used a method as disclosed herein as a feed media.

Expression of Proteins

As noted above, in many instances the cells will be selected or engineered to produce high levels of desired products (e.g., recombinant protein or antibody). Often, cells will be manipulated by the hand of man to produce high levels of recombinant protein, for example by introduction of a gene encoding the protein of interest and/or by introduction of genetic control elements that regulate expression of that gene (whether endogenous or introduced).

Certain proteins may have detrimental effects on cell growth, cell viability or some other characteristic of the cells that ultimately limits production of the protein of interest in some way. Even amongst a population of cells of one particular type engineered to express a specific protein, variability within the cellular population exists such that certain individual cells will grow better, produce more protein of interest, or produce a protein with higher activity levels (e.g., enzymatic activity). In certain embodiments, a cell line is empirically selected by the practitioner for robust growth under the particular conditions chosen for culturing the cells. In some embodiments, individual cells engineered to express a particular protein are chosen for large-scale production based on cell growth, final cell density, percent cell viability, titer of the expressed protein or any combination of these or any other conditions deemed important by the practitioner.

Any protein that is expressible in a host cell may be produced in accordance with the present teachings. The term "host cell" as used herein refers to a cell that is manipulated according to the present invention to produce a protein of interest as described herein. A protein may be expressed from a gene that is endogenous to the cell, or from a heterologous gene that is introduced into the cell. A protein may be one that occurs in nature, or may alternatively have a sequence that was engineered or selected by the hand of man.

Proteins that may desirably be expressed in accordance with the present invention will often be selected on the basis of an interesting or useful biological or chemical activity. For example, the present invention may be employed to express any pharmaceutically or commercially relevant enzyme, receptor, antibody, hormone, regulatory factor, antigen, binding agent, etc. In some embodiments, the protein expressed by cells in culture are selected from antibodies, or fragments thereof, nanobodies, single domain antibodies, glycoproteins, therapeutic proteins, growth factors, clotting factors, cytokines, fusion proteins, pharmaceutical drug substances, vaccines, enzymes, or Small Modular ImmunoPharmaceuticals™ (SMIPs). One of ordinary skill in the art will understand that any protein may be expressed in accordance with the present invention and will be able to select the particular protein to be produced based on his or her particular needs.

Antibodies

Given the large number of antibodies currently in use or under investigation as pharmaceutical or other commercial agents, production of antibodies is of particular interest in accordance with the present invention. Antibodies are proteins that have the ability to specifically bind a particular antigen. Any antibody that can be expressed in a host cell may be produced in accordance with the present invention. In some embodiments, the antibody to be expressed is a monoclonal antibody.

In some embodiments, the monoclonal antibody is a chimeric antibody. A chimeric antibody contains amino acid fragments that are derived from more than one organism. Chimeric antibody molecules can include, for example, an antigen binding domain from an antibody of a mouse, rat, or other species, with human constant regions. A variety of approaches for making chimeric antibodies have been described. See e.g., Morrison et al., *Proc. Natl. Acad. Sci. U.S.A.* 81, 6851 (1985); Takeda et al., *Nature* 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B.

In some embodiments, the monoclonal antibody is a human antibody derived, e.g., through the use of ribosome-display or phage-display libraries (see, e.g., Winter et al., U.S. Pat. No. 6,291,159 and Kawasaki, U.S. Pat. No. 5,658,754) or the use of xenographic species in which the native antibody genes are inactivated and functionally replaced with human antibody genes, while leaving intact the other components of the native immune system (see, e.g., Kucherlapati et al., U.S. Pat. No. 6,657,103).

In some embodiments, the monoclonal antibody is a humanized antibody. A humanized antibody is a chimeric antibody wherein the large majority of the amino acid residues are derived from human antibodies, thus minimizing any potential immune reaction when delivered to a human subject. In humanized antibodies, amino acid residues in the complementarity determining regions are replaced, at least in part, with residues from a nonhuman species that confer a desired antigen specificity or affinity. Such altered immunoglobulin molecules can be made by any of several techniques known in the art, (e.g., Teng et al., *Proc. Natl. Acad. Sci. U.S.A.*, 80, 7308-7312 (1983); Kozbor et al., *Immunology Today*, 4, 7279 (1983); Olsson et al., *Meth. Enzymol.*, 92, 3-16 (1982)), and are preferably made according to the teachings of PCT Publication WO92/06193 or EP 0239400, all of which are incorporated herein by reference). Humanized antibodies can be commercially produced by, for example, Scotgen Limited, 2 Holly Road, Twickenham, Middlesex, Great Britain. For further reference, see Jones et al., *Nature* 321:522-525 (1986); Riechmann et al., *Nature* 332:323-329 (1988); and Presta, *Curr. Op. Struct. Biol.* 2:593-596 (1992), all of which are incorporated herein by reference.

In some embodiments, the monoclonal, chimeric, or humanized antibodies described above may contain amino acid residues that do not naturally occur in any antibody in any species in nature. These foreign residues can be utilized, for example, to confer novel or modified specificity, affinity or effector function on the monoclonal, chimeric or humanized antibody. In some embodiments, the antibodies described above may be conjugated to drugs for systemic pharmacotherapy, such as toxins, low-molecular-weight cytotoxic drugs, biological response modifiers, and radionuclides (see e.g., Kunz et al., Calicheamicin derivative-carrier coniuqates, US20040082764 A1).

In general, practitioners of the present invention will select a protein of interest, and will know its precise amino acid sequence. Any given protein that is to be expressed in accordance with the present invention may have its own particular characteristics and may influence the cell density or viability of the cultured cells, may be expressed at lower levels than another protein grown under identical culture conditions, and may have different biological activity depending on the exact culture conditions and steps performed. One of ordinary skill in the art will be able to appropriately modify the steps and compositions used to produce a particular protein according to the teachings of the present invention in order to optimize cell growth and the production and/or activity level of any given expressed protein.

Introduction of Genes for the Expression of Proteins into Host Cells

Generally, a nucleic acid molecule introduced into the cell encodes the protein desired to be expressed according to the present invention. Alternatively, a nucleic acid molecule may encode a gene product that induces the expression of the desired protein by the cell. For example, introduced genetic material may encode a transcription factor that activates transcription of an endogenous or heterologous protein. Alternatively or additionally, an introduced nucleic acid molecule may increase the translation or stability of a protein expressed by the cell.

Methods suitable for introducing nucleic acids sufficient to achieve expression of a protein of interest into mammalian host cells are known in the art. See, for example, Gething et al., *Nature,* 293:620-625, 1981; Mantei et al., *Nature,* 281:40-46, 1979; Levinson et al. EP 117,060; and EP 117,058, each of which is incorporated herein by reference. For mammalian cells, common methods of introducing genetic material into mammalian cells include the calcium phosphate precipitation method of Graham and van der Erb (*Virology,* 52:456-457, 1978) or the Lipofectamine™ (Gibco BRL) Method of Hawley-Nelson (*Focus* 15:73, 1993). General aspects of mammalian cell host system transformations have been described by Axel in U.S. Pat. No. 4,399,216 issued Aug. 16, 1983. For various techniques for introducing genetic material into mammalian cells, see Keown et al., *Methods in Enzymology,* 1989, Keown et al., *Methods in Enzymology,* 185:527-537, 1990, and Mansour et al., *Nature,* 336:348-352, 1988.

In some embodiments, a nucleic acid to be introduced is in the form of a naked nucleic acid molecule. For example, the nucleic acid molecule introduced into a cell may consist only of the nucleic acid encoding the protein and the necessary genetic control elements. Alternatively, a nucleic acid encoding the protein (including the necessary regulatory elements) may be contained within a plasmid vector. Non-limiting representative examples of suitable vectors for expression of proteins in mammalian cells include pCDNA1; pCD, see Okayama, et al. Mol. Cell Biol. 5:1136-1142, 1985; pMCIneo Poly-A, see Thomas, et al. Cell 51:503-512, 1987; a baculovirus vector such as pAC 373 or pAC 610; CDM8, see Seed, B. Nature 329:840, 1987; and pMT2PC, see Kaufman, et al. EMBO J. 6:187-195, 1987, each of which is incorporated herein by reference in its entirety. In some embodiments, a nucleic acid molecule to be introduced into a cell is contained within a viral vector. For example, a nucleic acid encoding the protein may be inserted into the viral genome (or a partial viral genome). Regulatory elements directing the expression of the protein may be included with the nucleic acid inserted into the viral genome (i.e., linked to the gene inserted into the viral genome) or can be provided by the viral genome itself.

Naked DNA can be introduced into cells by forming a precipitate containing the DNA and calcium phosphate. Alternatively, naked DNA can also be introduced into cells by forming a mixture of the DNA and DEAE-dextran and incubating the mixture with the cells or by incubating the cells and the DNA together in an appropriate buffer and subjecting the cells to a high-voltage electric pulse (e.g., by electroporation). A further method for introducing naked DNA cells is by mixing the DNA with a liposome suspension containing cationic lipids. The DNA/liposome complex is then incubated with cells. Naked DNA can also be directly injected into cells by, for example, microinjection.

Alternatively, naked DNA can also be introduced into cells by complexing the DNA to a cation, such as polylysine, which is coupled to a ligand for a cell-surface receptor (see for example Wu, G. and Wu, C. H. J. Biol. Chem. 263: 14621, 1988; Wilson et al. J. Biol. Chem. 267:963-967, 1992; and U.S. Pat. No. 5,166,320, each of which is hereby incorporated by reference in its entirety). Binding of the DNA-ligand complex to the receptor facilitates uptake of the DNA by receptor-mediated endocytosis.

Use of viral vectors containing particular nucleic acid sequences, e.g., a cDNA encoding a protein, is a common approach for introducing nucleic acid sequences into a cell. Infection of cells with a viral vector has the advantage that a large proportion of cells receive the nucleic acid, which can obviate the need for selection of cells which have received the nucleic acid. Additionally, molecules encoded within the viral vector, e.g., by a cDNA contained in the viral vector, are generally expressed efficiently in cells that have taken up viral vector nucleic acid.

Defective retroviruses are well characterized for use in gene transfer for gene therapy purposes (for a review see Miller, A. D. Blood 76:271, 1990). A recombinant retrovirus can be constructed having a nucleic acid encoding a protein of interest inserted into the retroviral genome. Additionally, portions of the retroviral genome can be removed to render the retrovirus replication defective. Such a replication defective retrovirus is then packaged into virions which can be used to infect a target cell through the use of a helper virus by standard techniques.

The genome of an adenovirus can be manipulated such that it encodes and expresses a protein of interest but is inactivated in terms of its ability to replicate in a normal lytic viral life cycle. See, for example, Berkner et al. BioTechniques 6:616, 1988; Rosenfeld et al. Science 252:431-434, 1991; and Rosenfeld et al. Cell 68:143-155, 1992. Suitable adenoviral vectors derived from the adenovirus strain Ad type 5 dl324 or other strains of adenovirus (e.g., Ad2, Ad3, Ad7 etc.) are known to those skilled in the art. Recombinant adenoviruses are advantageous in that they do not require dividing cells to be effective gene delivery vehicles and can be used to infect a wide variety of cell types, including airway epithelium (Rosenfeld et al., 1992, cited supra), endothelial cells (Lemarchand et al., Proc. Natl. Acad. Sci. USA 89:6482-6486, 1992), hepatocytes (Herz and Gerard, Proc. Natl. Acad. Sci. USA 90:2812-2816, 1993) and muscle cells (Quantin et al., Proc. Natl. Acad. Sci. USA 89:2581-2584, 1992). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham, J. Virol. 57:267, 1986). Most replication-defective adenoviral vectors currently in use are deleted for all or parts of the viral E1 and E3 genes but retain as much as 80% of the adenoviral genetic material.

Adeno-associated virus (AAV) is a naturally occurring defective virus that requires another virus, such as an adenovirus or a herpes virus, as a helper virus for efficient replication and a productive life cycle. (For a review see Muzyczka et al. Curr. Topics in Micro. and Immunol., 158:97-129, 1992). It is also one of the few viruses that may integrate its DNA into non-dividing cells, and exhibits a high frequency of stable integration (see for example Flotte et al., Am. J. Respir. Cell. Mol. Biol. 7:349-356, 1992; Samulski et al., J. Virol. 63:3822-3828, 1989; and McLaughlin et al., J. Virol. 62:1963-1973, 1989). Vectors containing as little as 300 base pairs of AAV can be packaged and can integrate. Space for exogenous DNA is limited to about 4.5 kb. An AAV vector such as that described in Tratschin et al. (Mol. Cell. Biol. 5:3251-3260, 1985) can be used to introduce DNA into cells. A variety of nucleic acids have been introduced into different cell types using AAV vectors (see for example Hermonat et al., Proc. Natl. Acad. Sci. USA 81:6466-6470, 1984; Tratschin et al., Mol. Cell. Biol. 4:2072-2081, 1985; Wondisford et al., Mol. Endocrinol. 2:32-39, 1988; Tratschin et al., J. Virol. 51:611-619, 1984; and Flotte et al., J. Biol. Chem. 268:3781-3790, 1993).

When the method used to introduce nucleic acid molecules into a population of cells results in modification of a large proportion of the cells and efficient expression of the protein by the cells, the modified population of cells may be used without further isolation or subcloning of individual cells within the population. That is, there may be sufficient production of the protein by the population of cells such that no further cell isolation is needed and the population can be immediately be used to seed a cell culture for the production of the protein. Alternatively, it may be desirable to isolate and expand a homogenous population of cells from a few cells or a single cell that efficiently produce(s) the protein.

Alternative to introducing a nucleic acid molecule into a cell that encodes a protein of interest, the introduced nucleic acid may encode another polypeptide or protein that induces or increases the level of expression of the protein produced endogenously by a cell. For example, a cell may be capable of expressing a particular protein but may fail to do so without additional treatment of the cell. Similarly, the cell may express insufficient amounts of the protein for the desired purpose. Thus, an agent that stimulates expression of the protein of interest can be used to induce or increase expression of that protein by the cell. For example, the introduced nucleic acid molecule may encode a transcription factor that activates or upregulates transcription of the protein of interest. Expression of such a transcription factor in turn leads to expression, or more robust expression of the protein of interest.

In certain embodiments, a nucleic acid that directs expression of the protein is stably introduced into the host cell. In certain embodiments, a nucleic acid that directs expression of the protein is transiently introduced into the host cell. One of ordinary skill in the art will be able to choose whether to stably or transiently introduce a nucleic acid into the cell based on his or her experimental needs.

A gene encoding a protein of interest may optionally be linked to one or more regulatory genetic control elements. In certain embodiments, a genetic control element directs constitutive expression of the protein. In certain embodiments, a genetic control element that provides inducible expression of a gene encoding the protein of interest can be used. The use of an inducible genetic control element (e.g., an inducible promoter) allows for modulation of the production of the protein in the cell. Non-limiting examples of potentially useful inducible genetic control elements for use in eukaryotic cells include hormone-regulated elements (e.g., see Mader, S. and White, J. H., *Proc. Natl. Acad. Sci. USA* 90:5603-5607, 1993), synthetic ligand-regulated elements (see, e.g. Spencer, D. M. et al., *Science* 262:1019-1024, 1993) and ionizing radiation-regulated elements (e.g., see Manome, Y. et al., *Biochemistry* 32:10607-10613, 1993; Datta, R. et al., *Proc. Natl. Acad. Sci. USA* 89:10149-10153, 1992). Additional cell-specific or other regulatory systems known in the art may be used in accordance with the invention.

One of ordinary skill in the art will be able to choose and, optionally, to appropriately modify the method of introducing genes that cause the cell to express the protein of interest in accordance with the teachings of the present invention.

Isolation of the Expressed Protein

In general, it will typically be desirable to isolate and/or purify proteins expressed according to the present invention. In certain embodiments, the expressed protein is secreted into the medium and thus cells and other solids may be removed, as by centrifugation or filtering for example, as a first step in the purification process.

Alternatively, the expressed protein may be bound to the surface of the host cell. For example, the media may be removed and the host cells expressing the protein are lysed as a first step in the purification process. Lysis of mammalian host cells can be achieved by any number of means well known to those of ordinary skill in the art, including physical disruption by glass beads and exposure to high pH conditions.

The expressed protein may be isolated and purified by standard methods including, but not limited to, chromatography (e.g., ion exchange, affinity, size exclusion, and hydroxyapatite chromatography), gel filtration, centrifugation, or differential solubility, ethanol precipitation and/or by any other available technique for the purification of proteins (See, e.g., Scopes, Protein Purification Principles and Practice 2nd Edition, Springer-Verlag, New York, 1987; Higgins, S. J. and Hames, B. D. (eds.), Protein Expression: A Practical Approach, Oxford Univ Press, 1999; and Deutscher, M. P., Simon, M. I., Abelson, J. N. (eds.), Guide to Protein Purification: Methods in Enzymology (Methods in Enzymology Series, Vol. 182), Academic Press, 1997, each of which is incorporated herein by reference). For immunoaffinity chromatography in particular, the protein may be isolated by binding it to an affinity column comprising antibodies that were raised against that protein and were affixed to a stationary support. Alternatively, affinity tags such as an influenza coat sequence, poly-histidine, or glutathione-S-transferase can be attached to the protein by standard recombinant techniques to allow for easy purification by passage over the appropriate affinity column. Protease inhibitors such as phenyl methyl sulfonyl fluoride (PMSF), leupeptin, pepstatin or aprotinin may be added at any or all stages in order to reduce or eliminate degradation of the protein during the purification process. Protease inhibitors are particularly advantageous when cells must be lysed in order to isolate and purify the expressed protein.

One of ordinary skill in the art will appreciate that the exact purification technique will vary depending on the character of the protein to be purified, the character of the cells from which the protein is expressed, and/or the composition of the medium in which the cells were grown.

Pharmaceutical Formulations

In certain preferred embodiments of the invention, produced polypeptides or proteins will have pharmacologic activity and will be useful in the preparation of pharmaceuticals. Inventive compositions as described above may be administered to a subject or may first be formulated for delivery by any available route including, but not limited to parenteral (e.g., intravenous), intradermal, subcutaneous, oral, nasal, bronchial, ophthalmic, transdermal (topical), transmucosal, rectal, and vaginal routes. Inventive pharmaceutical compositions typically include a purified polypeptide or protein expressed from a mammalian cell line, a delivery agent (i.e., a cationic polymer, peptide molecular transporter, surfactant, etc., as described above) in combination with a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use typically include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition should be sterile and should be fluid to the extent that easy syringability exists. Preferred pharmaceutical formulations are stable under the conditions of manufacture and storage and must be preserved against the contaminating action of microorganisms such as bacteria and fungi. In general, the relevant carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the purified polypeptide or protein in the required amount in an appropriate solvent with one or a combination of ingredients enumerated above, as required, followed by filtered sterilization. Generally, dispersions are prepared by incorporating the purified polypeptide or protein expressed from a mammalian cell line into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the purified polypeptide or protein can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Formulations for oral delivery may advantageously incorporate agents to improve stability within the gastrointestinal tract and/or to enhance absorption.

For administration by inhalation, the inventive compositions comprising a purified polypeptide or protein expressed from a mammalian cell line and a delivery agent are preferably delivered in the form of an aerosol spray from a pressured container or dispenser which contains a suitable propellant, e.g., a gas such as carbon dioxide, or a nebulizer. The present invention particularly contemplates delivery of the compositions using a nasal spray, inhaler, or other direct delivery to the upper and/or lower airway. Intranasal administration of DNA vaccines directed against influenza viruses has been shown to induce CD8 T cell responses, indicating that at least some cells in the respiratory tract can take up DNA when delivered by this route, and the delivery agents of the invention will enhance cellular uptake. According to certain embodiments of the invention the compositions comprising a purified polypeptide expressed from a mammalian cell line and a delivery agent are formulated as large porous particles for aerosol administration.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the purified polypeptide or protein and delivery agents are formulated into ointments, salves, gels, or creams as generally known in the art.

The compositions can also be prepared in the form of suppositories (e.g., with conventional suppository bases such as cocoa butter and other glycerides) or retention enemas for rectal delivery.

In some embodiments, the compositions are prepared with carriers that will protect the polypeptide or protein against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active polypeptide or protein calculated to produce the desired therapeutic effect in association with the required pharmaceutical carrier.

The polypeptide or protein expressed according to the present invention can be administered at various intervals and over different periods of time as required, e.g., one time per week for between about 1 to 10 weeks, between 2 to 8 weeks, between about 3 to 7 weeks, about 4, 5, or 6 weeks, etc. The skilled artisan will appreciate that certain factors can influence the dosage and timing required to effectively treat a subject, including but not limited to the severity of the disease or disorder, previous treatments, the general health and/or age of the subject, and other diseases present. Generally, treatment of a subject with a polypeptide or protein as described herein can include a single treatment or, in many cases, can include a series of treatments. It is furthermore understood that appropriate doses may depend upon the potency of the polypeptide or protein and may optionally be tailored to the particular recipient, for example, through administration of increasing doses until a preselected desired response is achieved. It is understood that the specific dose level for any particular animal subject may depend upon a variety of factors including the activity of the specific polypeptide or protein employed, the age, body weight, general health, gender, and diet of the subject, the time of administration, the route of administration, the rate of excretion, any drug combination, and the degree of expression or activity to be modulated.

The present invention includes the use of compositions for treatment of nonhuman animals. Accordingly, doses and methods of administration may be selected in accordance with known principles of veterinary pharmacology and medicine. Guidance may be found, for example, in Adams, R. (ed.), *Veterinary Pharmacology and Therapeutics*, 8$^{th}$ edition, Iowa State University Press; ISBN: 0813817439; 2001.

Pharmaceutical compositions can be included in a container, pack, or dispenser together with instructions for administration.

Embodiments provided herein also include:
1. A method of cell culture comprising
(i) providing cells in a cell culture medium to start a cell culture process, and,
(ii) maintaining at least one metabolite selected from 3-(4-hydroxyphenyl)lactate, 4-hydroxyphenyl pyruvate, phenyllactate, indolelactate, indolecarboxylic acid, homocysteine, 2-hydroxybutyric acid, isovalerate and formate below a concentration C1 in the cell culture medium, wherein C1 is 3 mM.
2. The method of embodiment 1 wherein said metabolite is selected from 3-(4-hydroxyphenyl)lactate, 4-hydroxyphenylpyruvate, phenyllactate, indolelactate, indolecarboxylic acid, homocysteine and 2-hydroxybutyric acid
3. The method of embodiment 1 wherein C1 is 1 mM.
4. The method of embodiment 1 wherein C1 is 0.5 mM.
5. The method of any one of embodiments 1 to 4 wherein step ii) comprises the step of measuring the concentration of said at least one metabolite.
6. The method of embodiment 5 wherein said concentration is measured off line.
7. The method of embodiment 6 wherein measuring the concentration of said at least one metabolite comprises taking a sample from the cell culture medium and measuring the concentration of said at least one metabolite in said sample.
8. The method of any one of embodiments 5 to 7 wherein said concentration is measured by LC-MS.
9. The method of embodiment 5 wherein said concentration is measured online.
10. The method of embodiment 9 wherein said concentration is measured online using Raman spectroscopy.
11. The method of embodiment 9 wherein said concentration is measured online using NMR, HPLC or UPLC.
12. The method of any one of embodiments 5 to 11 wherein said concentration is measured intermittently, every 30 min, every hour, every two hours, twice a day, daily, or every two days.
13. The method of embodiment 9 or 10 wherein said concentration is measured continuously.
14. The method of any one of embodiments 5 to 13 wherein, when the measured concentration is above a predefined value, the concentration of precursor of said at least one metabolite in the cell culture medium is decreased.
15. The method of embodiment 14 wherein said predefined value is C1.
16. The method of embodiment 14 wherein said predefined value is a percentage of C1.
17. The method of embodiment 16 wherein said predefined value is 50, 55, 60, 65, 70, 75, 80, 85, 90 or 95% of C1.
18. The method of embodiment 17 wherein said predefined value is 80% of C1.
19. The method of any one of embodiments 14 to 18 wherein the concentration of precursor is decreased by reducing the amount of precursor provided to the cells.
20. The method of any one of embodiments 14 to 19 wherein the concentration of precursor is decreased by reducing the concentration of said precursor in the feed medium.
21. The method of any one of embodiments 14 to 20 wherein the concentration of precursor is decreased by reducing the feed rate.
22. The method of any one of embodiments 14 to 21 wherein the concentration of precursor is decreased by reducing the number of feeds.
23. The method of any one of embodiments 14 to 22 wherein, when the concentration of precursor is decreased by reducing the volume of feeds.
24. The method of any one of embodiments 14 to 23 wherein when the measured concentration of 3-(4-hydroxyphenyl)lactate, 4-hydroxyphenylpyruvate and/or phenyllactate is above said predefined value, the concentration of phenylalanine is decreased in the cell culture medium.
25. The method of any one of embodiments 14 to 24 wherein when the measured concentration of 3-(4-hydroxyphenyl)lactate and/or 4-hydroxyphenylpyruvate is above said predefined value, the concentration of tyrosine is decreased in the cell culture medium.
26. The method of any one of embodiments 14 to 25 wherein when the measured concentration of indolelactate and/or indolecarboxylic acid is above said predefined value, the concentration of tryptophan is decreased in the cell culture medium.

27. The method of any one of embodiments 14 to 26 wherein when the measured concentration of homocysteine and/or 2-hydroxybutyric acid is above said predefined value, the concentration of methionine is decreased in the cell culture medium.

28. The method of any one of embodiments 14 to 27 wherein when the measured concentration of isovalerate is above said predefined value, the concentration of leucine is decreased in the cell culture medium.

29. The method of any one of embodiments 14 to 28 wherein when the measured concentration of formate is above said predefined value, the concentration of serine, threonine and/or glycine is decreased in the cell culture medium.

30. The method of any one of embodiments 1 to 29 wherein step (ii) comprises maintaining 1, 2, 3, 4, 5, 6, 7, 8 or 9 of 3-(4-hydroxyphenyl)lactate, 4-hydroxyphenylpyruvate, phenyllactate, indolelactate, indolecarboxylic acid, homocysteine, 2-hydroxybutyric acid, isovalerate and formate below C1 in the cell culture medium.

31. The method of any one of embodiments 1 to 30 wherein step (ii) comprises maintaining 1, 2, 3, 4, 5, 6, or 7 of 3-(4-hydroxyphenyl)lactate, 4-hydroxyphenylpyruvate, phenyllactate, indolelactate, indolecarboxylic acid, homocysteine and 2-hydroxybutyric acid below C1 in the cell culture medium.

32. The method of any one of embodiments 1 to 31 wherein step (ii) comprises maintaining 3-(4-hydroxyphenyl)lactate, 4-hydroxyphenylpyruvate and phenyllactate below C1 in the cell culture medium.

33. The method of any one of embodiments 1 to 32 wherein step (ii) comprises maintaining indolelactate and indolecarboxylic acid below C1 in the cell culture medium.

34. The method of any one of embodiments 1 to 33 wherein step (ii) comprises maintaining homocysteine and 2-hydroxybutyric acid below C1 in the cell culture medium.

35. The method of any one of embodiments 1 to 34 wherein step (ii) comprises maintaining isovalerate below C1 in the cell culture medium.

36. The method of any one of embodiments 1 to 35 wherein step (ii) comprises maintaining formate below C1 in the cell culture medium.

37. The method of any one of embodiments 1 to 36 wherein, in step (ii), the concentration of 3-(4-hydroxyphenyl)lactate is maintained below 0.5 mM.

38. The method of any one of embodiments 1 to 37 wherein, in step (ii), the concentration of 3-(4-hydroxyphenyl)lactate is maintained below 0.3 mM.

39. The method of any one of embodiments 1 to 38 wherein, in step (ii), the concentration of 3-(4-hydroxyphenyl)lactate is maintained below 0.1 mM.

40. The method of any one of embodiments 1 to 39 wherein, in step (ii), the concentration of 4-hydroxyphenylpyruvate is maintained below 0.1 mM.

41. The method of any one of embodiments 1 to 40 wherein, in step (ii), the concentration of 4-hydroxyphenylpyruvate is maintained below 0.05 mM.

42. The method of any one of embodiments 1 to 41 wherein, in step (ii), the concentration of 4-hydroxyphenylpyruvate is maintained below 0.02 mM.

43. The method of any one of embodiments 1 to 42 wherein, in step (ii), the concentration of phenyllactate is maintained below 0.5 mM.

44. The method of any one of embodiments 1 to 43 wherein, in step (ii), the concentration of phenyllactate is maintained below 0.2 mM.

45. The method of any one of embodiments 1 to 44 wherein, in step (ii), the concentration of phenyllactate is maintained below 0.1 mM.

46. The method of any one of embodiments 1 to 45 wherein, in step (ii), the concentration of indolelactate is maintained below 3 mM.

47. The method of any one of embodiments 1 to 46 wherein, in step (ii), the concentration of indolelactate is maintained below 1 mM.

48. The method of any one of embodiments 1 to 47 wherein, in step (ii), the concentration of indolelactate is maintained below 0.3 mM.

49. The method of any one of embodiments 1 to 48 wherein, in step (ii), the concentration of indolelactate is maintained below 0.1 mM.

50. The method of any one of embodiments 1 to 49 wherein, in step (ii), the concentration of indolecarboxylic acid is maintained below 1 mM.

51. The method of any one of embodiments 1 to 50 wherein, in step (ii), the concentration of indolecarboxylic acid is maintained below 0.5 mM.

52. The method of any one of embodiments 1 to 51 wherein, in step (ii), the concentration of indolecarboxylic acid is maintained below 0.2 mM.

53. The method of any one of embodiments 1 to 52 wherein, in step (ii), the concentration of homocysteine is maintained below 0.5 mM.

54. The method of any one of embodiments 1 to 53 wherein, in step (ii), the concentration of homocysteine is maintained below 0.3 mM.

55. The method of any one of embodiments 1 to 54 wherein, in step (ii), the concentration of homocysteine is maintained below 0.1 mM.

56. The method of any one of embodiments 1 to 55 wherein, in step (ii), the concentration of 2-hydroxybutyric acid is maintained below 1 mM.

57. The method of any one of embodiments 1 to 56 wherein, in step (ii), the concentration of 2-hydroxybutyric acid is maintained below 0.5 mM.

58. The method of any one of embodiments 1 to 57 wherein, in step (ii), the concentration of 2-hydroxybutyric acid is maintained below 0.2 mM.

59. The method of any one of embodiments 1 to 58 wherein, in step (ii), the concentration of isovalerate is maintained below 2 mM.

60. The method of any one of embodiments 1 to 59 wherein, in step (ii), the concentration of isovalerate is maintained below 1 mM.

61. The method of any one of embodiments 1 to 60 wherein, in step (ii), the concentration of isovalerate is maintained below 0.5 mM.

62. The method of any one of embodiments 1 to 61 wherein, in step (ii), the concentration of formate acid is maintained below 4 mM.

63. The method of any one of embodiments 1 to 62 wherein, in step (ii), the concentration of formate acid is maintained below 3 mM.

64. The method of any one of embodiments 1 to 63 wherein, in step (ii), the concentration of formate acid is maintained below 2 mM.

65. A method of cell culture comprising
(i) providing cells in a cell culture medium to start a cell culture process, and, (ii) maintaining at least one amino acid selected from phenylalanine, tyrosine, tryptophan, methionine, leucine, serine, threonine and glycine below a concentration C2 in the cell culture medium, wherein C2 is 2 mM.

66. The method of embodiment 65 wherein step ii) comprises the step of measuring the concentration of said at least one amino acid.

67. The method of embodiment 66 wherein said concentration is measured off line.

68. The method of embodiment 67 wherein measuring the concentration of said at least one amino acid comprises taking a sample from the cell culture medium and measuring the concentration of said at least one amino acid in said sample.

69. The method of any one of embodiments 66 to 68 wherein said concentration is measured by LC-MS.

70. The method of embodiment 66 wherein said concentration is measured online.

71. The method of embodiment 70 wherein said concentration is measured online using Raman spectroscopy.

72. The method of embodiment 70 wherein said concentration is measured online using NMR, HPLC or UPLC.

73. The method of any one of embodiments 66 to 72 wherein said concentration is measured intermittently, every 30 min, every hour, every two hours, twice a day, daily, or every two days.

74. The method of embodiment 70 or 71 wherein said concentration is measured continuously.

75. The method of any one of embodiments 65 to 74 wherein, when the measured concentration is above a pre-defined value, the concentration of said at least one amino acid in the cell culture medium is decreased.

76. The method of embodiment 75 wherein said pre-defined value is C2.

77. The method of embodiment 75 wherein said pre-defined value is a percentage of C2.

78. The method of embodiment 77 wherein said pre-defined value is 50, 55, 60, 65, 70, 75, 80, 85, 90 or 95% of C2.

79. The method of embodiment 78 wherein said pre-defined value is 80% of C2.

80. The method of any one of embodiments 75 to 79 wherein, when the concentration of said at least one amino acid is decreased by reducing the amount of amino acid provided to the cells.

81. The method of any one of embodiments 75 to 80 wherein, when the concentration of said at least one amino acid is decreased by reducing the concentration of said amino acid in the feed medium.

82. The method of any one of embodiments 75 to 81 wherein, when the concentration of said at least one amino acid is decreased by reducing the feed rate.

83. The method of any one of embodiments 75 to 82 wherein, when the concentration of said at least one amino acid is decreased by reducing the number of feeds.

84. The method of any one of embodiments 75 to 83 wherein, when the concentration of said at least one amino acid is decreased by reducing the volume of feeds.

85. The method of any one of embodiments 1 to 84 wherein the concentration of phenylalanine is maintained below 2 mM in the cell culture medium.

86. The method of any one of embodiments 1 to 85 wherein the concentration of phenylalanine is maintained between 0.1 and 2 mM in the cell culture medium.

87. The method of any one of embodiments 1 to 86 wherein the concentration of phenylalanine is maintained between 0.1 and 1 mM in the cell culture medium.

88. The method of any one of embodiments 1 to 87 wherein the concentration of phenylalanine is maintained between 0.2 and 1 mM in the cell culture medium.

89. The method of any one of embodiments 1 to 88 wherein the concentration of phenylalanine is maintained between 0.5 and 1 mM in the cell culture medium.

90. The method of any one of embodiments 1 to 89 wherein the concentration of tyrosine is maintained below 2 mM in the cell culture medium.

91. The method of any one of embodiments 1 to 90 wherein the concentration of tyrosine is maintained between 0.1 and 2 mM in the cell culture medium.

92. The method of any one of embodiments 1 to 91 wherein the concentration of tyrosine is maintained between 0.1 and 1 mM in the cell culture medium.

93. The method of any one of embodiments 1 to 92 wherein the concentration of tyrosine is maintained between 0.2 and 1 mM in the cell culture medium.

94. The method of any one of embodiments 1 to 93 wherein the concentration of tyrosine is maintained between 0.5 and 1 mM in the cell culture medium.

95. The method of any one of embodiments 1 to 94 wherein the concentration of tryptophan is maintained below 2 mM in the cell culture medium.

96. The method of any one of embodiments 1 to 95 wherein the concentration of tryptophan is maintained between 0.1 and 2 mM in the cell culture medium.

97. The method of any one of embodiments 1 to 96 wherein the concentration of tryptophan is maintained between 0.1 and 1 mM in the cell culture medium.

98. The method of any one of embodiments 1 to 97 wherein the concentration of tryptophan is maintained between 0.2 and 1 mM in the cell culture medium.

99. The method of any one of embodiments 1 to 98 wherein the concentration of tryptophan is maintained between 0.5 and 1 mM in the cell culture medium.

100. The method of any one of embodiments 1 to 99 wherein the concentration of methionine is maintained below 2 mM in the cell culture medium.

101. The method of any one of embodiments 1 to 100 wherein the concentration of methionine is maintained between 0.1 and 2 mM in the cell culture medium.

102. The method of any one of embodiments 1 to 101 wherein the concentration of methionine is maintained between 0.1 and 1 mM in the cell culture medium.

103. The method of any one of embodiments 1 to 102 wherein the concentration of methionine is maintained between 0.2 and 1 mM in the cell culture medium.

104. The method of any one of embodiments 1 to 103 wherein the concentration of methionine is maintained between 0.5 and 1 mM in the cell culture medium.

105. The method of any one of embodiments 1 to 104 wherein the concentration of leucine is maintained below 2 mM in the cell culture medium.

106. The method of any one of embodiments 1 to 105 wherein the concentration of leucine is maintained between 0.1 and 2 mM in the cell culture medium.

107. The method of any one of embodiments 1 to 106 wherein the concentration of leucine is maintained between 0.1 and 1 mM in the cell culture medium.

108. The method of any one of embodiments 1 to 107 wherein the concentration of leucine is maintained between 0.2 and 1 mM in the cell culture medium.

109. The method of any one of embodiments 1 to 108 wherein the concentration of leucine is maintained between 0.5 and 1 mM in the cell culture medium.

110. The method of any one of embodiments 1 to 109 wherein the concentration of serine is maintained below 2 mM in the cell culture medium.

111. The method of any one of embodiments 1 to 110 wherein the concentration of serine is maintained between 0.1 and 2 mM in the cell culture medium.

112. The method of any one of embodiments 1 to 111 wherein the concentration of serine is maintained between 0.1 and 1 mM in the cell culture medium.

113. The method of any one of embodiments 1 to 112 wherein the concentration of serine is maintained between 0.2 and 1 mM in the cell culture medium.

114. The method of any one of embodiments 1 to 113 wherein the concentration of serine is maintained between 0.5 and 1 mM in the cell culture medium.

115. The method of any one of embodiments 1 to 114 wherein the concentration of threonine is maintained below 2 mM in the cell culture medium.

116. The method of any one of embodiments 1 to 115 wherein the concentration of threonine is maintained between 0.1 and 2 mM in the cell culture medium.

117. The method of any one of embodiments 1 to 116 wherein the concentration of threonine is maintained between 0.1 and 1 mM in the cell culture medium.

118. The method of any one of embodiments 1 to 117 wherein the concentration of threonine is maintained between 0.2 and 1 mM in the cell culture medium.

119. The method of any one of embodiments 1 to 118 wherein the concentration of threonine is maintained between 0.5 and 1 mM in the cell culture medium.

120. The method of any one of embodiments 1 to 119 wherein the concentration of glycine is maintained below 2 mM in the cell culture medium.

121. The method of any one of embodiments 1 to 120 wherein the concentration of glycine is maintained between 0.1 and 2 mM in the cell culture medium.

122. The method of any one of embodiments 1 to 121 wherein the concentration of glycine is maintained between 0.1 and 1 mM in the cell culture medium.

123. The method of any one of embodiments 1 to 122 wherein the concentration of glycine is maintained between 0.2 and 1 mM in the cell culture medium.

124. The method of any one of embodiments 1 to 123 wherein the concentration of glycine is maintained between 0.5 and 1 mM in the cell culture medium.

125. The method of any one of embodiments 1 to 124 wherein the cell culture medium comprises 1, 2, 3, 4, 5, 6, 7, 8, 9, 10, 11, 12 or 13 of glycine, valine, leucine, isoleucine, proline, serine, threonine, lysine, arginine, histidine, aspartate, glutamate and asparagine at a concentration above 1 mM, 1.5 mM, 2 mM, 3 mM or 5 mM.

126. The method of any one of embodiments 1 to 124 wherein the cell culture medium comprises 1, 2, 3, 4, 5, 6, 7, 8 or 9 of valine, isoleucine, proline, lysine, arginine, histidine, aspartate, glutamate and asparagine at a concentration above 1 mM, 1.5 mM, 2 mM, 3 mM or 5 mM.

127. The method of any one of embodiments 1 to 124 wherein the cell culture medium comprises one of glycine, valine, leucine, isoleucine, proline, serine, threonine, lysine, arginine, histidine, aspartate, glutamate and asparagine at a concentration above 2 mM.

128. The method of any one of embodiments 1 to 124 wherein the cell culture medium comprises one of valine, isoleucine, proline, lysine, arginine, histidine, aspartate, glutamate and asparagine at a concentration above 2 mM.

129. The method of any one of embodiments 1 to 124 wherein the cell culture medium comprises one of glycine, valine, leucine, isoleucine, proline, serine, threonine, lysine, arginine, histidine, aspartate, glutamate and asparagine at a concentration above 5 mM.

130. The method of any one of embodiments 1 to 124 wherein the cell culture medium comprises one of valine, isoleucine, proline, lysine, arginine, histidine, aspartate, glutamate and asparagine at a concentration above 5 mM.

131. The method of any one of embodiments 1 to 130 where lactate is maintained at low levels in the cell culture medium.

132. The method of any one of embodiments 1 to 131 where concentration of lactate in the cell culture medium is maintained below 90 mM.

133. The method of any one of embodiments 1 to 132 where concentration of lactate in the cell culture medium is maintained below 70 mM.

134. The method of any one of embodiments 1 to 133 where concentration of lactate in the cell culture medium is maintained below 50 mM.

135. The method of any one of embodiments 1 to 134 where concentration of lactate in the cell culture medium is maintained below 40 mM.

136. The method of any one of embodiments 1 to 135 where concentration of lactate in the cell culture medium is maintained at low levels by controlling the amount of glucose provided to the cell culture.

137. The method of any one of embodiments 1 to 136 where concentration of lactate in the cell culture medium is maintained at low levels by using the HIPDOG process.

138. The method of any one of embodiments 1 to 137 wherein a pH sensor is used to monitor pH of the cell culture, and, in response to a rise above a predetermined pH value, glucose is fed to the cell culture.

139. The method of embodiment 138, wherein the predetermined pH value is approximately 7.

140. The method of any one of embodiments 1 to 139 where ammonia is controlled at low levels in the cell culture medium.

141. The method of any one of embodiments 1 to 140 where concentration of ammonia in the cell culture medium is maintained below 20 mM.

142. The method of any one of embodiments 1 to 141 where concentration of ammonia in the cell culture medium is maintained below 10 mM.

143. The method of any one of embodiments 1 to 142 where concentration of ammonia in the cell culture medium is maintained below 8 mM.

144. The method of any one of embodiments 1 to 143, wherein the cells are mammalian cells.

145. The method embodiment 144, wherein the mammalian cells are selected from BALB/c mouse myeloma line, human retinoblasts (PER.C6), monkey kidney cells, human embryonic kidney line (293), baby hamster kidney cells (BHK), Chinese hamster ovary cells (CHO), mouse sertoli cells, African green monkey kidney cells (VERO-76), human cervical carcinoma cells (HeLa), canine kidney cells, buffalo rat liver cells, human lung cells, human liver cells, mouse mammary tumor cells, TRI cells, MRC 5 cells, FS4 cells, or human hepatoma line (Hep G2).

146. The method of embodiment 145, wherein the mammalian cells are CHO cells.

147. The method of embodiment 146, wherein the mammalian cells are GS-CHO cells.

148. The method of any one of embodiments 1 to 147, wherein the cell culture is a fed batch culture.

149. The method of embodiment 148, wherein the fed batch culture comprises a base medium supplemented with feed media.

150. The method of embodiment 148 or 149, wherein the base medium and/or feed media are substantially free of serum.

151. The method of any one of embodiments 1 to 150 wherein said method is a method for improving cell growth.

152. The method of any one of embodiments 1 to 151 wherein said method is a method for improving cell growth in high density cell culture.

153. The method of any one of embodiments 1 to 152 wherein said method is a method for improving cell growth in a cell culture where maximum viable cell density is above $5 \times 10^6$ cells/mL, and preferably above $5 \times 10^7$ cells/mL.

154. The method of any one of embodiments 1 to 153, wherein the cell culture system is a large-scale production system.

155. The method of any one of embodiments 1 to 154, wherein the cell culture system uses a bioreactor.

156. The method of any one of embodiments 1 to 155, wherein the cell culture method comprises a growth phase and a production phase and step (ii) is applied during the growth phase.

157. The method of any one of embodiments 1 to 156, wherein the volume of the cell culture medium is at least 500 L.

158. The method of any one of embodiments 1 to 156, wherein the volume of the cell culture medium is at least 5000 L.

159. The method of any one of embodiments 1 to 158, wherein the cells express a recombinant protein.

160. The method of embodiment 159, wherein the recombinant protein is selected from the group consisting of antibodies or fragments thereof, nanobodies, single domain antibodies, Small Modular ImmunoPharmaceuticals™ (SMIPs), VHH antibodies, camelid antibodies, shark single domain polypeptides (IgNAR), single domain scaffolds (e.g., fibronectin scaffolds), SCORPION™ therapeutics (single chain polypeptides comprising an N-terminal binding domain, an effector domain, and a C-terminal binding domain), growth factors, clotting factors, cytokines, fusion proteins, pharmaceutical drug substances, vaccines, enzymes and combinations thereof.

161. The method of embodiment 159 or 160, wherein the recombinant protein is a glycoprotein.

162. The method of any one of embodiments 159 to 161, further comprising obtaining recombinant protein produced by the cells.

163. The method of embodiment 162, further comprising purifying the recombinant protein.

164. The method of embodiment 163, further comprising preparing a pharmaceutical composition comprising the recombinant protein.

165. A recombinant protein produced using a method of any one of embodiments 159 to 163.

166. The method of any one of embodiments 1 to 130, wherein cell growth and/or productivity are increased as compared to a control culture, said control culture being identical except it does not comprise step (ii).

167. The method of embodiment 166, wherein the cell growth is determined by viable cell density, maximum viable cell density or Integrated Viable Cell Count.

168. The method of embodiment 166 or 167, wherein the cell growth is determined by maximum cell density.

169. The method of any one of embodiments 166 to 168, wherein the cell growth is increased by at least 5% as compared to the control culture.

170. The method of any one of embodiments 166 to 169, wherein the cell growth is increased by at least 10% as compared to the control culture.

171. The method of any one of embodiments 166 to 170, wherein the cell growth is increased by at least 20% as compared to the control culture.

172. The method of embodiment 166, wherein the productivity is determined by titer, and/or volumetric productivity.

173. The method of any one of embodiments 166-172, wherein the productivity is determined by titer.

174. The method of embodiments 172 or 173, wherein the productivity is increased by at least 5% as compared to the control culture.

175. The method of any one of embodiments 172 to 174, wherein the productivity is increased by at least 10% as compared to the control culture.

176. The method of any one of embodiments 172 to 175, wherein the productivity is increased by at least 20% as compared to the control culture.

177. The method of any one of embodiments 1 to 164 and 166 to 176, wherein the maximum viable cell density of the cell culture is greater than $1 \times 10^6$ cells/mL, $5 \times 10^6$ cells/mL, $1 \times 10^7$ cells/mL, $5 \times 10^7$ cells/mL, $1 \times 10^8$ cells/mL or $5 \times 10^8$ cells/mL.

178. The method of embodiment 177, wherein the maximum viable cell density of the cell culture is greater than $5 \times 10^6$ cells/mL and preferably greater than $5 \times 10^7$ cells/mL.

179. The method of embodiment 178, wherein the maximum viable cell density of the cell culture is greater than $1 \times 10^8$ cells/mL cells/mL.

180. A cell culture medium comprising phenylalanine at a concentration below 2 mM.

181. The cell culture medium of embodiment 180 comprising tyrosine at a concentration below 2 mM.

182. The cell culture medium of embodiments 180 or 181 comprising tryptophan at a concentration below 2 mM.

183. A cell culture medium of any one of embodiments 180 to 182 comprising methionine at a concentration below 2 mM.

184. The cell culture medium of any one of embodiments 180 to 183 comprising leucine at a concentration below 2 mM.

185. The cell culture medium of any one of embodiments 180 to 184 comprising serine at a concentration below 2 mM.

186. The cell culture medium of any one of embodiments 180 to 185 comprising threonine at a concentration below 2 mM.

187. The cell culture medium of any one of embodiments 180 to 186 comprising glycine at a concentration below 2 mM.

188. A cell culture medium comprising tyrosine at a concentration below 2 mM.

189. The cell culture medium of embodiment 188 comprising tryptophan at a concentration below 2 mM.

190. The cell culture medium of embodiments 188 or 189 comprising methionine at a concentration below 2 mM.

191. The cell culture medium of any one of embodiments 188 to 190 comprising leucine at a concentration below 2 mM.

192. The cell culture medium of any one of embodiments 188 to 190 comprising serine at a concentration below 2 mM.

193. The cell culture medium of any one of embodiments 188 to 190 comprising threonine at a concentration below 2 mM.

194. The cell culture medium of any one of embodiments 188 to 190 comprising glycine at a concentration below 2 mM.

195. A cell culture medium comprising tryptophan at a concentration below 2 mM.

196. The cell culture medium of embodiment 195 comprising methionine at a concentration below 2 mM.

197. The cell culture medium of any one of embodiments 195 to 196 comprising leucine at a concentration below 2 mM.

198. The cell culture medium of any one of embodiments 195 to 197 comprising serine at a concentration below 2 mM.

199. The cell culture medium of any one of embodiments 195 to 198 comprising threonine at a concentration below 2 mM.

200. The cell culture medium of any one of embodiments 195 to 199 comprising glycine at a concentration below 2 mM.

201. A cell culture medium comprising methionine at a concentration below 2 mM.

202. The cell culture medium of embodiment 201 comprising leucine at a concentration below 2 mM.

203. The cell culture medium of any one of embodiments 201 to 202 comprising serine at a concentration below 2 mM.

204. The cell culture medium of any one of embodiments 201 to 203 comprising threonine at a concentration below 2 mM.

205. The cell culture medium of any one of embodiments 201 to 204 comprising glycine at a concentration below 2 mM.

206. A cell culture medium comprising leucine at a concentration below 2 mM.

207. The cell culture medium of embodiment 206 comprising serine at a concentration below 2 mM.

208. The cell culture medium of any one of embodiments 206 to 207 comprising threonine at a concentration below 2 mM.

209. The cell culture medium of any one of embodiments 206 to 208 comprising glycine at a concentration below 2 mM.

210. A cell culture medium comprising serine at a concentration below 2 mM.

211. The cell culture medium of embodiment 210 comprising threonine at a concentration below 2 mM.

212. The cell culture medium of any one of embodiments 210 to 211 comprising glycine at a concentration below 2 mM.

213. A cell culture medium comprising threonine at a concentration below 2 mM.

214. The cell culture medium of any one of embodiments 210 to 213 comprising glycine at a concentration below 2 mM.

215. A cell culture medium comprising glycine at a concentration below 2 mM.

216. The cell culture medium of any one of embodiments 180 to 215 wherein said concentration is below 1 mM.

217. The cell culture medium of any one of embodiments 180 to 215 wherein said concentration is between 0.1 and 2 mM.

218. The cell culture medium of any one of embodiments 180 to 215 wherein said concentration is between 0.1 and 1 mM.

219. The cell culture medium of any one of embodiments 180 to 215 wherein said concentration is between 0.2 and 1 mM.

220. The cell culture medium of any one of embodiment 180 to 215 wherein said concentration is between 0.5 and 1 mM.

221. The cell culture medium of any one of embodiment 180 to 220 wherein said medium further comprises at least 1, 2, 3, 4, 5, 6, 7, 8 or 9 of valine, isoleucine, proline, lysine, arginine, histidine, aspartate, glutamate and asparagine at a concentration above 2 mM.

222. The cell culture medium of any one of embodiment 180 to 220 wherein said medium comprises at least 5 of valine, isoleucine, proline, lysine, arginine, histidine, aspartate, glutamate and asparagine at a concentration above 2 mM.

223. The cell culture medium of any one of embodiment 180 to 220 wherein said medium comprises valine, isoleucine, proline, lysine, arginine, histidine, aspartate, glutamate and asparagine at a concentration above 2 mM.

224. The cell culture medium of any one of embodiment 180 to 220 wherein said medium comprises valine, isoleucine, proline, lysine, arginine, histidine, aspartate, glutamate and asparagine at a concentration above 1 mM.

225. The cell culture medium of any one of embodiment 221 to 224 wherein said concentration is above 3 mM.

226. The cell culture medium of any one of embodiment 180 to 225 wherein said medium comprises valine at a concentration above 3 mM.

227. The cell culture medium of any one of embodiment 180 to 226 wherein said medium comprises valine at a concentration above 5 mM.

228. The cell culture medium of any one of embodiment 180 to 227 wherein said medium comprises valine at a concentration above 10 mM.

229. The cell culture medium of any one of embodiment 180 to 228 wherein said medium comprises isoleucine at a concentration above 3 mM.

230. The cell culture medium of any one of embodiment 180 to 229 wherein said medium comprises isoleucine at a concentration above 5 mM.

231. The cell culture medium of any one of embodiment 180 to 230 wherein said medium comprises isoleucine at a concentration above 10 mM.

232. The cell culture medium of any one of embodiment 180 to 231 wherein said medium comprises cysteine at a concentration above 1.5 mM, and preferably above 3 mM.

233. The cell culture medium of any one of embodiment 180 to 232 wherein said medium comprises cysteine at a concentration above 5 mM.

234. The cell culture medium of any one of embodiment 180 to 233 wherein said medium comprises cysteine at a concentration above 10 mM.

235. The cell culture medium of any of embodiments 180 to 234 for use in a method of any one of embodiments 1 to 164 and 166 to 179.

236. The cell culture medium of any of embodiments 180 to 234 for use as a base medium in a method of any one of embodiments 1 to 164 and 166 to 179.

237. The cell culture medium of any of embodiments 180 to 234 for use as a feed medium in a method of any one of embodiments 1 to 164 and 166 to 179.

238. The method of any one of embodiments 1 to 164 and 166 to 179 wherein the medium of embodiments 146 to 184 is used as a feed medium.

239. The method of any one of embodiments 1 to 164 and 166 to 179 wherein the medium of embodiments 146 to 184 is used as a base medium.

EXAMPLES

Example 1: Identification of the Metabolic Byproducts, Accumulating in Fed-Batch Cultures, which have Inhibitory Effects on Growth of Mammalian Cells in Culture Goal:

This experiment was carried out to identify the major growth inhibitors (metabolic byproducts) accumulating in the glucose restricted and conventional fed-batch cultures of mammalian cells, using global metabolite profiling approaches.

Materials and Methods:

Cells and Medium

CHO cells comprising a glutamine synthase expression system (commercially available from Lonza) (hereafter GS-CHO, Cell line A) and expressing a recombinant antibody were used in the current experiment. Two types of medium were used in this experiment. First medium is "Medium A" which is used for inoculation of the experiment on day 0 of the culture. Second medium is "Medium B" which is the enriched nutrient media used as a feed medium for conventional and HIPDOG fed-batch processes (described in the next section).

Medium A is a fortified version of insulin-free Medium 9 (U.S. Pat. No. 7,294,484, table 14), with slight differences in concentrations of sodium bicarbonate and potassium chloride, and containing Pluronic F68 instead of polyvinyl alcohol. It was fortified by adding 10% glutamine-free Medium 5 (U.S. Pat. No. 7,294,484, table 7), and by further raising the concentrations of eight amino acids (Glu, Tyr, Gly, Phe, Pro, Thr, Trp and Val). The concentrations of amino acids are listed in the Table 1 below.

TABLE 1

Concentration of Amino Acids in Medium A

| Amino Acids | Concentration in Medium A (mM) |
|---|---|
| alanine | 0.4 |
| arginine | 5.3 |
| asparagine•H2O | 21.1 |
| aspartic acid | 2.3 |
| cysteine•HCl•H2O | 0.4 |
| cystine•2HCl | 1.5 |
| glutamic acid | 0 |
| monosodium glutamate | 2.0 |
| glutamine | 0 |
| glycine | 3.6 |
| histidine•HCl•H2O | 2.7 |
| isoleucine | 5.4 |
| leucine | 9.4 |
| lysine•HCl | 8.9 |
| methionine | 3.1 |
| phenylalanine | 4.5 |
| proline | 9.1 |
| serine | 11.8 |
| threonine | 10.8 |
| tryptophan | 2.3 |
| tyrosine•2Na•2H2O | 5.1 |
| valine | 10.3 |

Medium B has the same composition as Medium 5 (U.S. Pat. No. 7,294,484, table 7), but with higher levels of the amino acids (by a factor of 2.5). The concentrations of amino acids in Medium B are shown in Table 2.

TABLE 2

Concentration of Amino Acids in Medium B

| Amino Acids | Concnetration in Medium B (mM) |
|---|---|
| alanine | 6.0 |
| arginine | 32.9 |
| asparagine•H$_2$O | 54.0 |
| aspartic acid | 15.0 |
| cysteine•HCl•H$_2$O | 0.0 |
| cystine•2HCl | 4.7 |
| glutamic acid | 6.0 |
| monosodium glutamate | 0.0 |
| glutamine | 0.0 |
| glycine | 6.0 |
| histidine•HCl•H$_2$O | 10.5 |
| isoleucine | 27.0 |
| leucine | 38.9 |
| lysine•HCl | 30.0 |
| methionine | 12.0 |
| phenylalanine | 15.0 |
| proline | 18.0 |
| serine | 45.2 |
| threonine | 24.0 |
| tryptophan | 4.8 |
| tyrosine•2Na•2H$_2$O | 12.0 |
| valine | 24.0 |

Bioreactor Setup

Two conditions were employed including conventional fed-batch process and a glucose restricted fed-batch process. In the glucose restricted fed batch process (hereafter HIPDOG culture), glucose was limited by using the HIPDOG technology (Gagnon et al, 2011). The pH dead-band used while the HIPDOG control was operational was 7.025+/−0.025.

The conventional process was identical to the HIPDOG process with respect to inoculum cell density targeted (1E6 cells/mL), the media used, culture volume (14 the amount of feed added daily to the culture, and the process parameters including the temperature (36.5 C), pH (6.9-7.2) and the agitation rate (267 rpm). The two cultures only differed in their glucose levels. In the conventional culture, glucose was maintained at greater than 2 g/L between days 2 through 5, while in the HIPDOG culture glucose was consumed by the cells naturally until the glucose level fell to a point at which the cells began to also consume lactic acid (observed by a slight rise in pH of the culture) and the HIPDOG technology/feeding strategy commenced. Post day 5 the glucose levels in both the conditions were maintained at concentrations above 2 g/L by feeding glucose as necessary and were treated similarly until day 12. Viable cell density, lactate and ammonia concentration in the cell culture medium were measured on a daily basis for both the conditions. The base medium used is Medium A and the feed medium used was Medium B.

For metabolomic analysis, spent medium samples and the cell pellet samples were collected and analyzed from duplicate reactors runs, performed for each condition. Time points considered for the analysis include days 0, 2, 3, 5, 7, 9 and 10. Metabolomic approach used employed both NMR (groups 4 and 5 of Table 3), LC/MS and GC/MS (groups 1 to 3 of table 3) techniques to assess the relative levels of metabolites at different time points of the culture. The details of the sample preparation and the type of equipment/methods used for NMR, LC/MS and GC/MS analysis are described below. The relative levels (fold changes) of all metabolites were measured and calculated. The relative levels were determined in both the spent medium and cell pellet samples, which were calculated based on fold changes compared to the level of the metabolite when first detected. The fold changes were used to identify the metabolites that were accumulating to very high levels by day 7 of the HIPDOG and the conventional fed-batch culture.

Methods for Metabolomic Analysis

Liquid/Gas Chromatography with Mass Spectrometry

Sample preparation was conducted using a methanol extraction to remove the protein fraction while allowing maximum recovery of small molecules. The resulting extract was dried under vacuum and subsequently used for sample preparation for the appropriate instrument, either LC/MS or GC/MS.

The LC/MS portion of the platform was based on a Waters ACQUITY UPLC and a Thermo-Finnigan LTQ mass spectrometer, which consisted of an electrospray ionization (ESI) source and linear ion-trap (LIT) mass analyzer. The sample was analyzed independently in both positive and negative ion modes. Sample was reconstituted in acidic conditions for positive ion mode and was gradient eluted using water and methanol, both containing 0.1% Formic acid, whereas for negative ion mode sample was reconstituted in basic extracts, which also used water/methanol, contained 6.5 mM ammonium bicarbonate for gradient elution. The MS analysis alternated between MS and data-dependent $MS^2$ scans using dynamic exclusion.

The samples destined for GC/MS analysis were re-dried under vacuum desiccation for a minimum of 24 hours prior to being derivatized under dried nitrogen using bistrimethylsilyl-triflouroacetamide (BSTFA). The GC column was 5% phenyl and the temperature ramp is from 40° to 300° C. in a 16 minute period. Samples were analyzed on a Thermo-Finnigan Trace DSQ fast-scanning single-quadrupole mass spectrometer using electron impact ionization. The instrument was tuned and calibrated for mass resolution and mass accuracy on a frequent basis.

The data was extracted from the raw mass spec data files and peaks were identified. Subsequently, the peaks were annotated and quantified (arbitrary intensity values) with compound information by comparison to library entries of purified standards or recurrent unknown entities. The combination of chromatographic properties and mass spectra gave an indication of a match to the specific compound or an isobaric entity.

NMR Sample Preparation, Data Acquisition and Processing

1000 μL of each sample was filtered using Nanosep 3K Omega microcentrifuge filter tubes for 60 minutes, and 630 μL of the filtered sample was used for NMR analysis. These filters are preserved with glycerol, and as such some trace amounts of glycerol may appear in the analysis. Internal standard solution was added to each sample solution, and the resulting mixture was vortexed for 30 s. 700 μL of the centrifuged solution was transferred to an NMR tube for data acquisition.

NMR spectra were acquired on a Varian four-channel VNMRS 700 MHz NMR spectrometer equipped with a cryogenically cooled 1H/13C triple resonance biomolecular probe with auto tuning. The pulse sequence used was a 1 D-tnnoesy with a 990 ms presaturation on water and a 4 s acquisition time. Spectra were collected with 32 transients and 4 steady-state scans at 298 K.

Spectra were processed and .cnx files were generated using the Processor module in Chenomx NMR Suite 8.0. Compounds were identified and quantified using the Profiler module in Chenomx NMR Suite 8.0 with the Chenomx Compound Library version 9, containing 332 compounds. For reporting purposes, the profiled concentrations have been corrected to reflect the composition of the original sample, instead of the contents of the NMR tube. During sample preparation, each sample is diluted by introducing an internal standard and, where necessary, to increase the analyzed volume of a small sample.

Figures 1A, 1B:
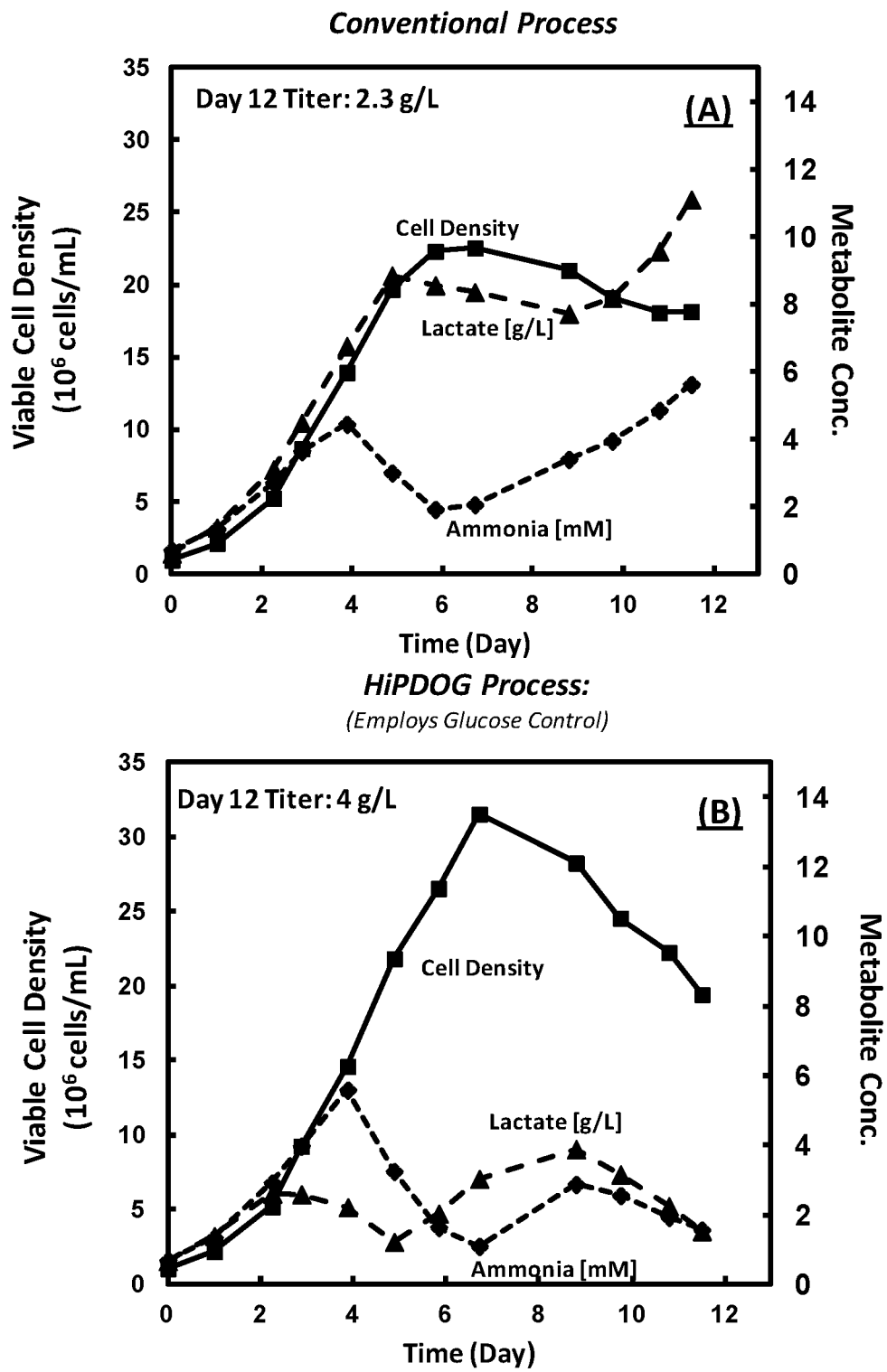
FIG. 1A shows the growth characteristics and metabolic profiles of CHO cells in conventional fed-batch process. Reported data includes viable cell densities (closed squares), culture lactate levels (closed triangles) and ammonia levels (closed diamonds). Also, reported is the harvest titer (day 12 protein concentration).
FIG. 1B shows the growth characteristics and metabolic profiles of CHO cells in a HiPDOG process. Reported data includes viable cell densities (closed squares), culture lactate levels (closed triangles) and ammonia levels (closed diamonds). Also, reported is the harvest titer (day 12 protein concentration).
Figure 2:
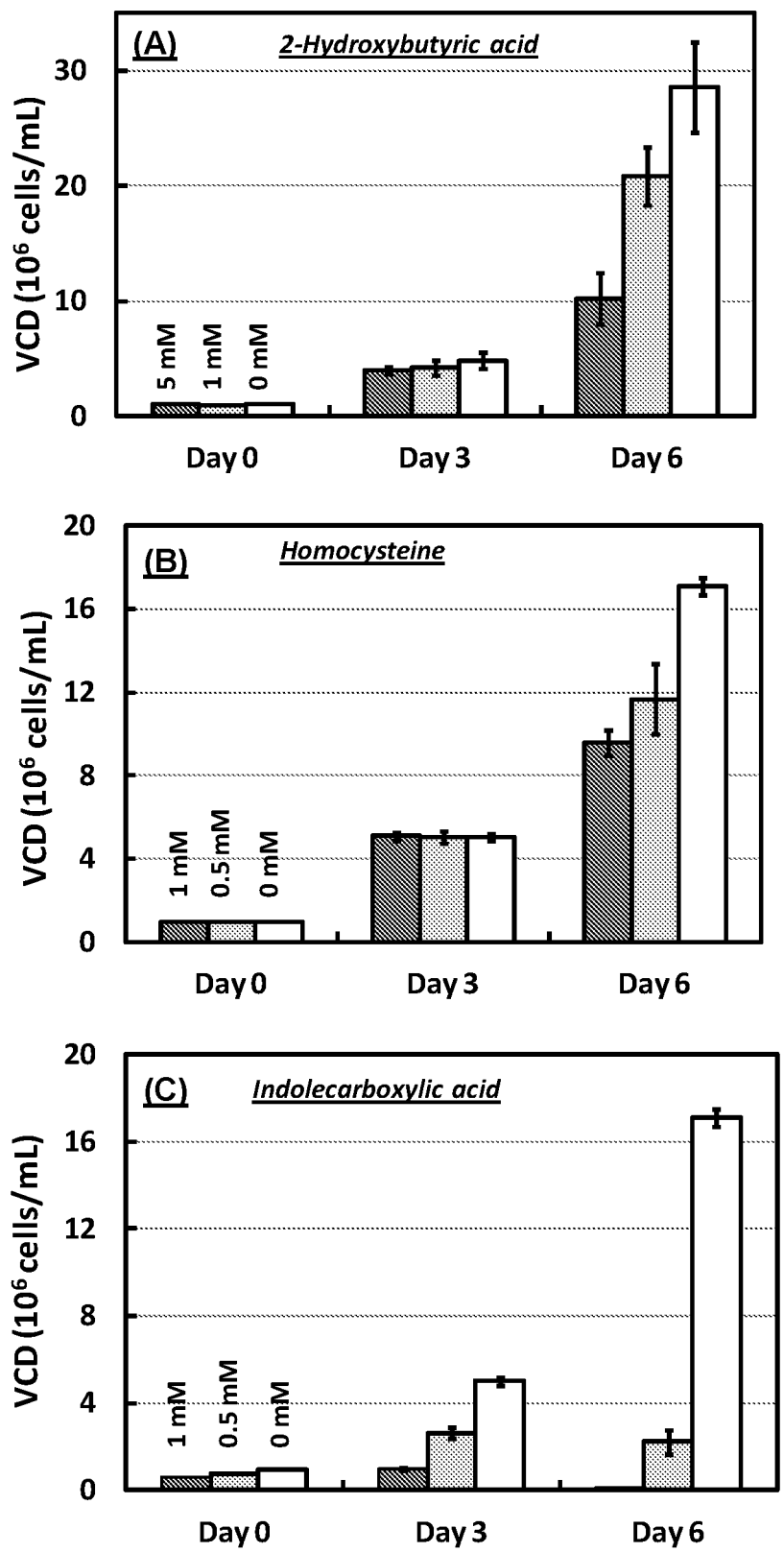
FIG. 2 shows graphs indicating the viable cell density of GS-CHO cells at day 0, Day 3 and Day 6 when exposed to increasing concentrations of 2-hydroxybutyric acid (FIG. 2A), homocysteine (FIG. 2B) or indolecarboxylic acid (FIG. 2C). GS-CHO cells were inoculated in Medium A at low viable cell densities and were treated with reported concentrations of the inhibitors, individually. The effect of the inhibitors on growth of the cells was monitored for 6 days.
Figure 3:
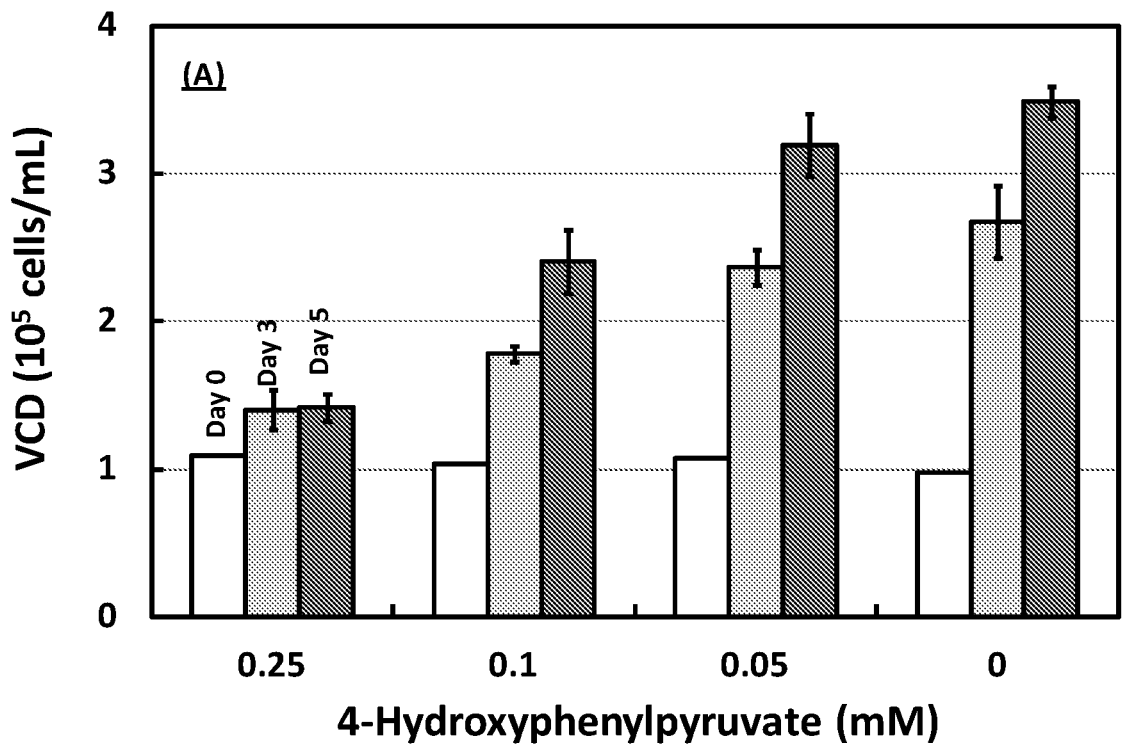
FIG. 3 shows the effect of increasing concentrations of two metabolites, 4-hydroxyphenylpyruvate (FIG. 3A) and phenyllactate (FIG. 3B) on viable cell density of the GS-CHO cells. GS-CHO cells were inoculated in Medium A at low viable cell densities and were treated with reported concentrations of the inhibitors, individually.
Figure 3:
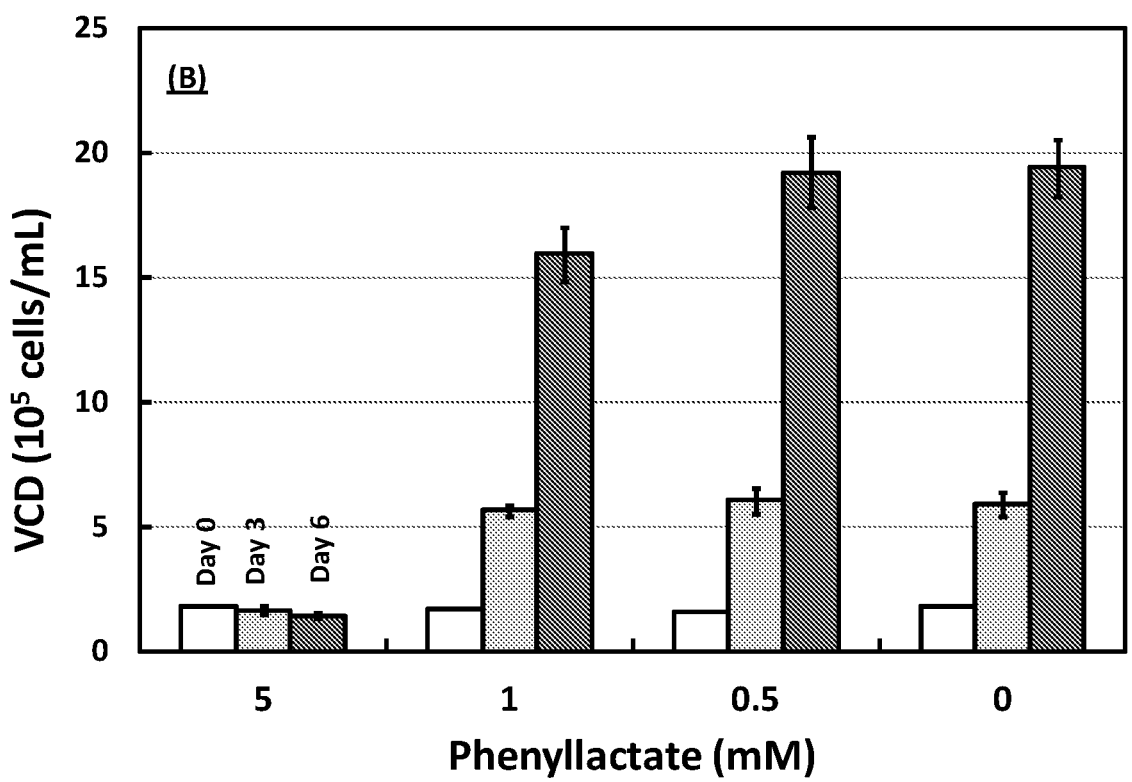
Figure 4:
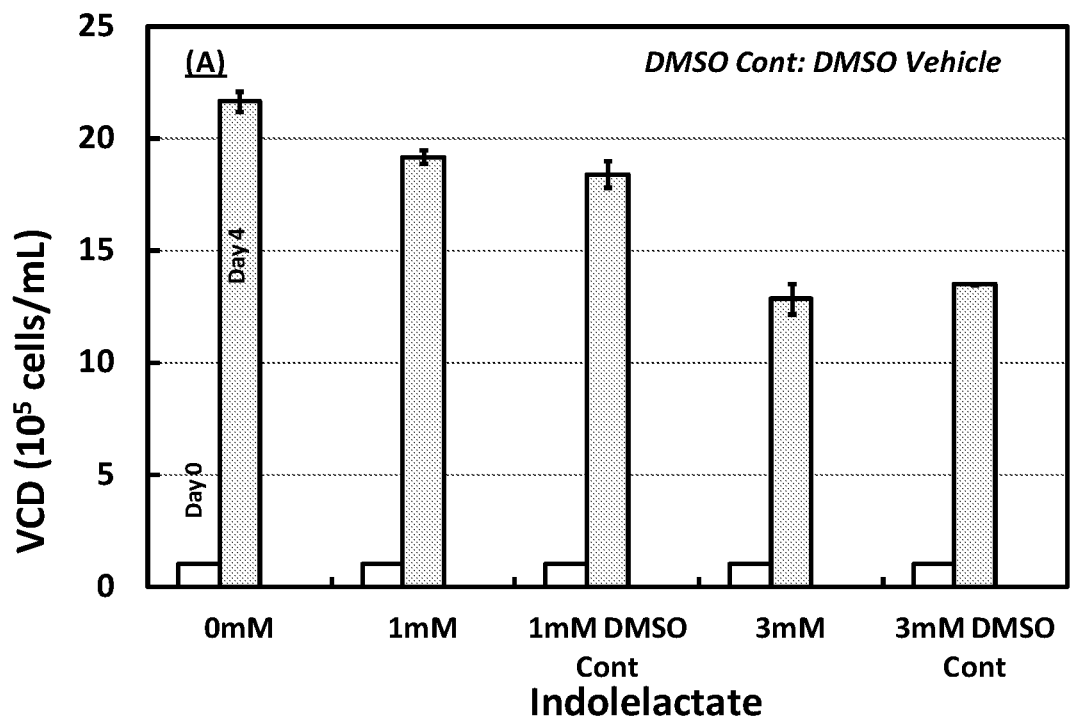
FIGS. 4 and 5 show the effect of increasing concentrations of four metabolites, indolelactate (FIG. 4A), 3-(4-hydroxyphenyl)lactate (FIG. 4B), sodium formate (FIG. 5A) and isovalerate (FIG. 5B), on viable cell density of the GS-CHO cell. GS-CHO cells were inoculated in Medium A at low viable cell densities and were treated with reported concentrations of the inhibitors, individually.
Figure 4:
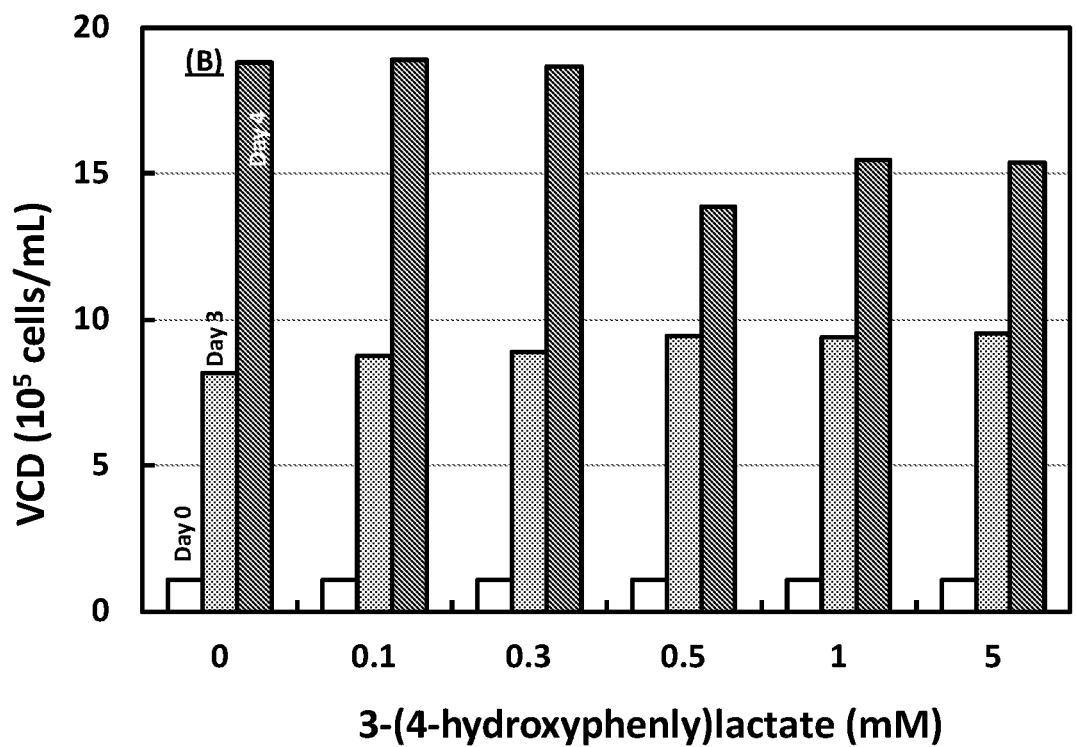
Figure 5:
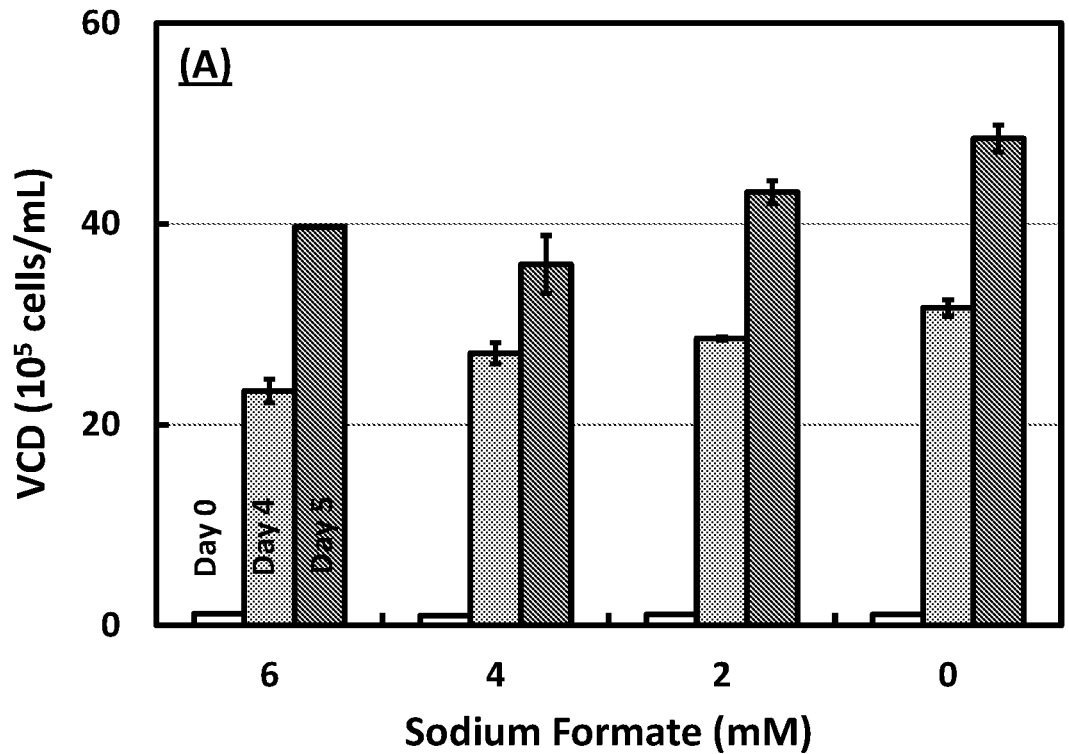
Figure 5:
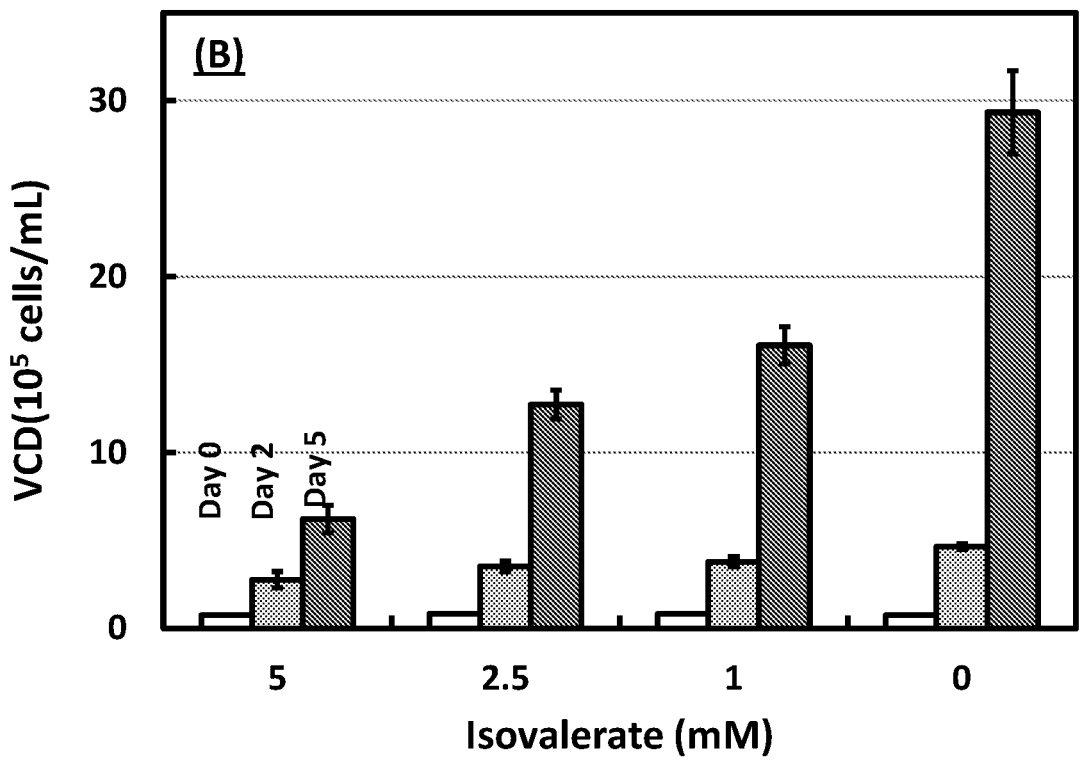

Results:

Initially cells grew exponentially in both conventional and HIPDOG cultures and attained peak cells densities on day 6 and day 7, respectively, with HIPDOG culture peaking at much higher cell densities (FIG. 1). The lactate levels in the HIPDOG process remained low due to application of the HIPDOG control (between day 2-day 5) whereas the lactate levels accumulated to very high levels in case of the conventional fed-batch culture. Ammonia was also maintained at low levels during the conventional and HIPDOG culture by the use of cells comprising a glutamine synthetase expression system. The titer (amount of protein of interest per liter of cell culture medium) was measured at the end of the culture (Day 12). The HIPDOG culture attained higher titer compared to the conventional process. The differences in the cell densities and titer values are likely an outcome of the differences in the lactate accumulations observed between the two cultures.

The metabolites that were accumulating to high levels on day 7 of the HIPDOG culture were identified based on the fold changes measured using the global metabolite profiling techniques. For each of the above identified metabolites, the concentration at which the metabolite affects the growth of the cell negatively was determined through spike-in experiments using purified compounds (see example 3). The results of these experiments were used to narrow the list of the putative novel inhibitors. A total of 9 inhibitors were identified by this process. The list of the 9 metabolites identified as potential inhibitors as well as their potential metabolic source in the cell culture medium are reported in Table 3.

TABLE 3

Shows the Names and the Functional Classes of the Nine Metabolites Identified as Putative Growth Inhibitors Accumulating in the GS-CHO Fed-Batch Cultures

| Group | Metabolite | Functional Class |
|---|---|---|
| 1 | 3-(4-hydroxyphenyl)lactate (HPLA) | Phenylalanine & tyrosine metabolism |
|  | 4-hydroxyphenylpyruvate |  |
|  | Phenyllactate (PLA) | Phenylalanine metabolism |
| 2 | Indolelactate (indole-3-lactate) | Tryptophan metabolism |
|  | Indolecarboxylic acid (indole-3-carboxylic acid) |  |
| 3 | Homocysteine | Methionine metabolism |
|  | 2-hydroxybutyric acid |  |
| 4 | Isovalerate | Leucine |
| 5 | Formate | Serine, Threonine and Glycine |

Example 2: Determination of the Concentration to which the Putative Inhibitors Accumulate in Late Stages of HIPDOG Fed-Batch Cultures Goal:

This experiment was carried out to assess the concentrations of newly identified putative growth inhibitors (metabolic byproducts) at different time points in the HIPDOG fed-batch cultures of GS-CHO cells.

Materials and Methods:

Experimental setup is same as the one defined in Example 1. Quantification was performed by LC/MS and GC/MS methods for metabolites in the first two groups of Table 1 and NMR technology was used for quantification of the metabolites in groups 4 and 5. For first two groups of the metabolites listed in the metabolite column of Table 1, purified compounds were obtained commercially and solutions of these compounds at known concentrations were prepared using the Medium A as the base solvent. Using a similar LC/MS and GC/MS global metabolite profiling approach as that used for inhibitor identification and relative quantification (see Example 1), independent calibration curves for four metabolites were prepared. These calibration curves are mathematical correlations of the actual amounts of the metabolite used in LC/MS and GS/MS techniques to the intensity values generated by the same. The correlations are subsequently used along with the intensity values generated in Example 1 to calculate the concentration of the metabolites at different time points in the culture.

Results:

The concentrations of newly identified metabolites from the first two groups of Table 3 were determined using the calibration curves developed, and the concentrations for the metabolites listed in groups 4 and 5 were determined by NMR technology as discussed in the Materials and Methods section of Example 1. The concentration of six putative inhibitors (phenyllactate, 3-(4-hydroxyphenyl)lactate, 4-hydroxyphenylpyruvate, indolelactate, isovalerate and formate) on day 7 of the HIPDOG fed-batch cultures are listed Table 4.

TABLE 4 concentrations of six metabolites on day 7 of the HIPDOG culture

| Metabolite | Day 7 Concentration (mM) |
|---|---|
| 3-(4hydroxyphenyl)lactate (HPLA) | 0.38 |
| 4-hydroxyphenylpyruvate | 0.08 |
| Phenyllactate (PLA) | 0.20 |
| Indolelactate | 0.26 |
| Isovalerate | 2.41 |
| Formate | 3.97 |

Example 3: Experiment to Establish the Growth Suppressive Effect of Identified Putative Inhibitors at the Concentrations Detected on Day 7 of the HIPDOG Fed-Batch Culture Goal:

This experiment was carried out to assess the effect of the newly identified putative inhibitors, at the concentrations determined on day 7 of the HIPDOG culture, on growth of GS-CHO cells in culture. The independent effect of the nine metabolites (phenyllactate, 3-(4-hydroxyphenyl)lactate, 4-hydroxyphenylpyruvate, indolelactate, indolecarboxylic acid, homocysteine, 2-hydroxybutyric acid, isovalerate and formate) on growth of cells was tested first. Subsequently, synergistic effect for four metabolites (phenyllactate, 3-(4-hydroxyphenyl)lactate, 4-hydroxyphenylpyruvate and indolelactate) on cell growth was tested.

Materials and Methods:

GS-CHO cells producing a recombinant antibody were inoculated at low viable cell densities (0.1E6 cells/mL) in various conditions in 5 ml volume, 6-well plate cultures. These conditions include fresh Medium A or fresh Medium A spiked-in with four putative inhibitors at concentrations detected on day 7 of the HIPDOG culture of Example 1 (phenyllactate at 0.2 mM, 3-(4-hydroxyphenyl)lactate at 0.38 mM, 4-hydroxyphenylpyruvate at 0.08 mM and indolelactate at 0.26 mM). In a separate experiment, GS-CHO cells producing a recombinant antibody were inoculated at low viable cell densities in fresh Medium A spiked-in with different concentrations of 9 inhibitors (indolecarboxylic acid, homocysteine, 2-hydroxybutyric acid, phenyllactate, 3-(4-hydroxyphenyl)lactate, 4-hydroxyphenylpyruvate, indolelactate, isovalerate and formate) with one inhibitor at a time per condition. The pH of the Medium A, spiked-in with any one of the nine metabolites or any combination of the nine metabolites, was adjusted to 7 before inoculating the cells (on day 0). The concentrations tested are:

indolecarboxylic acid: 0, 0.5 and 1 mM
    homocysteine: 0, 0.5 and 1 mM
    2-hydroxybutyric acid: 0, 1 and 5 mM
    phenyllactate: 0, 1 and 5 mM
    3-(4-hydroxyphenyl)lactate: 0, 0.1, 0.3, 0.5, 1 and 5 mM
    4-hydroxyphenylpyruvate: 0, 0.05, 0.1 and 0.25 mM
    indolelactate: 0, 1 and 3 mM
    isovalerate: 0, 1, 2.5 and 5 mM
    formate: 0, 2, 4 and 6 mM For indolelactate, the stock solution (500 mM) was prepared in DMSO. Hence, pure DMSO spike-in conditions ('DMSO cont' or DMSO control) were included for every concentration of indolelactate tested, so as to control for the effect of DMSO on the growth of the cells. All the conditions were run in duplicates or triplicates. Growth of the cells in above described conditions was monitored for 5 or 6 days.

Results:

The independent effect of the all the nine inhibitors on growth of the GS-CHO cells was investigated (FIG. 2, FIG. 3, FIG. 4 and FIG. 5). Indolecarboxylic acid and 4-hydroxyphenylpyruvate were observed to have a potent negative effect on growth of cells at concentrations of 1 mM or lower. Modest inhibition of growth was observed when GS-CHO cells were exposed to either homocysteine, 2-hydroxybutyric acid or 3-(4-hydroxyphenyl)lactate at concentrations higher than 0.5 mM or 1 mM. L-phenyllactate had a mild effect on growth of cells at 1 mM concentration. Indolelactate showed little or no effect on growth of cells at concentrations of 3 mM or below. Formate had a negative effect on growth at concentrations 2 mM and beyond. Isovalerate had a significant negative effect on growth of cells at concentrations above 1 mM.

Figure 6:
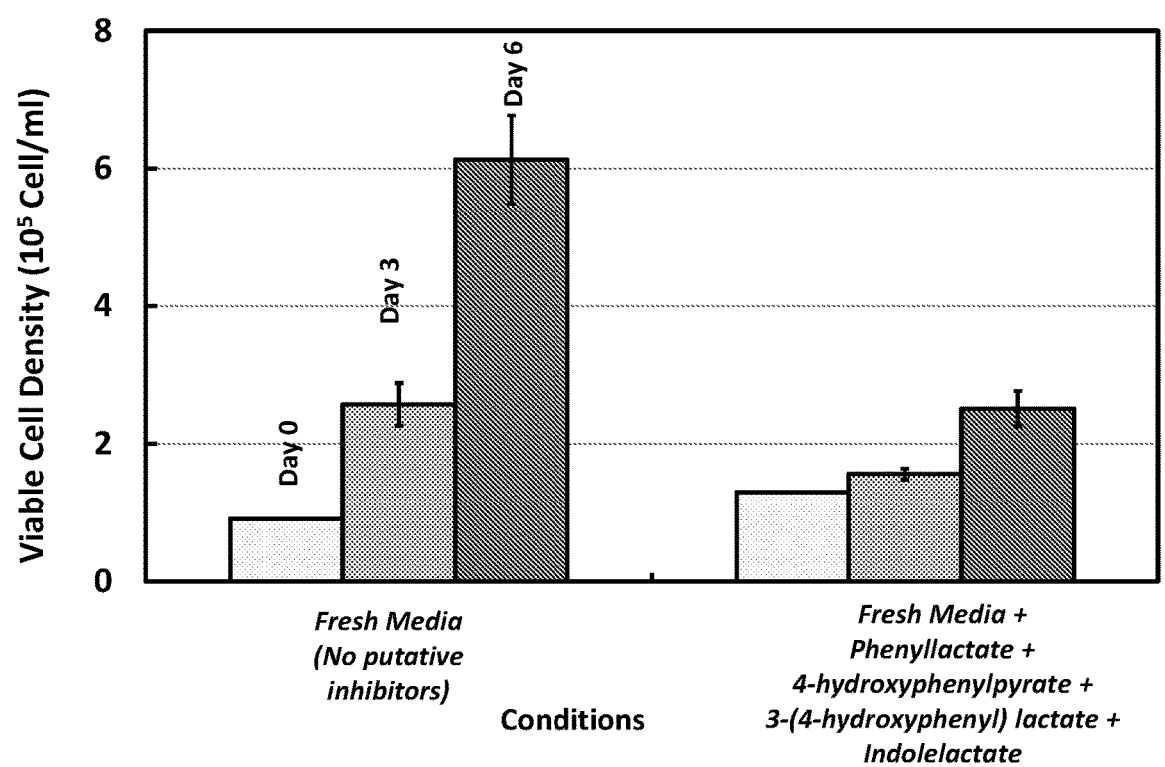
FIG. 6 shows the effect of four metabolites (4-hydroxyphenylpyruvate, indolelactate, phenyllactate, and 3-(4-hydroxyphenyl)lactate) on viable cell density of GS-CHO cells as compared to a control where cells are cultured in the absence of the metabolites. GS-CHO cells were inoculated in Medium A at low viable cell densities and were treated with fresh media alone or fresh media comprising the above mentioned four metabolites in combination at concentrations that were detected on day 7 of the HiPDOG culture (See Table 4). The effect of the inhibitors on growth of the cells was monitored for 6 days.

Earlier experiment showed that GS-CHO cells when treated independently with each of the seven putative inhibitors from groups 1 to 3, the concentration at which cell growth is inhibited was generally much higher than the concentration measured on day 7 of the HIPDOG fed-batch culture. Therefore, the effect of these inhibitors when treated in combination was subsequently evaluated. Interestingly, on treating the cells with the combination of four metabolites (phenyllactate, 4-hydroxyphenyllactate, 3-(4-hydroxyphenyl)lactate and indolelactate), at concentrations detected on day 7 of HIPDOG culture, cell growth was significantly inhibited when compared to cell growth in the fresh medium (FIG. 6). This data indicates that the above four metabolites act in a synergistic manner to inhibit growth of GS-CHO cells.

Since these four metabolites are by-products of phenylalanine, tyrosine and tryptophan metabolism, reducing the concentrations of these precursor amino acids in culture can limit the formation of corresponding inhibitory metabolites.

Further, since methionine metabolites (homocysteine and 2-hydroxybutyrate) and leucine, serine, threonine and glycine metabolites (isovalerate and formate) also have a negative effect on cell growth, reducing methionine, leucine, serine, threonine and glycine levels in culture could potentially limit the formation of these metabolites and promote cell growth.

Example 4: Reduction of the Growth Suppressive Effect of the Newly Identified Inhibitors by Nutrient Limitation Strategies in Fed-Batch Culture Goal:

This experiment was performed to reduce the formation of newly identified inhibitors by limiting the supply of the carbon sources responsible for their biosynthesis. The goal of this experiment was to assess if such reduction in inhibitor formation relieves the growth suppression in the late stages of the culture, resulting in increased maximum viable cell densities in the fed-batch cultures.

Materials and Methods:

Cells and Bioreactor Setup

GS-CHO cells expressing a recombinant antibody (cell line A) were used in the current experiment. Two conditions were tested as part of this experiment: A) HIPDOG fed-batch culture with low levels of four amino acids ((tyrosine, methionine, phenylalanine and tryptophan) (Low AA condition)), B) HIPDOG fed-batch culture with normal amino acids concentrations (control HIPDOG condition). Exponentially growing cells from seed culture were inoculated at $1 \times 10^6$ cells/mL into each production bioreactor. For both the conditions, HIPDOG strategy was in operation between day 2 and day 7 of the culture. In the low amino acid condition, the concentrations of tyrosine, tryptophan, phenylalanine and methionine were maintained between 0.5 mM and 1 mM for first seven days of the culture after which they were adjusted to the levels of each of those amino acids in the control HIPDOG condition. Post day 7 both the conditions were treated similarly. Viable cell density, lactate, ammonia and amino acid concentrations were measured on a daily basis (amino acids measured only for first seven days). For both conditions, the inoculum viable cell density targeted ($1 \times 10^6$ cells/mL), and the culture volume (1 L) and the process parameters including the temperature (36.5 C), pH (6.9-7.2) and the agitation rate (267 rpm) were identical. The base medium used in the control HIPDOG condition was Medium A and that used in Low AA condition was the modified version of Medium A with low concentrations of the four amino acids (tyrosine, tryptophan, phenylalanine and methionine at approximately 0.6 mM). The feed medium used for control HIPDOG culture was Medium B. For the Low AA condition, either the original Medium B or a modified version of Medium B with higher concentration of four amino acids (tyrosine, tryptophan, methionine and phenylalanine) was formulated and used as feed media (60% higher for methionine and ~100% higher levels for tyrosine, tryptophan and phenylalanine as compared to original feed Medium B). The levels of the four amino acids in the modified version of Medium B was configured based on the cell specific consumption rates for the four amino acids and the previously determined feeding schedule for the cell line A in a HIPDOG process. Amino acid concentrations were measured every day using a UPLC based amino acid method which is described in detail below. Based on the level of amino acids at a given sampling point and the feeding schedule, one of the two types of medium B (original or higher concentration) was chosen as the feed medium till next sampling point such that the concentration for the four amino acids are between 0.5 mM-1 mM at the next sampling time point.

Amino Acid Analysis

10 µL of either a standard amino acid mix solution or a spent medium sample (10 times diluted sample) was mixed with 70 µL of AccQ•Tag Ultra borate buffer (Waters UPLC AAA H-Class Applications Kit [176002983]), and 20 µL of AccQ•Tag reagent previously dissolved in 1.0 mL of AccQ•Tag Ultra reagent diluent was added. The reaction was allowed to proceed for 10 min at 55° C. Liquid chromatographic analysis was performed on a Waters Acquity UPLC system, equipped with a binary solvent manager, an autosampler, a column heater and a PDA detector. The separation column was a Waters AccQ•Tag Ultra column (2.1 mm i.d.×100 mm, 1.7 µm particles). The column heater was set at 55° C., and the mobile phase flow rate was maintained at 0.7 mL/min. Eluent A was 10% AccQ•Tag Ultra concentrate solvent A, and eluent B was 100% AccQ•Tag Ultra solvent B. The nonlinear separation gradient was 0-0.54 min (99.9% A), 5.74 min (90.0% A), 7.74 min (78.8% A), 8.04-8.64 min (40.4% A), 8.73-10 min (99.9% A). One microliter of sample was injected for analysis. The PDA detector was set at 260 nm. The previously determined elution times for the amino acids are used to identify the specific amino acid peaks on the chromatogram for each sample. The amino acid concentrations were estimated using the area under the peak and the calibration curve generated using the standard solution (Amino Acids Standard H, Thermo Scientific, PI-20088).

Figure 7:
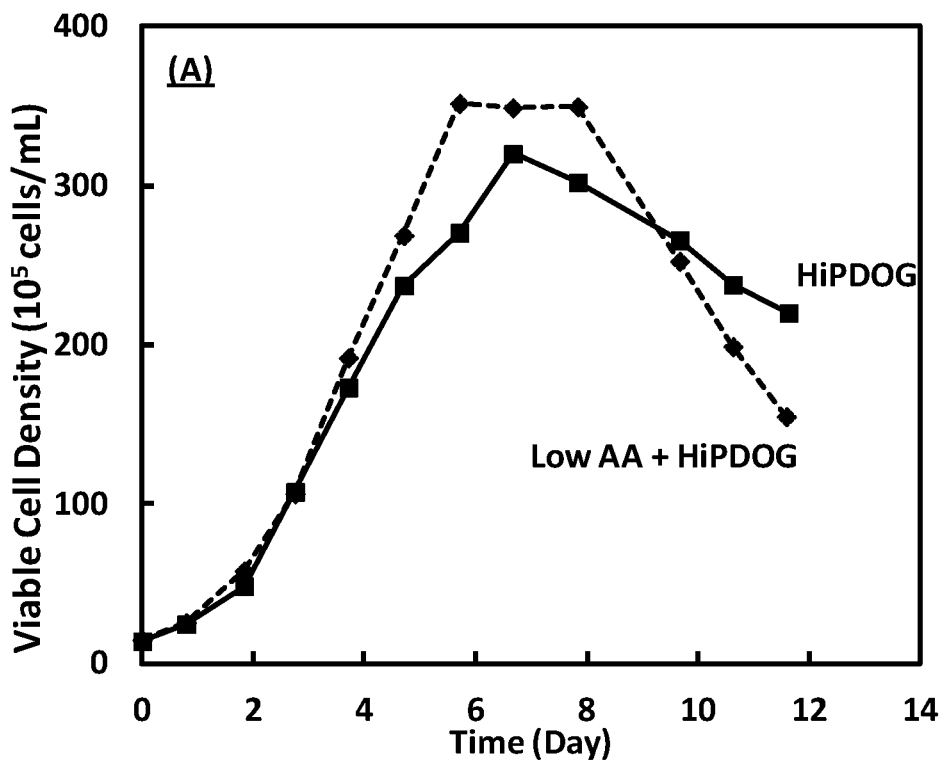
FIG. 7A shows the viable cell densities of GS-CHO cells in 'HiPDOG' process (closed squares) and 'Low AA+HiPDOG' (closed diamonds) process.
FIG. 7B shows the culture titer (IgG) at different days in 'HiPDOG' process (closed squares) and 'Low AA+HiPDOG' (closed diamonds) process.
Figure 7:
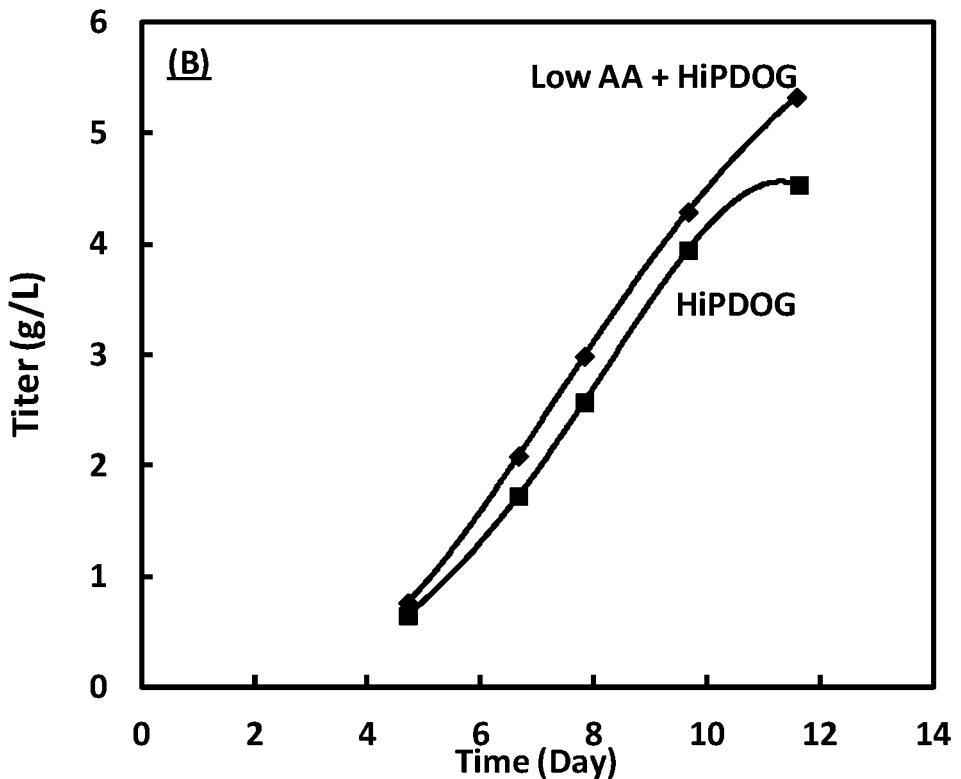
Figure 8:
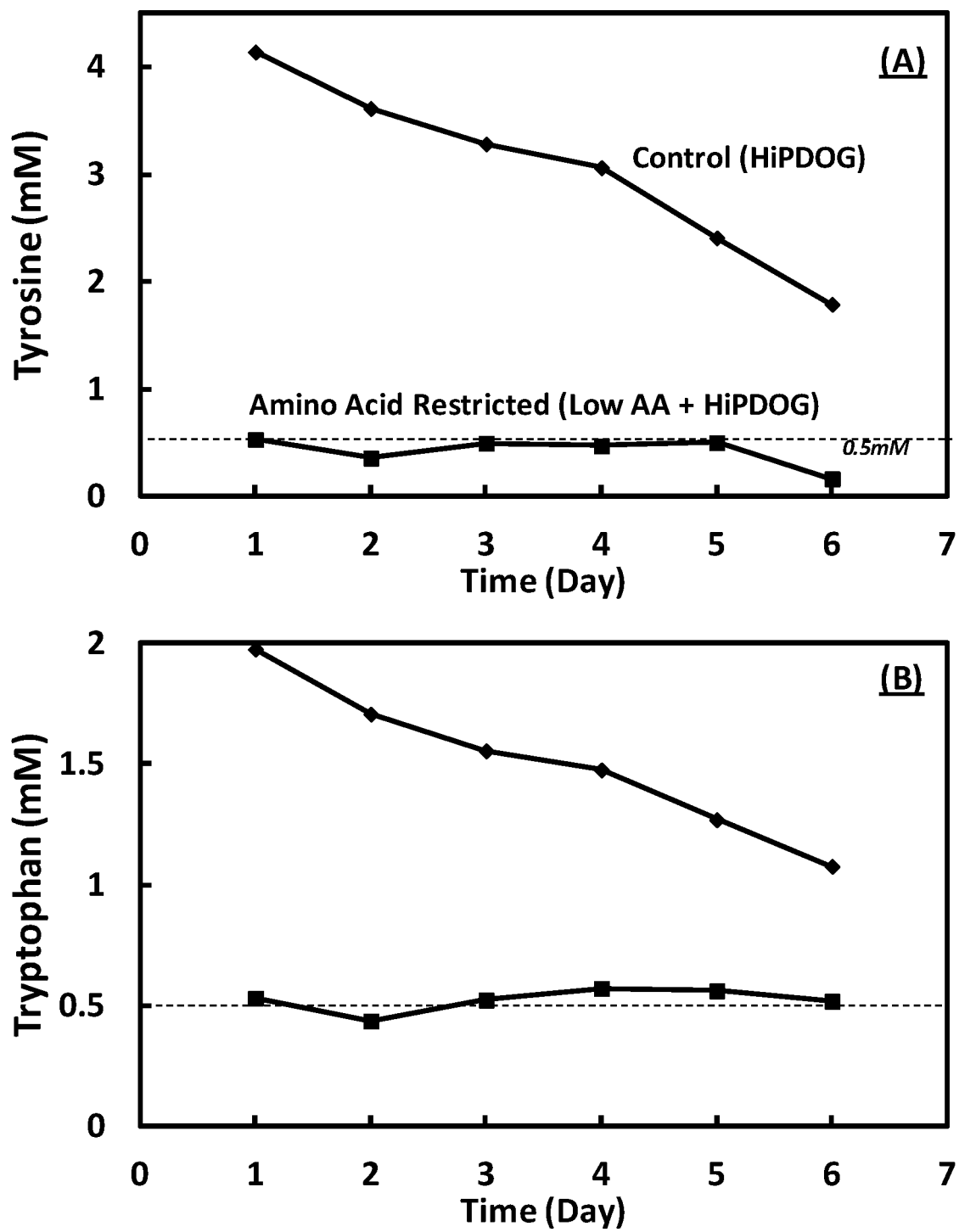
FIGS. 8 and 9 show the amino acid concentrations of four amino acids in 'amino acid restricted HiPDOG process (Low AA+HiPDOG)' (closed squares) and the 'HiPDOG' process (closed diamonds). The four amino acids include tyrosine (FIG. 8A), tryptophan (FIG. 8B), phenylalanine (FIG. 9A), and methionine (FIG. 9B).
Figure 9:
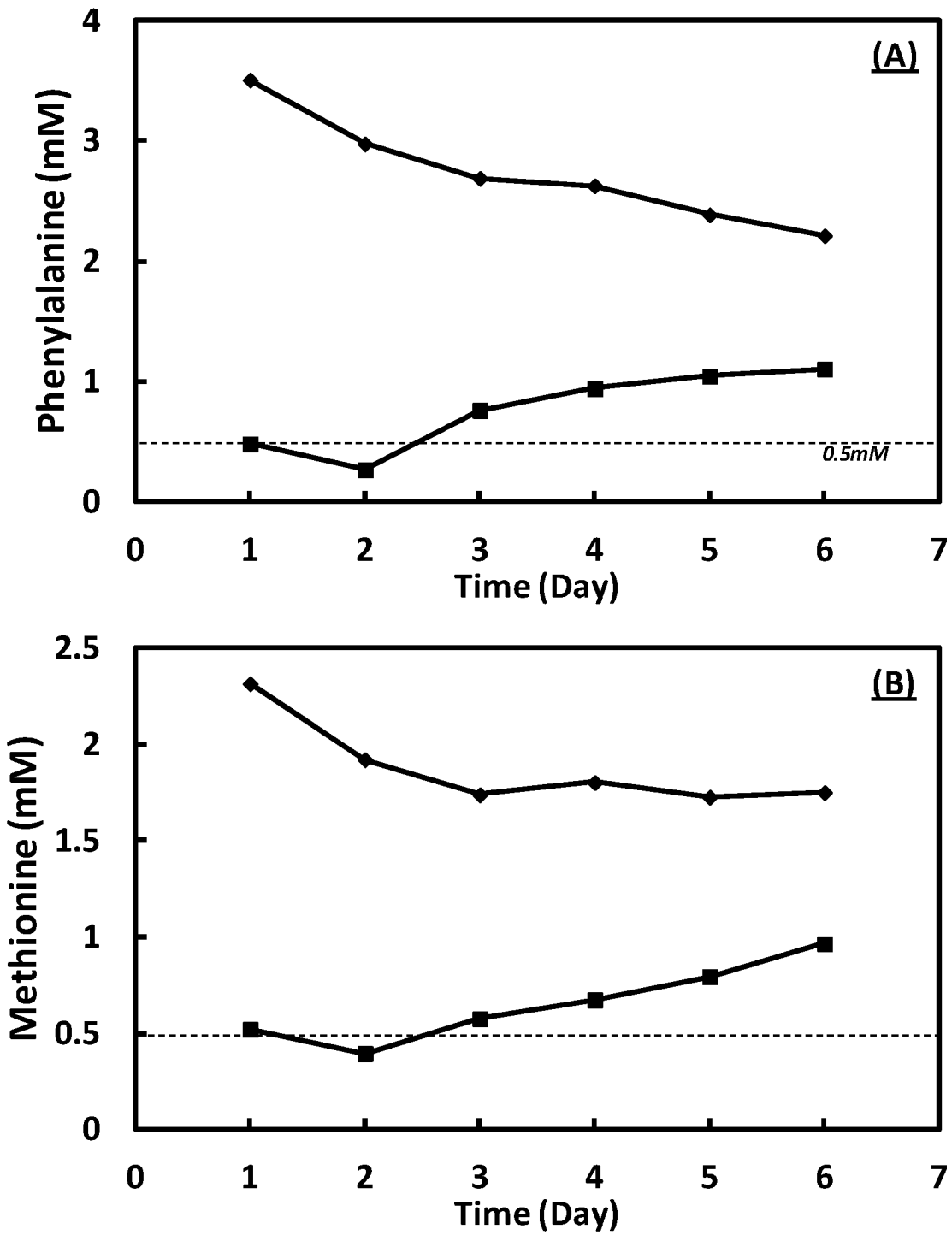

Results:

The concentrations of the amino acids were successfully maintained between 0.5 mM-1 mM in Low AA conditions (FIG. 8 and FIG. 9). The amino acid concentrations in the control HIPDOG process remained high over the course of the culture. As shown in FIG. 7, the cell densities in the Low AA condition peaked around $35 \times 10^6$ cells/ml on day 7 whereas the cell densities in control HIPDOG condition peaked around $32 \times 10^6$ cells/mL. The harvest titer levels in the Low AA condition (5.3 g/L) were 18% higher than the control condition (4.5 g/L). Clearly, limiting the amino acid supply increased the cell densities (and thereby the titer) in the late stages of the cultures.

Example 5 demonstrates that such an increase in growth and productivity can be explained as a result of reduced production of the newly identified inhibitors.

Example 5: Demonstrating (i) the Reduced Accumulation of the Newly Identified Inhibitors Through the Limitation of Amino Acids and (ii) the Reproducibility of the Positive Effect of Such Limitation of Inhibitory Metabolites on Growth of GS-CHO Cells (Cell Line A) in Fed-Batch Cultures Goal:

The main goal of this example is to demonstrate the reduction in the accumulation of the newly identified inhibitors in fed-batch cultures by limiting the supply of the carbon sources (amino acids) responsible for their biosynthesis. In this example, two experiments are included to demonstrate that such reduction in the levels of the newly identified inhibitors through limitation of four amino acids or eight amino acids relieves the growth suppression in the late stages of the fed-batch culture resulting in increased maximum viable cell densities.

Materials and Methods:
Cells and Bioreactor Setup

Cell line A was used in the two experiments performed as part of this example.

Three conditions were tested in the first experiment:
A) HIPDOG fed-batch culture with low levels of tyrosine, methionine, phenylalanine and tryptophan (Low 4AA+HIPDOG condition),
B) HIPDOG fed-batch culture with low levels of tyrosine, methionine, phenylalanine, tryptophan, leucine, serine, threonine and glycine (Low 8AA+HIPDOG condition), and,
C) two HIPDOG fed-batch cultures with normal amino acids concentrations (HIPDOG 1 and HIPDOG 2).

In a second experiment two conditions were tested:
A) HIPDOG fed-batch culture with low levels of tyrosine, methionine, phenylalanine, tryptophan, leucine, serine, threonine and glycine (Low 8AA+HIPDOG condition), and,
B) HIPDOG fed-batch culture with low levels of tyrosine, methionine, phenylalanine and tryptophan (Low 4AA+HIPDOG condition).

First experiment was run for 12 days whereas the second experiment was run for 16 days. In both the experiments, exponentially growing cells from seed cultures were inoculated at $1 \times 10^6$ cells/mL into each production bioreactor. For all the conditions, HIPDOG control was in operation in between day 2 and day 7 of the culture. In the low amino acid conditions, the concentrations of above mentioned four or eight amino acids were maintained between 0.5 mM and 1 mM for first seven days of the culture after which they were adjusted to the levels closer to the respective amino acids in the control HIPDOG conditions. Post day 7, both the conditions were treated similarly. Viable cell, ammonia and amino acid concentrations were measured on daily basis. For all the conditions, the inoculum viable cell density targeted ($1 \times 10^6$ cells/mL), the culture volume (1 L), and the process parameters including the temperature (36.5 C), pH (6.9-7.2) and agitation rate (259 rpm) were identical. The base medium used in the HIPDOG condition was Medium A and that used in low amino acid conditions was the modified version of Medium A with low concentrations of either four amino acids (tyrosine, tryptophan, phenylalanine and methionine at approximately 0.6 mM) or eight amino acids (tyrosine, tryptophan, phenylalanine, methionine, leucine, serine, threonine and glycine at approximately 0.6 mM). The feed medium used for all the conditions was Medium B. Amino acid concentrations were measured every day using UPLC based amino acid method as described in Example 4. In the low amino acid conditions, based on the level of amino acids at a given sampling point and the feeding schedule to be followed, concentrated solutions of the amino acids were supplemented to the conditions such that the concentration for the four amino acids or the eight amino acids in corresponding low amino acid conditions are between 0.5 mM-1 mM at the next sampling time point. Spent medium samples from various conditions across both the experiments were analyzed for the levels of the newly identified inhibitors using the NMR technology described in the Materials and Methods section of Example 1.

Results:

In the first experiment, the concentrations of the amino acids were successfully maintained between 0.5 mM-1 mM in both Low 4 AA and Low 8 AA conditions until day 7 of the fed-batch cultures (FIGS. 11-14). Such limitation of amino acid levels in the two conditions resulted in lower levels of accumulation of the newly identified metabolites (FIG. 15 and FIG. 16). Isovalerate, formate, 3-(4-hydroxyphenly)lactate and indole-3-lactate were specifically profiled. Isovalerate and formate are byproducts of leucine, serine, glycine and threonine, which are controlled at low levels only in Low 8 AA condition. These amino acids are not controlled at low levels in the Low 4 AA condition. Correspondingly, significantly lower concentrations of isovalerate were only seen in the Low 8 AA condition. The levels isovalerate were higher in control HIPDOG conditions and the Low 4 AA condition (FIG. 15B). Formate levels were similar across the all conditions on day 7 of the culture; however, on a per cell basis the amount of formate produced is lower in Low 8 AA condition compared to HIPDOG conditions. The other two inhibitors profiled, 3-(4-hydroxyphenly)lactate and indole-3-lactate, are byproducts of the amino acids phenylalanine and tryptophan, which are controlled at lower levels in both Low 8 AA and Low 4 AA conditions. Significantly lower concentrations of these two inhibitors were observed in both Low 8 AA and Low 4 AA conditions compared the HIDPOG conditions at day 7 (FIGS. 15A and 16).

The cells in Low 8 AA and Low 4 AA conditions grew better than the control conditions (HIPDOG1 and HIPDOG 2) peaking at cell densities $50 \times 10^6$ cells/mL and $45 \times 10^6$ cells/mL, respectively, on day 9 whereas the cell densities in control HIPDOG conditions peaked around $32 \times 10^6$ cells/mL (FIG. 10A). Such an increase in the cell growth observed in the late stages of the low amino acid conditions can be explained as an outcome of the reduced inhibitor accumulations in the culture (FIGS. 15 and 16). In addition, the low amino conditions had higher titer compared to the control HIPDOG conditions until day 9, which then tapered off to match the titer levels of HIPDOG conditions by the end of the culture (FIG. 10B). The post day 9 reduction in the protein production in the low amino acid conditions was attributed to the near exhaustion of tyrosine levels in the cultures post day 9 (FIG. 11A).

The second experiment was performed to verify and reproduce the increased positive effect of limiting leucine, serine, glycine and threonine in Low 8 AA condition when compared to Low 4 AA condition (FIG. 17). Only two conditions were tested in this experiment including the Low 8 AA and Low 4 AA condition using the cell line A. The eight amino acids or the four amino acids were controlled between 0.5 mM and 1 mM until day 7 of the culture. Amino acid data is not shown for this experiment but is similar to the amino acid profiles observed for the two conditions in above experiment (FIGS. 11-14) except for tyrosine which was not exhausted in this experiment. The cells grew better in the Low 8 AA condition peaking at $42 \times 10^6$ cells/mL on day 9 whereas the cell densities in Low 4 AA condition peaked around $33 \times 10^6$ cells/mL (FIG. 17). Such an increased cell density also translated into higher levels of harvest titer in the Low 8 AA conditions when compared to Low 4 AA condition.

Example 6: Demonstrating (i) the Reduction in the Accumulation of the Newly Identified Inhibitors Through the Limitation of Amino Acids and (ii) the Positive Effect of Such Limitation of Inhibitory Metabolites on Growth of a Different GS-CHO Cell Line (Cell Line B) in Fed-Batch Cultures Goal:

This experiment was performed to demonstrate that the growth beneficial effects of limiting the levels of certain amino acids on the growth of cells were not specific to one cell line (cell line A) but are more general and can be applied to other cell lines. Two nutrient limitations experiments were performed as part of this example using a different CHO cell line (cell line B) producing a different recombinant antibody. The goal of these experiments was to show that in fed-batch cultures, the control of amino acids at lower levels results in reduced inhibitor accumulations and such low accumulations of inhibitors can explain the increased viable cell densities and protein titers that were seen in the low amino acid fed-batch cultures.

Materials and Methods:
Cells and Bioreactor Setup

A new GS-CHO cell line (cell line B) expressing a different recombinant antibody was used in this example. Two experiments were performed to understand the effect of simultaneously limiting either four or eight amino acids. In first experiment, two conditions were tested: A) HIPDOG fed-batch culture with low levels of eight amino acids including tyrosine, methionine, phenylalanine, tryptophan, leucine, serine, glycine and threonine (Low 8 AA+HIPDOG condition) and B) HIPDOG fed-batch culture with normal amino acids concentrations (HIPDOG condition). In the second experiment, two conditions were tested: A) HIPDOG fed-batch culture with low levels of four amino acids including tyrosine, methionine, phenylalanine and tryptophan (Low 4 AA+HIPDOG condition) and B) HIPDOG fed-batch culture with normal amino acids concentrations (HIPDOG condition). First experiment was run for 12 days whereas the second experiment was only run till day 8 of the culture.

Exponentially growing cells from seed cultures were inoculated at $1 \times 10^6$ cells/mL into each production bioreactor. For all the conditions, HIPDOG strategy was in operation between day 2 and day 7 of the culture. In the low amino acid conditions, the concentrations of above mentioned four or eight amino acids were maintained between 0.5 mM and 1 mM for first seven days of the culture after which they were adjusted to the levels closer to the respective amino acids in the control HIPDOG condition. Post day 7, both the conditions were treated similarly. Viable cell, ammonia and amino acid concentrations were measured on daily basis throughout the culture. For all the conditions, the inoculum viable cell density targeted ($1 \times 10^6$ cells/mL), and the culture volume (1 L) and the process parameters including the temperature (36.5 C), pH (6.9-7.2) and the agitation rate (259 rpm) were identical. The base medium used in the HIPDOG condition was Medium A and that used in Low AA conditions was the modified version of Medium A with low concentrations of either four amino acids (tyrosine, tryptophan, phenylalanine and methionine at approximately 0.6 mM) or eight amino acids (tyrosine, tryptophan, phenylalanine, methionine, leucine, serine, threonine and glycine at approximately 0.6 mM). The feed medium used for all the conditions was Medium B. Amino acid concentrations were measured every day using UPLC based amino acid method as described in Example 4. In the low amino acid conditions, based on the level of amino acids at a given sampling point and the feeding schedule to be followed, concentrated solutions of the amino acids were supplemented to the conditions such that the concentration for the four amino acids or the eight amino acids in corresponding conditions are between 0.5 mM-1 mM at the next sampling time point. Spent medium samples from various conditions across both the experiments of this Example were analyzed to quantitate the levels of the newly identified inhibitors using the NMR technology, as described in the Materials and Methods section of Example 1.

Results:

In the first experiment, the concentrations of the eight amino acids were successfully maintained between 0.5 mM-1 mM in Low 8 AA condition until day 7 of the fed-batch cultures. Amino acid culture profiles are not shown for this experiment but are similar to those observed for the similar conditions in Experiment 1 of Example 5 (FIGS. 11-14) except for tyrosine which was not exhausted in this experiment. Such limitation of amino acid levels in the Low 8 AA condition resulted in lower levels of biosynthesis and reduced accumulation of the newly identified metabolites. Four of the nine inhibitors listed in Table 3 were profiled (FIG. 19 and FIG. 20). In Low 8 AA condition, significantly lower accumulations of isovalerate, 3-(4-hydroxyphenly)lactate and indole-3-lactate were observed compared to control HIPDOG condition. Formate levels were observed to be higher in Low 8 AA condition on day 10 of the culture, however, on a per cell basis, the amount of formate produced was similar in the Low 8 AA condition compared to the HIPDOG condition. The cells in Low 8 AA conditions grew better than the control condition (HIPDOG) peaking at cell densities of $40 \times 10^6$ cells/mL on day 9 whereas the cell densities in control HiPDOG conditions peaked around $32 \times 10^6$ cells/mL (FIG. 18A). Further, the increased growth observed in Low 8 AA condition translated into higher titer levels compared to the control HIPDOG condition (FIG. 18B). Such an increase in the cell growth and productivity observed in the low amino acid condition can be explained as an outcome of the reduced inhibitor biosynthesis and accumulation (FIGS. 19 and 20).

Figure 21:
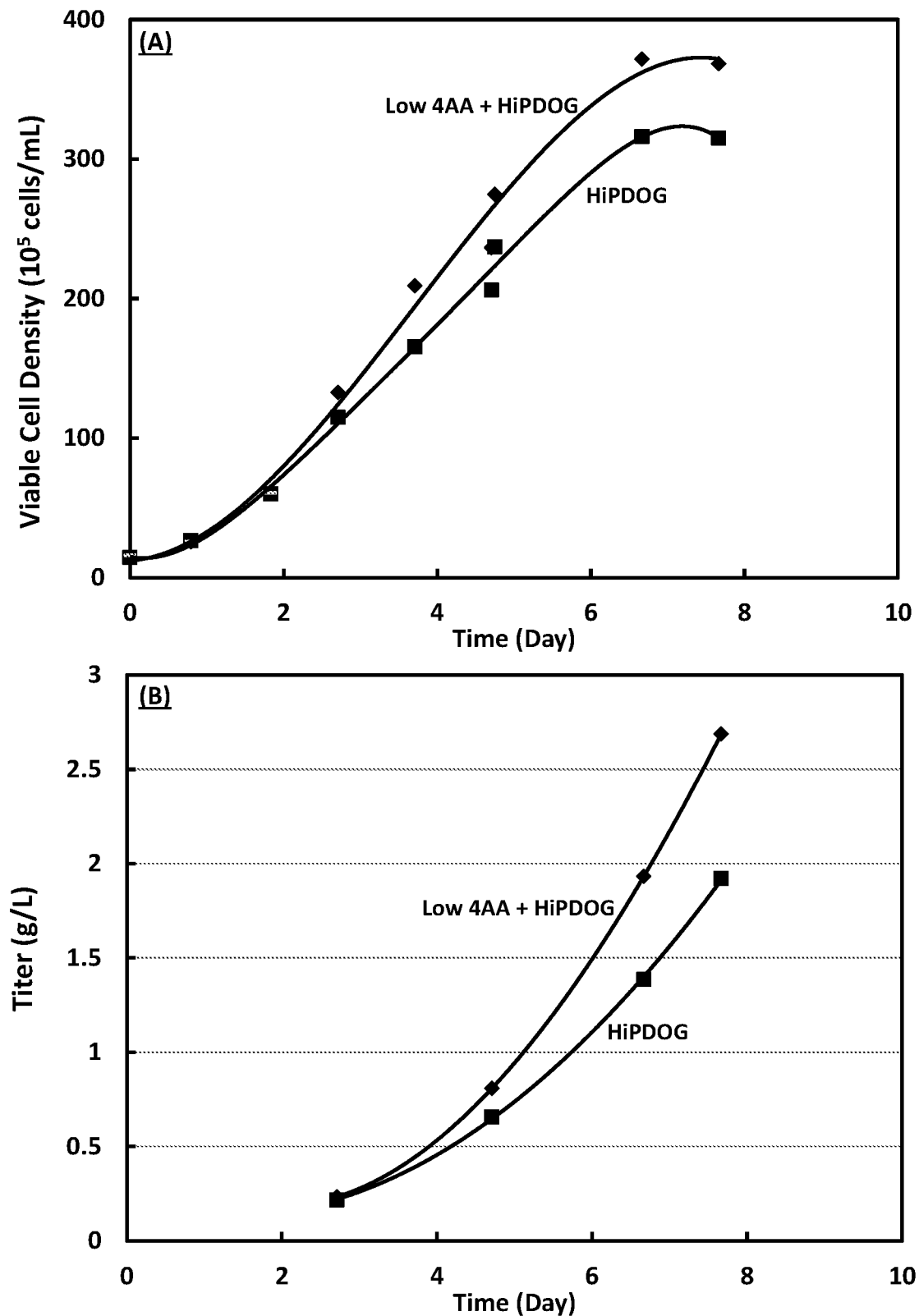

The second experiment was performed to investigate the effect of controlling the levels of four amino acids (tyrosine, phenylalanine, tryptophan and methionine) between 0.5 mM-1 mM (Low 4 AA+HIPDOG) on growth and productivity of cell line B, when compared to control HIPDOG condition (FIGS. 21-23). Amino acid culture profiles are not shown for this experiment but are similar to those observed for the similar conditions in Experiment 1 of Example 5 (FIGS. 11-14) except for tyrosine which was not exhausted in this experiment. Such limitation of amino acid levels in the Low 4 AA condition resulted in lower levels of biosynthesis and reduced accumulation of the newly identified metabolites. Four of the nine inhibitors listed in Table 3 were profiled (FIG. 22 and FIG. 23). Except isovalerate, the levels of the other three inhibitors were lower in the Low 4 AA condition compared to HIPDOG condition. Leucine not being one of the amino acids which is controlled at low levels in the Low 4 AA condition, its metabolic intermediate isovalerate accumulates in Low 4 AA condition to levels similar to those seen the control HIPDOG condition. The cells in Low 4 AA conditions grew better peaking at cell densities $37 \times 10^6$ cells/mL on day 9 of the culture whereas the cell densities in control HIPDOG condition peaked around $32 \times 10^6$ cells/mL (FIG. 21A). Further, the increased growth observed in Low 4 AA condition translated into higher titer levels compared to the control HIPDOG condition (FIG. 21B). Such an increase in the cell growth and productivity observed in the low amino acid condition can be explained as an outcome of the reduced inhibitor biosynthesis and accumulation (FIGS. 22 and 23).

Example 7: Use of RAMAN Spectroscopy for Online Measurement of the Four (Phenylalanine, Tyrosine, Tryptophan and Methionine) or Eight Amino Acids (Phenylalanine, Tyrosine, Tryptophan, Methionine, Leucine, Serine, Glycine, and Threonine) and Newly Identified Inhibitors Raman spectroscopy is based on the inelastic scattering of monochromatic light (photons) by a molecule. The technology uses the frequency shift in the light, due to a change in energy of the photon when it is absorbed and reemitted by the molecule, to determine the characteristics of the molecule. This technology has been successfully used in microbial and mammalian cell culture bioreactors with success to measure the levels of various process parameters. Raman spectroscopy has also been used to determine the concentrations of glucose, lactate, ammonia, glutamine and glutamate in CHO cell cultures.

The Raman spectra for all the amino acids have been previously reported in the literature. Raman spectra for the newly identified inhibitory metabolites is characterized using a solution of the purified metabolites. An empirical model is built by employing a training set of spectral data generated using known concentrations of each of the four or eight amino acids or the newly identified inhibitors, individually. The sample matrix (background) used for of the preparation of calibration samples (used as the training set) is a mix of spent media samples taken from different time points of different cell culture processes. The model developed using such a training set is more general and can be applied to any other cell culture process. This model is used to measure the concentration of the four or eight amino acids or the metabolites (inhibitors) in the culture (online) and accordingly control the levels of amino acids through feedback control feeding strategies.

Example 8: Suppression of Inhibitor Formation Through Control of Amino Acids at Low Levels in Fed-Batch Cultures by Using Online Measurement of Inhibitor Concentration A fed-batch process is designed to reduce the formation of the inhibitors through control of four (phenylalanine, tyrosine, tryptophan and methionine) or eight amino acids (phenylalanine, tyrosine, tryptophan, methionine, leucine, serine, glycine, and threonine) at low levels, for example between 0.2-1 mM in the cell culture medium. Such a control of the inhibitor production is attained by a feeding strategy that operates as a feed-back loop based on the online measurement of the inhibitors themselves. Such online measurements are in the form of RAMAN spectroscopy or through use of HPLC/UPLC based technology with an auto-sampler that draws sample from reactor and transfers it to the equipment in a programmed manner. As and when the concentration of the inhibitors rises above a specified level (example: 0.2 mM), the amount of phenylalanine, tyrosine, tryptophan, methionine, leucine, serine, glycine, and threonine fed to the cells is decreased until the concentration of inhibitors falls below a predefined level (for example 0.1 mM).

Example 9: Suppression of Inhibitor Formation Through Online or Offline Measurement and Control of Amino Acids at Low Levels in Fed-Batch Cultures A fed-batch process is designed to reduce the formation of the inhibitors through control of the four (phenylalanine, tyrosine, tryptophan and methionine) or eight amino acids (phenylalanine, tyrosine, tryptophan, methionine, leucine, serine, glycine, and threonine) at low levels (0.2-1 mM). Such a control of inhibitor formation is attained by a feeding strategy that operates as a feed-back loop based on the online measurement of the amino acids. Such online measurements is in the form of RAMAN spectroscopy or through use of HPLC/UPLC based technology with an auto-sampler that draws sample from reactor and transfers it to the equipment in a programmed manner. As and when the concentration of the amino acids falls below a specified level (example: 0.5 mM), estimated amounts of feed medium (similar to Medium B) is added to the culture so as to maintain the concentrations of the four or eight amino acids.

Alternatively, the samples are taken on a once per day basis and amino acid concentrations are measured offline using a UPLC/HPLC method. The amino acid concentrations obtained are used to calculate the cell specific uptake rates of the four (phenylalanine, tyrosine, tryptophan and methionine) or eight amino acids (phenylalanine, tyrosine, tryptophan, methionine, leucine, serine, glycine, and threonine) between previous two sampling time points. Assuming that the cells maintain the same specific rate of amino acid consumption until the next sampling time point, the amount of feed medium (example: Medium B) to be added till the next sampling point is determined and provided to the cells, such that the concentrations of the amino acids are always within the desired range (0.2 mM-1 mM).

Example 10: Suppression of Inhibitor Formation Through Programmed Feeding so as to Keep the Amino Acids at Low Levels in Fed-Batch Cultures The formation of the newly identified inhibitors in culture is kept low by maintaining the concentration of the four (phenylalanine, tyrosine, tryptophan and methionine) or eight amino acids (phenylalanine, tyrosine, tryptophan, methionine, leucine, serine, glycine, and threonine) at low levels in culture (0.2-1 mM). This is attained by designing a programmed feeding strategy (using modified Medium B) such that the concentrations of the amino acids, at any given time point in the culture are always within the desired range (0.2 mM-1 mM). Such a feeding strategy is contrived by assessing the specific consumption rates of amino acids at different time points along the culture and modifying the concentration in the feed medium (Medium B) such that with the above defined feeding strategy/schedule, sufficient amounts of amino acids are provided to the culture to maintain the amino acids concentrations within the desired range (0.2-1 mM).

REFERENCES

Altamirano C, Illanes A, Becerra S, Cairo J J, Godia F (2006) Considerations on the lactate consumption by CHO cells in the presence of galactose. *Journal of biotechnology* 125: 547-556

Bertoni J M (1981) Competitive inhibition of rat brain hexokinase by 2-deoxyglucose, glucosamine, and metrizamide. *Journal of neurochemistry* 37: 1523-1528

Clem B, Telang S, Clem A, Yalcin A, Meier J, Simmons A, Rasku M A, Arumugam S, Dean W L, Eaton J, Lane A, Trent J O, Chesney J (2008) Small-molecule inhibition of 6-phosphofructo-2-kinase activity suppresses glycolytic flux and tumor growth. *Molecular cancer therapeutics* 7: 110-120

Duvel K, Yecies J L, Menon S, Raman P, Lipovsky A I, Souza A L, Triantafellow E, Ma Q, Gorski R, Cleaver S, Vander Heiden M G, MacKeigan J P, Finan P M, Clish C B, Murphy L O, Manning B D (2010) Activation of a metabolic gene regulatory network downstream of mTOR complex 1. *Molecular cell* 39: 171-183

Gagnon M, Hiller G, Luan Y T, Kittredge A, DeFelice J, Drapeau D (2011) High-end pH-controlled delivery of glucose effectively suppresses lactate accumulation in CHO fed-batch cultures. *Biotechnology and bioengineering* 108: 1328-1337
Kim S H, Lee G M (2007a) Down-regulation of lactate dehydrogenase-A by siRNAs for reduced lactic acid formation of Chinese hamster ovary cells producing thrombopoietin. *Applied microbiology and biotechnology* 74: 152-159
Kim S H, Lee G M (2007b) Functional expression of human pyruvate carboxylase for reduced lactic acid formation of Chinese hamster ovary cells (DG44). *Applied microbiology and biotechnology* 76: 659-665
Lee H L T, Boccazzi P, Gorret N, Ram R J, Sinskey A J (2004) In situ bioprocess monitoring of *Escherichia coli* bioreactions using Raman spectroscopy. *Vibrational Spectroscopy* 35: 131-137
Lee J S, Lee G M (2012) Rapamycin treatment inhibits CHO cell death in a serum-free suspension culture by autophagy induction. *Biotechnology and bioengineering* 109: 3093-3102
Li B, Ryan P W, Ray B H, Leister K J, Sirimuthu N M, Ryder A G (2010) Rapid characterization and quality control of complex cell culture media solutions using raman spectroscopy and chemometrics. *Biotechnology and bioengineering* 107: 290-301
Morgan H P, O'Reilly F J, Wear M A, O'Neill J R, Fothergill-Gilmore L A, Hupp T, Walkinshaw M D (2013) M2 pyruvate kinase provides a mechanism for nutrient sensing and regulation of cell proliferation. *Proceedings of the National Academy of Sciences of the United States of America* 110: 5881-5886
Mulukutla B C, Gramer M, Hu W S (2012) On metabolic shift to lactate consumption in fed-batch culture of mammalian cells. *Metabolic engineering* 14: 138-149
Whelan J, Craven S, Glennon B (2012) In situ Raman spectroscopy for simultaneous monitoring of multiple process parameters in mammalian cell culture bioreactors. *Biotechnology progress* 28: 1355-1362
Whitehouse S, Cooper R H, Randle P J (1974) Mechanism of activation of pyruvate dehydrogenase by dichloroacetate and other halogenated carboxylic acids. *The Biochemical journal* 141: 761-774
Wlaschin K F, Hu W S (2007) Engineering cell metabolism for high-density cell culture via manipulation of sugar transport. *Journal of biotechnology* 131: 168-176
Yi W, Clark P M, Mason D E, Keenan M C, Hill C, Goddard W A, 3rd, Peters E C, Driggers E M, Hsieh-Wilson L C (2012) Phosphofructokinase 1 glycosylation regulates cell growth and metabolism. *Science* 337: 975-980
Zhou M, Crawford Y, Ng D, Tung J, Pynn A F, Meier A, Yuk I H, Vijayasankaran N, Leach K, Joly J, Snedecor B, Shen A (2011) Decreasing lactate level and increasing antibody production in Chinese Hamster Ovary cells (CHO) by reducing the expression of lactate dehydrogenase and pyruvate dehydrogenase kinases. *Journal of biotechnology* 153: 27-34
Zhu G, Zhu X, Fan Q, Wan X (2011) Raman spectra of amino acids and their aqueous solutions. *Spectrochimica acta Part A, Molecular and biomolecular spectroscopy* 78: 1187-1195

The invention claimed is:

1. A method of cell culture comprising
(i) providing cells in a cell culture medium to start a fed-batch cell culture process, and,
(ii) maintaining at least one metabolite selected from 3-(4-hydroxyphenyl)lactate, 4-hydroxyphenyl pyruvate, phenyllactate, indolelactate, indolecarboxylic acid, homocysteine, 2-hydroxybutyric acid, isovalerate and formate below a concentration C1 in the cell culture medium, wherein C1 is 3mM, wherein maintaining the at least one metabolite below a concentration C1 in the cell culture comprises the step of measuring the concentration of said at least one metabolite, and, when the measured concentration is above a predefined value, the concentration of a precursor of said at least one metabolite in the cell culture medium is decreased by reducing the amount of precursor provided to the cells via a feed medium provided to the cells,
and wherein the maximum viable cell density of the cell culture is greater than $1\times10^7$ cells/mL.

2. The method of claim 1 wherein C1 is 1mM.

3. The method of claim 1 wherein said concentration of said at least one metabolite is measured online using NMR, HPLC or UPLC.

4. The method of claim 1 wherein,
when the measured concentration of 3-(4-hydroxyphenyl) lactate, 4-hydroxyphenylpyruvate and/or phenyllactate is above said predefined value, the concentration of phenylalanine is decreased in the cell culture medium and/or,
when the measured concentration of 3-(4-hydroxyphenyl) lactate and/or 4-hydroxyphenylpyruvate is above said predefined value, the concentration of tyrosine is decreased in the cell culture medium, and/or,
when the measured concentration of indolelactate and/or indolecarboxylic acid is above said predefined value, the concentration of tryptophan is decreased in the cell culture medium and/or,
when the measured concentration of homocysteine and/or 2-hydroxybutyric acid is above said predefined value, the concentration of methionine is decreased in the cell culture medium, and/or,
when the measured concentration of isovalerate is above said predefined value, the concentration of leucine is decreased in the cell culture medium, and/or,
when the measured concentration of formate is above said predefined value, the concentration of serine, threonine and/or glycine is decreased in the cell culture medium.

5. The method of claim 1 wherein step (ii) comprises maintaining at least two metabolites selected from 3-(4-hydroxyphenyl)lactate, 4-hydroxyphenylpyruvate, phenyllactate, indolelactate, indolecarboxylic acid, homocysteine, 2-hydroxybutyric acid, isovalerate and formate below C1 in the cell culture medium.

6. The method of claim 1 wherein the cell culture medium comprises at least one of valine, isoleucine, proline, lysine, arginine, histidine, aspartate, glutamate and asparagine at a concentration above 1mM, 1.5mM, 2mM, 3mM or 5mM.

7. The method of claim 1 wherein a pH sensor is used to monitor pH of the cell culture, and, in response to a rise above a predetermined pH value, glucose is fed to the cell culture.

8. The method of claim 1, wherein the cells are CHO cells.

9. The method of claim 1, wherein the cells express a recombinant protein.

10. The method of claim 9, further comprising obtaining and purifying the recombinant protein produced by the cells.

11. The method of claim 1, wherein cell growth and/or productivity are increased as compared to a control culture, said control culture being identical except it does not comprise step (ii).

12. The method of claim 11, wherein the cell growth is determined by maximum viable cell density and is increased by at least 5% as compared to the control culture.

13. The method of claim 11, wherein the productivity is determined by titer and is increased by at least 5% as compared to the control culture.

14. The method of claim 1, wherein the maximum viable cell density of the cell culture is greater than $1 \times 10^8$ cells/mL or $5 \times 10^8$ cells/mL.

15. The method of claim 1, wherein the cell culture method comprises a growth phase and a production phase and step (ii) is applied during the growth phase.

16. The method of claim 1, wherein reducing the amount of precursor provided to the cells comprises reducing the concentration of the precursor in the feed medium.

17. The method of claim 1, wherein reducing the amount of precursor provided to the cells comprises reducing the rate of providing the feed medium to the cells.

18. The method of claim 1, wherein reducing the amount of precursor provided to the cells comprises reducing the volume of the feed medium provided to the cells.

19. The method of claim 1, wherein the concentration of isovalerate is maintained below the concentration C1 in the cell culture medium, and wherein the precursor of isovalerate is leucine.

* * * * *